(12) United States Patent
Momose et al.

(10) Patent No.: US 6,177,452 B1
(45) Date of Patent: *Jan. 23, 2001

(54) OXAZOLE DERIVATIVES, THEIR PRODUCTION AND USE

(75) Inventors: Yu Momose, Takarazuka; Hiroyuki Odaka, Kobe, both of (JP)

(73) Assignee: Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/125,756

(22) PCT Filed: Apr. 2, 1997

(86) PCT No.: PCT/JP97/01146

§ 371 Date: Aug. 25, 1998

§ 102(e) Date: Aug. 25, 1998

(87) PCT Pub. No.: WO97/36882

PCT Pub. Date: Oct. 9, 1997

(30) Foreign Application Priority Data

Apr. 3, 1996 (JP) .................................................. 8-081694

(51) Int. Cl.$^7$ ........................ C07D 413/12; A61K 31/422
(52) U.S. Cl. ........................ 514/377; 348/146; 348/183; 348/226; 348/233
(58) Field of Search ................................... 548/233, 146, 548/183, 226; 514/377

(56) References Cited

FOREIGN PATENT DOCUMENTS

| 092 239 | 10/1983 | (EP) . |
| 382 199 | 8/1990 | (EP) . |
| 612 743 | 8/1994 | (EP) . |
| 59-190979 | 10/1984 | (JP) . |
| WO 96/05186 | 2/1996 | (WO) . |

OTHER PUBLICATIONS

Sa J Org Chem 61(11) 3749–3752, 1996.*
RN 95727–51–8 in CA102:149257, 1984.*

* cited by examiner

*Primary Examiner*—Robert Gerstl
(74) *Attorney, Agent, or Firm*—Fitzpatrick, Cella, Harper & Scinto

(57) ABSTRACT

A novel compound of the formula:

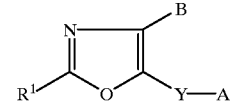

wherein $R^1$ is a halogen atom, an optionally substituted heterocyclic, hydroxy, thiol or amino group; A is an optionally substituted acyl group, an optionally substituted heterocyclic group, an optionally substituted hydroxy group, or an optionally esterified or amidated carboxy group; B is an optionally substituted aromatic group; Y is a divalent aliphatic hydrocarbon group, or a salt thereof, which have an excellent insulin secertion-promoting and blood sugar-depressing effect, and useful in agents for diabetes.

39 Claims, No Drawings

OXAZOLE DERIVATIVES, THEIR PRODUCTION AND USE

This application is a 371 of PCT/JP97/01146 filed Apr. 2, 1997.

TECHNICAL FIELD

The present invention relates to novel oxazole derivatives which are useful for prophylaxis and therapy of diabetes.

BACKGROUND ART

As agents for diabetes, heretofore, various biguanide compounds and sulfonylurea compounds have been used. However, biguanide compounds are not used at present, because these compounds induce undesirable side effects, such as lactic acidosis. Though having an excellent blood sugar-depressing effect, sulfonylurea compounds require care in use since they often induce grave hypoglycemia. Oxazole derivatives having a blood sugar-depressing effect and a sugar tolerance-improving effect are described in, for example, EP-92239, JP59-190979 and EP-382199.

The object of the present invention is to provide novel compounds which have an insulin secretion-promoting effect and a blood sugar-depressing effect, which are useful in agents for diabetes and which have low toxicity.

DISCLOSURE OF INVENTION

The novel oxazole derivatives represented by the following formula (I) have been found to possess an excellent blood sugar-depressing effect and insulin secretion-promoting effect. On the basis of this finding, we have completed the present invention.

Specifically, the present invention provides a compound of the following general formula (I):

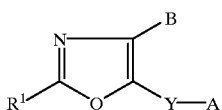

(I)

wherein $R^1$ represents a halogen atom, or an optionally substituted heterocyclic group, an optionally substituted hydroxy group, an optionally substituted thiol group or an optionally substituted amino group; A represents an optionally substituted acyl group, an optionally substituted heterocyclic group, an optionally substituted hydroxy group, or an optionally esterified or amidated carboxy group; B represents an optionally substituted aromatic group; Y represents a divalent aliphatic hydrocarbon group, or a salt thereof, and a pharmaceutical composition comprising the compound (I) or a pharmaceutically acceptable salt as an active ingredient.

In the formula (I), the heterocyclic group of the optionally substituted heterocyclic group represented by $R^1$ or A may be a 5- or 6-membered ring having 1 to 4 atoms selected from N, O and S as the ring-constituting atoms other than carbon atom(s), or a condensed ring thereof. The condensed ring includes, for example, condensed rings comprising the 5- or 6-membered ring as condensed with any of a 6-membered ring having 1 or 2 nitrogen(s), a benzene ring or a 5-membered ring having one sulfur.

Typical examples of the heterocyclic group include aromatic heterocyclic groups such as pyridyl (e.g. 2-pyridyl, 3-pyridyl, 4-pyridyl), pyrimidinyl (e.g. 2-pyrimidinyl, 5-pyrimidinyl, 6-pyrimidinyl), pyridazinyl (e.g. 3-pyridazinyl, 4-pyridazinyl), pyrazinyl (e.g. 2-pyrazinyl), pyrrolyl (e.g. 1-pyrrolyl, 2-pyrrolyl), imidazolyl (e.g. 1-imidazolyl, 2-imidazolyl, 4-imidazolyl, 5-imidazolyl), pyrazolyl (e.g. 1-pyrazolyl, 3-pyrazolyl, 4-pyrazolyl), isoxazolyl, isothiazolyl, thiazolyl (e.g. 2-thiazolyl, 4-thiazolyl, 5-thiazolyl), oxazolyl (e.g. 2-oxazolyl, 4-oxazolyl, 5-oxazolyl), 1,2,4-oxadiazolyl (e.g. 1,2,4-oxadiazol-5-yl), 1,2,4-triazolyl (e.g. 1,2,4-triazol-1-yl, 1,2,4-triazol-3-yl), 1,2,3-triazolyl (e.g. 1,2,3-triazol-2-yl, 1,2,3-triazol-4-yl), tetrazolyl (e.g. tetrazol-1-yl, tetrazol-5-yl), benzimidazolyl (e.g. benzimidazol-1-yl, benzimidazol-2-yl), indolyl (e.g. indol-1-yl, indol-3-yl), 1H-indazolyl (e.g. 1H-indazol-1-yl), 1H-pyrrolo[2,3-b]pyrazinyl (e.g. 1H-pyrrolo[2,3-b]pyrazin-1-yl), 1H-pyrrolo[2,3-b]pyridyl (e.g. 1H-pyrrolo[2,3-b]pyridin-1-yl), 1H-imidazo[4,5-b]pyridyl (e.g. 1H-imidazo[4,5-b]pyridin-1-yl), 1H-imidazo[4,5-c]pyridyl (e.g. 1H-imidazo[4,5-c]pyridin-1-yl) and 1H-imidazo[4,5-b]pyrazinyl (e.g. 1H-imidazo[4,5-b]pyrazin-1-yl), and non-aromatic heterocyclic groups such as pyrrolidinyl (e.g. 1-pyrrolidinyl), piperidinyl (e.g. piperidino), morpholinyl (e.g. morpholino), piperazinyl (e.g. 1-piperazinyl), hexamethyleneiminyl (e.g. hexamethyleneimin-1-yl), oxazolidinyl (e.g. oxazolidin-3-yl), thiazolidinyl (e.g. thiazolidin-3-yl, thiazolidin-2-yl), imidazolidinyl (e.g. imidazolidin-3-yl), imidazolinyl (e.g. imidazolin-1-yl, imidazolin-2-yl), oxazolinyl (e.g. oxazolin-2-yl), thiazolinyl (e.g. thiazolin-2-yl), and oxazinyl (e.g. oxazin-2-yl).

Preferred examples of the heterocyclic group are an azolyl group (e.g. pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl), an azolinyl group (e.g. imidazolinyl, oxazolinyl, thiazolinyl), an azolidinyl group (e.g. pyrrolidinyl, oxazolidinyl, thiazolidinyl, imidazolidinyl).

The heterocyclic group represented by $R^1$ or A may have 1 to 3 substituents at its substitutable positions. The substituents include, for example, an aliphatic hydrocarbon group, an alicyclic hydrocarbon group, an aryl group, an aromatic heterocyclic group, a non-aromatic heterocyclic group, a halogen atom, a nitro group, an optionally substituted amino group, an optionally substituted acyl group, an optionally substituted hydroxy group, an optionally substituted thiol group, an optionally esterified or amidated carboxy group and oxo group.

Examples of an azolidinyl group substituted by 1 or 2 oxo group(s) are 2-oxoimidazolidinyl (e.g. 2-oxoimidazolidin-1-yl), 2,4-dioxoimidazolidinyl (e.g. 2,4-dioxoimidazolidin-3-yl), 2,4-dioxooxazolidinyl (e.g. 2,4-dioxooxazolidin-3-yl) or 2,4-dioxothiazolidinyl (e.g. 2,4-dioxothiazolidin-3-yl).

The aliphatic hydrocarbon group may be a linear or branched aliphatic hydrocarbon group having 1 to 15 carbon atoms such as, for example, an alkyl group, an alkenyl group and an alkynyl group.

Preferred examples of the alkyl group are alkyl groups having 1 to 10 carbon atoms such as, for example, methyl, ethyl, propyl, isopropyl, butyl, isobutyl, sec-butyl, t-butyl, pentyl, isopentyl, neopentyl, t-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl.

Preferred examples of the alkenyl group are alkenyl groups having 2 to 10 carbon atoms such as, for example, vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

Preferred examples of the alkynyl group are alkynyl groups having 2 to 10 carbon atoms such as, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The alicyclic hydrocarbon group may be a saturated or unsaturated alicyclic hydrocarbon group having 3 to 12 carbon atoms such as, for example, a cycloalkyl group, a cycloalkenyl group and a cycloalkadienyl group.

Preferred examples of the cycloalkyl group are cycloalkyl groups having 3 to 10 carbon atoms such as, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl.

Preferred examples of the cycloalkenyl group are cycloalkenyl groups having 3 to 10 carbon atoms such as, for example, 2-cyclopenten-1-yl, 3-cyclopenten-1-yl, 2-cyclohexen-1-yl and 3-cyclohexen-1-yl.

Preferred examples of the cycloalkadienyl group are cycloalkadienyl groups having 4 to 10 carbon atoms such as, for example, 2,4-cyclopentadien-1-yl, 2,4-cyclohexadien-1-yl and 2,5-cyclohexadien-1-yl.

The aryl group stands for a mono-cyclic or condensed poly-cyclic aromatic hydrocarbon group, and preferred examples of them are aryl groups having 6 to 14 carbon atoms such as, for example, phenyl, naphthyl, anthryl, phenanthryl and acenaphthylenyl. More preferable are phenyl, 1-naphthyl and 2-naphthyl.

Preferred examples of the aromatic heterocyclic group include an aromatic mono-cyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and an aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

Preferred examples of the non-aromatic heterocyclic group include oxiranyl, azetidinyl, oxetanyl, thietanyl, tetrahydrofuryl, thioranyl, piperidyl, tetrahydropyranyl, morpholinyl, thiomorpholinyl, piperazinyl and pyrrolidinyl.

Examples of the halogen atom include fluorine, chlorine, bromine and iodine. More preferably are fluorine and bromine.

The optionally substituted amino group may be an amino group (—NH$_2$) which may be mono- or di-substituted with, for example, an alkyl group having 1 to 10 carbon atoms, an alkenyl group having 2 to 10 carbon atoms, a cycloalkyl group having 3 to 10 carbon atoms, an acyl group having 1 to 10 carbon atoms (e.g. formyl, $C_{1-9}$ alkyl-carbonyl such as acetyl) or an aromatic group having 6 to 12 carbon atoms (e.g. $C_{6-12}$ aryl such as phenyl). The substituted amino group includes, for example, methylamino, dimethylamino, ethylamino, diethylamino, dibutylamino, diallylamino, cyclohexylamino, acetylamino, propionylamino, benzoylamino, phenylamino and N-methyl-N-phenylamino.

The acyl moiety of the optionally substituted acyl group may be an acyl group having 1 to 13 carbon atoms, including, for example, a formyl group, and a group to be formed by bonding between an alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms or an aromatic group from 6 to 12 carbon atoms and a carbonyl group (e.g., $C_{1-10}$ alkyl-carbonyl such as acetyl, propionyl, butyryl, isobutyryl, valeryl, isovaleryl, pivaloyl, hexanoyl, heptanoyl, octanoyl; $C_{3-10}$ cycloalkyl-carbonyl such as cyclobutanecarbonyl, cyclopentanecarbonyl, cyclohexanecarbonyl, cycloheptanecarbonyl; $C_{2-10}$ alkenyl-carbonyl such as crotonyl; $C_{3-10}$ cycloalkenyl-carbonyl such as 2-cyclohexenecarbonyl; $C_{6-10}$ aryl-carbonyl such as benzoyl, nicotinoyl). The substituent of the substituted acyl group may include, for example, an alkyl group having 1 to 3 carbon atoms, an alkoxy group having 1 to 3 carbon atoms, a halogen atom (e.g., chlorine, fluorine, bromine), a nitro group, a hydroxy group and an amino group.

The substituted hydroxy group of the optionally substituted hydroxy group includes, for example, an alkoxy group, an alkenyloxy group, an aralkyloxy group, an acyloxy group, an aryloxy group, an alkylsulfonyloxy group and an arylsulfonyloxy group.

Preferred examples of the alkoxy group are alkoxy groups having 1 to 10 carbon atoms such as, for example, methoxy, ethoxy, propoxy, isopropoxy, butoxy, isobutoxy, sec-butoxy, t-butoxy, pentyloxy, isopentyloxy, neopentyloxy, hexyloxy, heptyloxy, nonyloxy, cyclobutoxy, cyclopentyloxy and cyclohexyloxy.

Preferred examples of the alkenyloxy group are alkenyloxy groups having 2 to 10 carbon atoms such as, for example, allyloxy, crotyloxy, 2-pentenyloxy, 3-hexenyloxy, 2-cyclopentenylmethoxy and 2-cyclohexenylmethoxy.

Preferred examples of the aralkyloxy group include aralkyloxy groups having 7 to 10 carbon atoms, for example, phenyl-$C_{1-4}$ alkyloxy group (e.g., benzyloxy, phenethyloxy).

Preferred examples of the acyloxy group include acyloxy groups having 2 to 13 carbon atoms, more preferably alkanoyloxy groups having 2 to 4 carbon atoms (e.g., acetyloxy, propionyloxy, butyryloxy, isobutyryloxy).

Preferred examples of the aryloxy group are aryloxy groups having 6 to 14 carbon atoms such as, for example, phenoxy and naphthyloxy. The aryloxy group may have 1 or 2 substituents such as, for example, a halogen atom (e.g., chlorine, fluorine, bromine), or an alkoxy group having 1 to 4 carbon atoms. The substituted aryloxy group includes, for example, 4-chlorophenoxy and 2-methoxyphenoxy.

Preferred examples of the alkylsulfonyloxy group are alkylsulfonyloxy groups having 1 to 10 carbon atoms such as, for example, methylsulfonyloxy and ethylsulfonyloxy.

Preferred examples of the arylsulfonyloxy are arylsulfonyloxy groups having 6 to 12 carbon atoms (which may be substituted by a $C_{1-6}$ alkyl) such as, for example, phenylsulfonyl, 4-methylsulfonyl.

The substituted thiol group (substituted mercapto group) of the optionally substituted thiol group (optionally substituted mercapto group) includes, for example, an alkylthio group, an arylthio group, a heteroarylthio group, an aralkylthio group, a heteroarylalkylthio group and an acylthio group.

Preferred examples of the alkylthio group are alkylthio groups having 1 to 10 carbon atoms such as, for example, methylthio, ethylthio, propylthio, isopropylthio, butylthio, isobutylthio, sec-butylthio, t-butylthio, pentylthio, isopentylthio, neopentylthio, hexylthio, heptylthio, nonylthio, cyclobutylthio, cyclopentylthio, cyclohexylthio.

Preferred examples of the arylthio group are arylthio groups having 6 to 14 carbon atoms which may be substituted by a $C_{1-6}$ alkyl group such as, for example, phenylthio, 4-phenylthio and naphthylthio.

The heteroarylthio group includes, for example, thiol groups substituted by any of the above-mentioned aromatic heterocyclic groups. Preferable examples of them are 2-pyridylthio, 3-pyridylthio, 2-imidazolylthio and 1,2,4-triazol-5-ylthio.

Preferred examples of the aralkylthio group are aralkylthio groups having 7 to 10 carbon atoms such as, for example, phenyl-$C_{1-4}$ alkylthio groups (e.g., benzylthio, phenethylthio).

The heteroarylalkylthio group includes, for example, alkylthio groups substituted by any of the above-mentioned aromatic heterocyclic group. The alkylthio moiety of the heteroarylaklylthio group are the same as the above-mentioned alkylthio group. Preferred examples of the heteroarylalkylthio group include pyridyl-$C_{1-4}$ alkylthio groups (e.g., 2-pyridylmethylthio, 3-pyridylmethylthio).

Preferred examples of the acylthio group are acylthio groups having 2 to 13 carbon atoms, more preferably alkanoylthio groups having 2 to 4 carbon atoms (e.g., acetylthio, propionylthio, butyrylthio, isobutytylthio).

The esterified carboxy group of the optionally esterified or amidated carboxy group includes, for example, an alkoxycarbonyl group, an aralkyloxycarbonyl group, an aryloxycarbonyl group and a heteroarylalkyloxycarbonyl.

Preferred examples of the alkoxycarbonyl group are alkoxycarbonyl groups having 2 to 5 carbon atoms such as, for example, $C_{1-4}$ alkoxy-carbonyl (e.g. methoxycarbonyl, ethoxycarbonyl, propoxycarbonyl and butoxycarbonyl).

Preferred examples of the aralkyloxycarbonyl group are aralkyloxycarbonyl groups having 8 to 10 carbon atoms such as, for example, $C_{7-9}$ aralkyloxy-carbonyl (e.g. benzyloxycarbonyl).

Preferred examples of the aryloxycarbonyl group are aryloxycarbonyl groups having 7 to 15 carbon atoms such as for example, $C_{6-14}$ aryloxy-carbonyl (e.g. phenoxycarbonyl and p-tolyloxycarbonyl).

The heteroarylalkyloxycarbonyl group includes, for example, alkyloxycarbonyl groups substituted with any of the above-mentioned aromatic heterocyclic groups. The alkyloxycarbonyl moiety of the heteroarylalkyloxycarbonyl are the same as the above-mentioned alkoxycarbonyl. Preferred examples of the heteroarylalkyloxycarbonyl group include pyridyl-$C_{1-4}$ alkoxy-carbonyl groups (e.g., 2-pyridylmethoxycarbonyl, 3-pyridylmethoxycarbonyl).

The amidated carboxyl group of the optionally esterified or amidated carboxyl group includes, for example, a group of formula: —CON($R^5$)($R^6$), wherein $R^5$ and $R^6$ may be the same or different and each represents a hydrogen atom, an optionally substituted hydrocarbon group, an optionally substituted hydroxy group or an optionally substituted heterocyclic group. The hydrocarbon groups of the optionally substituted hydrocarbon group represented by $R^5$ or $R^6$ includes, for example, an aliphatic hydrocarbon group, an alicyclic hydrocarbon group and an aryl group, which have been referred to hereinabove as the examples of the substituent for the heterocyclic group of $R^1$ or A. The substituted hydroxy group of the optionally substituted hydroxy group represented by $R^5$ or $R^6$ may be the substituted hydroxy group of $R^1$ or A. The heterocyclic group of the optionally substituted heterocyclic group represented by $R^5$ or $R^6$ may be an aromatic heterocyclic group which is referred to hereinabove as the examples of the substituent for the heterocyclic group of $R^1$ or A. Regarding the substituents of $R^5$ or $R^6$ the group may be substituted by 1 to 3 substituents selected from a halogen atom (e.g., chlorine, fluorine, bromine, iodine), an alkyl group having 1 to 4 carbon atoms and an alkoxy group having 1 to 4 carbon atoms.

In the formula (I), an alicyclic hydrocarbon group, an aryl group, an aromatic heterocyclic group or a non-aromatic heterocyclic group for the substituent on the heterocyclic group may be substituted by one or more, preferably 1 to 3 suitable substituents. Such substituents include, for example, an alkyl group having 1 to 6 carbon atoms, an alkenyl group having 2 to 6 carbon atoms, an alkynyl group having 2 to 6 carbon atoms, a cycloalkyl group having 3 to 7 carbon atoms, an aryl group having 6 to 14 carbon atoms (e.g., phenyl, naphthyl), an aromatic heterocyclic group. (e.g., thienyl, furyl, pyridyl, oxazolyl, thiazolyl), a non-aromatic heterocyclic group (e.g., tetrahydrofuryl, morpholino, piperidino, pyrrolidino, piperazino), an aralkyl group having 7 to 9 carbon atoms (e.g. benzyl), an amino group, an N-mono($C_{1-4}$)alkylamino group, an N,N-di($C_{1-4}$)alkylamino group, an acylamino group having 2 to 8 carbon atoms (e.g., $C_{1-7}$ alkyl-carbonylamino such as acetylamino, propionylamino; benzoylamino), an amidino group, an acyl group having 2 to 8 carbon atoms (e.g., $C_{1-7}$ alkyl-carbonyl such as acetyl, benzoyl), a carbamoyl group, an N-mono($C_{1-4}$) alkylcarbamoyl group, an N,N-di($C_{1-4}$)alkylcarbamoyl group, a sulfamoyl group, an N-mono($C_{1-4}$)alkylsulfamoyl group, an N,N-di($C_{1-4}$)alkylsulfamoyl group, a carboxy group, an alkoxycarbonyl group having 2 to 8 carbon atoms, a hydroxy group, an alkoxy group having 1 to 4 carbon atoms, an alkenyloxy group having 2 to 5 carbon atoms, a cycloalkyloxy group having 3 to 7 carbon atoms, an aralkyloxy group having 7 to 9 carbon atoms (e.g. benzyloxy), an aryloxy group having 6 to 14 carbon atoms (e.g., phenyloxy, naphthyloxy), a mercapto group, an alkylthio group having 1 to 4 carbon atoms, an aralkylthio group having 7 to 9 carbon atoms (e.g. benzylthio), an arylthio group having 6 to 14 carbon atoms (e.g., phenylthio, naphthylthio), a sulfo group, a cyano group, an azido group, a nitro group, a nitroso group and a halogen atom (e.g., fluorine, chlorine, bromine, iodine).

In the formula (I), as the halogen atom, the optionally substituted hydroxy group, the optionally substituted thiol group and the optionally substituted amino group represented by $R^1$, are those that are mentioned hereinabove as the examples of the substituents for the heterocyclic group represented by $R^1$ or A.

In the formula (I), $R^1$ is preferably an optionally substituted heterocyclic group.

In the formula (I), as the optionally substituted acyl group, the optionally substituted hydroxy group, and the optionally esterified or amidated carboxy group represented by A are those that are mentioned hereinabove as the examples of the substituents for the heterocyclic group represented by $R^1$ or A.

In the formula (I), A is preferably an optionally substituted heterocyclic group or an optionally substituted hydroxy group.

In the formula (I), the aromatic group of the optionally substituted aromatic group represented by B includes, for example, an aromatic hydrocarbon group and an aromatic heterocyclic group.

Preferred examples of the aromatic hydrocarbon group are aromatic hydrocarbon groups having 6 to 14 carbon atoms such as for example, $C_{6-14}$ aryl group such as phenyl and naphthyl.

Preferred examples of the aromatic heterocyclic group are those that are mentioned hereinabove as the examples of the substituent for the heterocyclic group represented by $R^1$ or A. More preferable are furyl, thienyl, pyridyl and quinolyl.

Regarding the optionally substituted aromatic group represented by B, it may be substituted by 1 to 3 substituents selected from, for example, a halogen atom, a nitro group, a cyano group, an optionally substituted alkoxy group, an optionally substituted alkyl group and an optionally substituted cycloalkyl group.

The halogen atom includes, for example, fluorine, chlorine, bromine and iodine.

Examples of the alkoxy group of the optionally substituted alkoxy group are those that are mentioned hereinabove as the examples of the substituent for the heterocyclic group represented by $R^1$ or A. More preferable are linear or branched alkoxy groups having 1 to 6 carbon atoms.

Examples of the alkyl group of the optionally substituted alkyl group are those that are mentioned hereinabove as the examples of the substituent for the heterocyclic group represented by $R^1$ or A. More preferable are linear or branched alkyl groups having 1 to 6 carbon atoms.

Examples of the cycloalkyl group of the optionally substituted cycloalkyl group are those that are mentioned hereinabove as the examples of the substituent for the heterocyclic group represented by $R^1$ or A. More preferable are cycloalkyl groups having 3 to 7 carbon atoms.

Regarding the above-mentioned optionally substituted alkoxy, alkyl and cycloalkyl groups, each of these groups may be substituted by 1 to 3 substituents selected from, for example, a halogen atom (e.g., fluorine, chlorine, bromine, iodine), a hydroxy group and an alkoxy group having 1 to 6 carbon atoms.

The substituted alkoxy group includes, for example, trifluoromethoxy, difluoromethoxy, 2,2,2-trifluoroethoxy and 1,1-difluoroethoxy.

The substituted alkyl group includes, for example, trifluoromethyl, difluoromethyl, 2,2,2-trifluoroethyl, trichloromethyl, 1-hydroxymethyl, methoxymethyl, ethoxymethyl, 2-methoxymethyl and 2,2-dimethoxyethyl.

In the formula (I), B is preferably an optionally substituted aromatic hydrocarbon group, and more preferably an optionally substituted phenyl group.

In the formula (I), the divalent aliphatic hydrocarbon group having 1 to 7 carbon atoms represented by Y may be either linear or branched, and may be either saturated or unsaturated. Typical examples of the aliphatic hydrocarbon group include saturated groups such as —$CH_2$—, —CH($CH_3$)—, —$(CH_2)_2$—, —CH($C_2H_5$)—, —$(CH_2)_3$—, —$(CH_2)_4$—, —$(CH_2)_5$—, —$(CH_2)_6$— and —$(CH_2)_7$—, and unsaturated groups such as —CH=CH—, —C($CH_3$)=CH—, —CH=CH—$CH_2$—, —C($C_2H_5$)=CH—, —$CH_2$—CH=CH—$CH_2$—, —$CH_2$—$CH_2$—CH=CH—$CH_2$—, —CH=CH—CH=CH—$CH_2$— and —CH=CH—CH=CH— CH=CH—$CH_2$—. Y is preferably a divalent aliphatic hydrocarbon group having 1 to 4 carbon atoms, and is more preferably the saturated one. Preferred examples of Y are —$(CH_2)_3$— and —$(CH_2)_2$—.

Preferred examples of the compound (I) of this invention are as follows.

(1) In the formula (I), $R^1$ is an optionally substituted heterocyclic group, and a preferred example of the heterocyclic group is a 5- or 6-membered ring having 1 to 4 atoms selected from N, O and S as the ring-constituting atoms other than carbon atom(s), or a condensed ring comprising the 5- or 6-membered ring as condensed with any of a 6-membered ring having 1 or 2 nitrogen, a benzene ring or a 5-membered ring having one sulfur, and a more preferred example of the heterocyclic group is an azolyl group.

(2) In the formula (I), A is an optionally substituted heterocyclic group, preferred example of the heterocyclic group is a 5- or 6-membered ring having 1 to 4 atoms selected from N, O and S as the ring-constituting atoms other than carbon atom(s), or a condensed ring comprising the 5- or 6-membered ring as condensed with a 6-membered ring having 1 or 2 nitrogen, a benzene ring or a 5-membered ring having one sulfur, and more preferred example of the heterocyclic group is an azolyl, azolinyl or azolidinyl group.

(3) In the formula (I), the optionally substituted heterocyclic group represented by $R^1$ and A is a 2-pyridyl, 3-pyridyl, 4-pyridyl, 2-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-5-yl, 1,2,4-triazol-1-yl, 1,2,4-triazol-3-yl, 1,2,3-triazol-2-yl, 1,2,3-triazol-4-yl, tetrazol-1-yl, tetrazol-5-yl, benzimidazol-1-yl, benzimidazol-2-yl, indol-1-yl, indol-3-yl, 1H-indazol-1-yl, 1H-pyrrolo[2,3-b]pyrazin-1-yl, 1H-pyrrolo[2,3-b]pyridin-1-yl, 1H-imidazo[4,5-b]pyridin-1-yl, 1H-imidazo[4,5-c]pyridin-1-yl, 1H-imidazo[4,5-b]pyrazin-1-yl, 1-pyrrolidinyl, piperidino, morpholino, 1-piperazinyl, hexamethyleneimin-1-yl, oxazolidin-3-yl, thiazolidin-3-yl, imidazolidin-3-yl, imidazolin-1-yl, imidazolin-2-yl, oxazolin-2-yl, thiazolin-2-yl, oxazin-2-yl, 2-oxoimidazolidin-1-yl, 2,4-dioxoimidazolidin-3-yl, 2,4-dioxooxazolidin-3-yl or 2,4-dioxothiazolidin-3-yl group which may be substituted by 1 to 3 substituents selected from the group consisting of an aliphatic hydrocarbon group, an alicyclic hydrocarbon group, an aryl group, an aromatic heterocyclic group, a non-aromatic heterocyclic group, a halogen atom, a nitro group, an optionally substituted amino group, an optionally substituted acyl group, an optionally substituted hydroxy group, an optionally substituted thiol group and an optionally esterified or amidated carboxy group.

(4) In the formula (I), A is an optionally substituted hydroxy group.

(5) In the formula (I), Y is a divalent aliphatic hydrocarbon group having 1 to 7 carbon atoms, and more preferable a divalent aliphatic hydrocarbon group having 2 to 4 carbon atoms.

(6) In the formula (I), $R^1$ is (i) halogen, (ii) a imidazolyl, pyrazolyl, 1,2,4-triazolyl, 1,2,3-triazolyl, benzimidazolyl, pyrrolidinyl, piperidinyl, morphorinyl or hexamethyleneiminyl group which may be substituted by 1 to 3 substituents selected from the group consisting of $C_{1-10}$ alkyl, $C_{6-14}$ aryl and $C_{1-10}$ alkylthio, (iii) a $C_{1-10}$ alkoxy group, (iv) a $C_{6-14}$ aryloxy group, (v) a $C_{1-10}$ alkylthio group, (vi) a $C_{6-14}$ arylthio which may be substituted by a $C_{1-6}$ alkyl, (vii) a thiol group substituted by an imidazolyl, 1,2,3-triazolyl, 1,2,4-triazolyl or pyridyl group which may be substituted by a $C_{1-6}$ alkyl or $C_{6-14}$ aryl, (viii) a pyridyl-$C_{1-4}$ alkylthio group, or (ix) an amino group which may be substituted by 1 or 2 $C_{1-10}$ alkyl or $C_{3-10}$ cycloalkyl;

A is (i) formyl group, (ii) an imidazolyl, pyrazolyl, 1,2,4-triazolyl, 1,2,3-triazolyl, thiazolidinyl, oxazolinyl, thiazolinyl, 2,4-dioxoimidazolidinyl, 2,4-dioxooxazolidinyl or 2,4-dioxothiazolidinyl group which may be substituted by a $C_{1-10}$ alkyl group, (iii) hydroxy group, (iv) a $C_{6-14}$ aryloxy group which may be substituted by a $C_{1-4}$ alkoxy group, (v) a $C_{1-10}$ alkylsulfonyloxy group, (vi) a $C_{1-4}$ alkoxy-carbonyl group, (vii) a $C_{7-9}$ aralkyloxy-carbonyl group, or (viii) a group of the formula: —CON($R^5$)($R^6$), wherein $R^5$ and $R^6$ are independently hydrogen atom, $C_{1-10}$ alkyl which may be substituted by a halogen atom or a $C_{1-10}$ alkoxy group;

B is a phenyl group which may be substituted by a halogen; Y is —(CH$_2$)$_2$—, —(CH$_2$)$_3$—, —(CH$_2$)$_4$—, —(CH$_2$)$_5$— or —(CH$_2$)$_6$—.

(7) In the formula (I), $R^1$ is an optionally substituted heterocyclic group; A is an optionally substituted heterocyclic group; and Y is a divalent aliphatic hydrocarbon group having 1 to 7 carbon atoms.

(8) In the above-mentioned (7), the heterocyclic group represented by $R^1$ and A is an azolyl group, an azolinyl group or an azolidinyl group.

(9) In the above-mentioned (7), the heterocyclic group represented by $R^1$ is an azolyl group, and the heterocyclic group represented by A is an azolyl group, an azolinyl group or an azolidinyl group.

(10) In the above-mentioned (7), $R^1$ and A are independently a pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl, pyrrolidinyl, oxazolidinyl, thiazolidinyl, imidazolidinyl, imidazolinyl, oxazolinyl or thiazolinyl group which may be substituted by 1 to 3 substituents selected from the group consisting of $C_{1-10}$ alkyl, $C_{6-14}$ aryl, $C_{1-10}$ alkylthio and oxo.

(11) In the above-mentioned (7), $R^1$ is an azolyl group which may be substituted by 1 to 3 substituents selected from the group consisting of $C_{1-10}$ alkyl, $C_{6-14}$ aryl and $C_{1-10}$ alkylthio.

(12) In the above-mentioned (11), the azolyl group is an imidazolyl, pyrazolyl, 1,2,4-triazolyl, or 1,2,3-triazolyl group.

(13) In the above-mentioned (7), A is an azolyl, azolinyl or azolidinyl group which may be substituted by 1 or 2 $C_{1-10}$ alkyl or oxo.

(14) In the above-mentioned (7), A is an imidazolyl, pyrazolyl, 1,2,4-triazolyl, 1,2,3-triazolyl, thiazolidinyl, oxazolinyl, thiazolinyl, 2,4-dioxoimidazolidinyl, 2,4-dioxooxazolidinyl or 2,4-dioxothiazolidinyl group which may be substituted by a $C_{1-10}$ alkyl group.

(15) In the above-mentioned (7), B is an optionally substituted phenyl group.

(16) In the above-mentioned (7), B is a phenyl group which may be substituted by a halogen atom.

(17) In the above-mentioned (7), Y is a divalent aliphatic hydrocarbon group having 3 to 5 carbon atoms.

(18) In the above-mentioned (7), Y is —(CH$_2$)$_3$—, —(CH$_2$)$_4$— or —(CH$_2$)$_5$—.

(19) In the formula (I), $R^1$ is an optionally substituted heterocyclic group; A is an optionally substituted hydroxy group; and Y is a divalent aliphatic hydrocarbon group having 1 to 7 carbon atoms.

(20) In the above-mentioned (19), the heterocyclic group represented by $R^1$ is an azolyl group.

(21) In the above-mentioned (20), the azoyl group is a pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl or tetrazolyl group.

(22) In the above-mentioned (19), $R^1$ is an azolyl group which may be substituted by 1 to 3 substituents selected from the group consisting of $C_{1-10}$ alkyl, $C_{6-14}$ aryl and $C_{1-10}$ alkylthio.

(23) In the above-mentioned (22), the azolyl group is an imidazolyl, pyrazolyl, 1,2,4-triazolyl or 1,2,3-triazolyl group.

(24) In the above-mentioned (19), A is (i) a hydroxy group, (ii) a $C_{1-10}$ alkoxy group, (iii) a $C_{2-10}$ alkenyloxy group, (iv) a $C_{7-10}$ aralkyloxy group, (v) a $C_{2-13}$ acyloxy group, (vi) a $C_{6-14}$ aryloxy group which may be substituted by 1 or 2 halogen or $C_{1-4}$ alkoxy, or (vii) $C_{1-10}$ alkylsulfonyloxy group, and more preferably a hydroxy group.

(25) In the above-mentioned (19), B is an optionally substituted phenyl group, and more preferably a phenyl group which may be substituted by a halogen.

(26) In the above-mentioned (19), Y is a divalent aliphatic hydrocarbon group having 3 to 5 carbon atoms, and more preferably —(CH$_2$)$_3$—, —(CH$_2$)4— or —(CH$_2$)$_5$—.

(27) In the formula (I), 4-(4-chlorophenyl)-2-(2-methyl-1-imidazolyl)-5-oxazolepropanol or its salt, 4-(4-chlorophenyl)-2-(2-methyl-1-imidazolyl)-5-oxazolebutanol or its salt, 4-(4-chlorophenyl)-5-[3-(1-imidazolyl)propyl]-2-(2-methyl-1-imidazolyl)oxazole or its salt, 4-(4-chlorophenyl)-2-(2-methyl-1-imidazolyl)-5-oxazolepentanol or its salt, or 4-(4-chlorophenyl)-5-[4-(1-imidazolyl)butyl]-2-(2-methyl-1-imidazolyl)oxazole or its salt.

As the salts of compounds (I) of the present invention, preferred are pharmaceutically acceptable salts thereof, which include, for example, salts with inorganic bases, salts with organic bases, salts with inorganic acids, salts with organic acids and salts with basic or acidic amino acids. Preferred examples of the salts with inorganic bases include alkali metal salts such as sodium salts and potassium salts; alkaline earth metal salts such as calcium salts and magnesium salts; and also aluminum salts and ammonium salts. Preferred examples of the salts with organic bases include salts with trimethylamine, triethylamine, pyridine, picoline, ethanolamine, diethanolamine, triethanolamine, dicyclohexylamine or N,N'-dibenzylethylenediamine. Preferred examples of the salts with inorganic acids include salts with hydrochloric acid, hydrobromic acid, nitric acid, sulfuric acid or phosphoric acid. Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid. Preferred examples of the salts with basic amino acids include salts with arginine, lysine or ornithine; and preferred examples of the salts with acidic amino acids include salts with aspartic acid or glutamic acid. Of those salts, the most preferred are sodium salts and potassium salts.

The compounds (I) or their salts of the present invention may also be in the form of hydrates thereof.

The compounds (I) or their pharmaceutically acceptable salts of the present invention (hereinafter referred to as the compounds of the present invention) have a blood sugar lowering effect and an insulin secretion-promoting effect.

The compounds of the present invention can be used, either directly or after having been mixed with any of per-se known, pharmaceutically acceptable carriers, excipients, vehicles and others, as insulin secretion-promoting agents, agents for diabetes, agents for arteriosclerosis, antihyperlipemia, antihypertensive agents, and agents for diabetic complications (e.g., nephropathy, retinopathy, neuropathy), which are applicable to mammals (e.g., humans, mice, rats, rabbits, dogs, cats, bovines, horses, pigs, monkeys).

The compounds of the present invention are of low toxicity. For example, when the compound as obtained in Example 36, as described hereinafter, was orally administered to mice in an amount of 1 g/kg/day, there was no mortality at 5 days.

The compounds of the present invention are orally administered in any form of, for example, tablets, capsules (including soft capsules and microcapsules), powders and granules. As the case may be, however, they may also be parenterally administered for example, as injections, suppositories or pellets. The dose of the compounds of the present invention varies depending on the objects to which they are administered, the administration routes to be employed, and the conditions to which they are directed to. For example, when they are orally administered to adults, the dose thereof may be desirably from 1 to 500 mg/kg/day, preferably from 10 to 150 mg/kg/day, and it may be administered by dividing into 1 to 3 portions.

The pharmaceutical composition of the present invention can be produced by blending the compound of the invention with pharmaceutically acceptable carriers. The pharmaceutical composition may be produced according to any conventional means that are known in the field of formulations. The pharmaceutical composition may be in any form of solid preparations such as tablets, capsules, granules or powders, or liquid preparations such as syrups or injections. These can be administered to mammals such as those mentioned hereinabove, either orally or parenterally.

The pharmaceutical composition of the present invention can be used in insulin secretion-promoting agents, agents for diabetes, agents for arteriosclerosis, antihyperlipemia, antihypertensive agents, and agents for diabetic complications (e.g., nephropathy, retinopathy, neuropathy), and is used especially preferably in insulin secretion-promoting agents and agents for diabetes.

And the compound (I) of the present invention can be given, to the same object, agents for diabetes, agents for diabetic complications, antihyperlipemia or antihypertensive agents at the same time or time lag.

Examples of the agents for diabetes are insulin sensitivity-increasing agents (e.g. pioglitazone, troglitazone, BRL-49653, etc.), α-glucosidase inhibitor (e.g. voglibose, acarbose, miglitol, etc.) and so on. Examples of the agents for diabetic complications are aldose reductase inhibitor (e.g. tolrestat, epalrestat, zenarestat, etc.) and so on. Examples of the antihyperlipemia are statins such as cholesterol-biosynthesis inhibitor (e.g. pravastatin, simvastatin, lovastatin, cerivastatin, etc.), squalene synthetase inhibitor or fibrates having triglyceride lowering effect (e.g. bezafibrate, etc.). Examples of the antihypertensive agents are angiotensin converting enzyme inhibitor (e.g. captopril, enalapril, delapril, etc.), angiotensin II antagonist (e.g. losartan, candesartan, cilexetil, etc.) and so on.

The pharmaceutically acceptable carriers include various conventional, organic or inorganic carrier substances that are commonly used for formulation matter. For example, for solid preparations, employable carriers are excipients, lubricants, binders and disintegrators; and for liquid preparations, employable carriers are solvents, dissolution aids, suspending agents, isotonizing agents, buffers and analgesics. If desired, further employable carriers are any other pharmaceutical additives such as preservatives, antioxidants, colorants and sweeteners.

Preferred examples of excipients include lactose, white sugar, D-mannitol, starch, crystalline cellulose and light silicic acid anhydride.

Preferred examples of lubricants include magnesium stearate, calcium stearate, talc and colloidal silica.

Preferred examples of binders include crystalline cellulose, white sugar, D-mannitol, trehalose, dextrin, hydroxypropyl cellulose, hydroxypropylmethyl cellulose and polyvinyl pyrrolidone.

Preferred examples of disintegrators include starch, carboxymethyl cellulose, calcium carboxymethyl cellulose, sodium cross-carmellose and sodium carboxymethyl starch.

Preferred examples of solvents are water for injection, alcohol, propylene glycol, macrogol, sesame oil, corn oil and tricaprylin.

Preferred examples of dissolution aids include polyethylene glycol, propylene glycol, D-mannitol, trehalose, benzyl benzoate, ethanol, trisaminomethane, cholesterol, triethanolamine, sodium carbonate and sodium citrate.

Preferred examples of suspending agents include surfactants such as stearyltriethanolamine, sodium laurylsulfate, laurylaminopropionic acid, lecithin, benzalkonium chloride, benzethonium chloride and glycerol monostearate; and also hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose.

Preferred examples of isotonizing agents include sodium chloride, glycerin and D-mannitol.

Preferred examples of buffers include those of phosphates, acetates, carbonates or citrates.

A preferred example of analgesics is benzyl alcohol.

Preferred examples of preservatives include parahydroxybenzoates, chlorobutanol, benzyl alcohol, phenethyl alcohol, dehydroacetic acid and sorbic acid.

Preferred examples of antioxidants include sulfites, and ascorbic acid.

The compounds (I) of the present invention can be produced by per-se known methods. For example, the compounds (I) of the invention can be produced by the methods mentioned hereinafter or according to these, or by the methods described in EP-92239 and JP59-190979 or according to those methods.

In the formula (I), a compound represented by the formula (I-a):

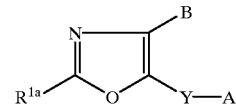

wherein $R^{1a}$ is a halogen atom, and the other symbols are of the same meanings as defined above, or a salt thereof can be produced by reacting a compound represented by the formula:

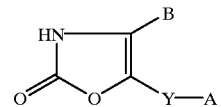

wherein all symbols are of the same meanings as defined above, or a salt thereof with a halogenating agent, and a compound represented by the formula (I-b):

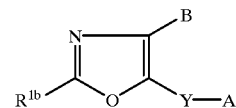

wherein $R^{1b}$ is an optionally substituted heterocyclic group, an optionally substituted hydroxy group, an optionally substituted thiol group or an optionally substituted amino group, corresponding to $R^1$, and the other symbols are of the same meanings as defined above, or a salt thereof can be produced by reacting a compound (I-a) or a salt thereof with a compound represented by the formula:

$$R^{1b}-H$$

wherein all symbols are of the same meanings as defined above, or a salt thereof.

Method A:

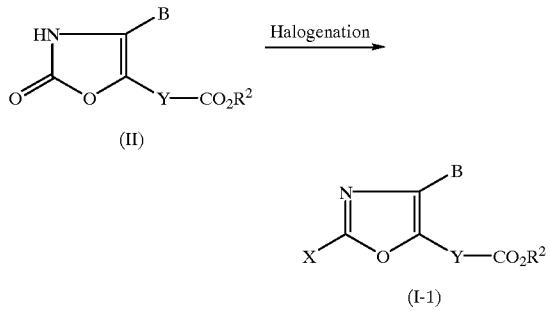

(II)

(I-1)

wherein $R^2$ represents an alkyl group having 1 to 5 carbon atoms; X represents a halogen atom; and the others are of the same meanings as mentioned above.

The alkyl group having 1 to 5 carbon atoms, represented by $R^2$ may include those having 1 to 5 carbon atoms of the examples of the alkyl group as referred to herein above for the substituent for the heterocyclic group of $R^1$ or A.

The halogen atom represented by X includes, for example, chlorine, fluorine and bromine.

Compounds (I-1) which correspond to compounds (I) where $R^1$ is a halogen atom and A is an esterified carboxyl group, can be produced, for example, by halogenation of compounds (II). This reaction may be conducted generally in the presence of a halogenating agent in a solvent that does not have any influence on the reaction. If desired, an excess amount of such a halogenating agent can be used for the solvent to effect the reaction.

The halogenating agent includes, for example, phosphorus oxychloride, phosphorus trichloride, phosphorus pentachloride, thionyl chloride and phosphorus tribromide. The amount of the halogenating agent to be used may be from 1 to 10 molar equivalents, preferably from 3 to 6 molar equivalents, relative to the compound (II).

The solvent that does not have any influence on the reaction includes, for example, aromatic hydrocarbons such as benzene, toluene and xylene; pyridine; and mixed solvents of these.

The reaction temperature ranges generally from 20 to 180° C., preferably from 50 to 130° C. The reaction time ranges from 0.5 to 20 hours.

The compounds (I-1) thus produced may be isolated and purified through any ordinary separating and isolating means, for example, through concentration, concentration under reduced pressure, solvent extraction, precipitation, recrystallization, phasic transfer, chromatography or the like.

Method B:

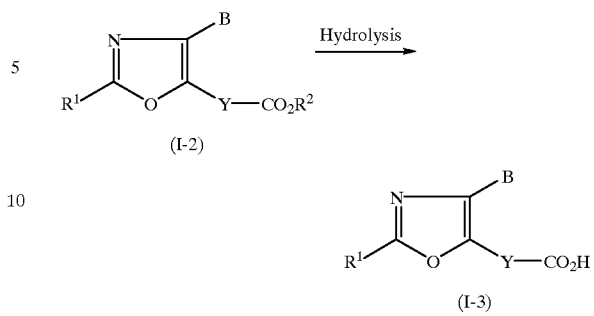

(I-2)

(I-3)

wherein all symbols are of the same meanings as mentioned above.

Compounds (I-3) which correspond to compounds (I) where A is a carboxyl group, can be produced, for example, by hydrolysis of compounds (I-2). This reaction may be conducted in any ordinary manner, for example, in the presence of a base or an acid in an aqueous solvent.

The aqueous solvent may be a mixed solvent comprising water and any of alcohols (methanol and ethanol), ethers (e.g. tetrahydrofuran and dioxane), dimethylsulfoxide and acetone.

The acid includes, for example, hydrochloric acid, sulfuric acid, acetic acid and hydrobromic acid. The base includes, for example, potassium carbonate, sodium carbonate, sodium methoxide, potassium hydroxide, sodium hydroxide and lithium hydroxide. It is desirable that the acid or base to be used is excess over the compound (I-2) (for example, from about 1.2 to about 5 equivalents of the base, or from about 2 to about 50 equivalents of the acid).

The reaction temperature ranges generally from −20° C. to 150° C., preferably from −10° C. to 100° C. The reaction time ranges from 0.1 to 20 hours.

The compounds (I-3) thus produced may be isolated and purified through any ordinary separating and isolating means such as concentration, concentration under reduced pressure, solvent extraction, precipitation, recrystallization, phasic transfer, chromatography or the like.

Method C:

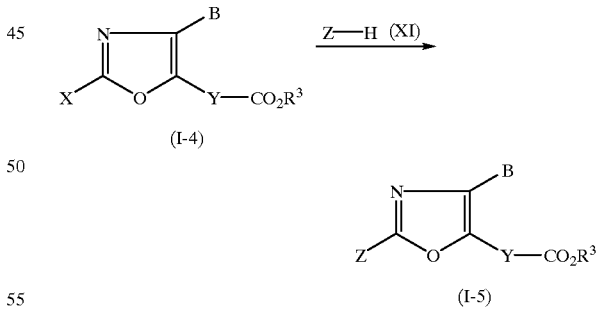

(I-4)

(I-5)

wherein $R^3$ represents a hydrogen atom or an alkyl group having 1 to 5 carbon atoms; Z represents an optionally substituted heterocyclic, hydroxy, thiol or amino group; and the other symbols are of the same meanings as mentioned above.

The alkyl group having 1 to 5 carbon atoms, represented by $R^3$ may include those having 1 to 5 carbon atoms as referred to hereinabove for the examples of the alkyl group to be the substituent for the heterocyclic group of $R^1$ or A.

The optionally substituted heterocyclic, hydroxy, thiol or amino group which are represented by Z may include those as referred to hereinabove for the optionally substituted heterocyclic, hydroxy, thiol or amino group of $R^1$.

Compounds (I-5) which correspond to compounds (I) where $R^1$ is an optionally substituted heterocyclic, hydroxy, thiol or amino group, and A is an optionally esterified carboxy group, can be produced, for example, by reacting a compound (I-4) with a compound (XI). This reaction may be effected generally in the presence of a base in a solvent that does not have any influence on the reaction. Where Z is an optionally substituted amino group in the compound (XI), an excess amount of said compound (XI) can be used as the solvent.

The solvent that does not have any influence on the reaction includes, for example, alcohols such as methanol and ethanol; ethers such as tetrahydrofuran and dioxane; N,N-dimethylformamide, dimethylsulfoxide, acetone, water; and mixed solvents of these.

The base includes, for example, alkali metal salts such as potassium hydroxide, sodium hydroxide, lithium hydroxide, potassium carbonate, sodium carbonate and sodium hydrogencarbonate; metal hydrides such as sodium hydride; sodium ethoxide, and sodium methoxide.

The amount of the compound (XI) to be used may be generally from about 1 to about 10 molar equivalents relative to the compound (I-4). Where Z is an optionally substituted amino group in the compound (XI), the amount of the compound (XI) to be used may be generally from about 1 to about 50 molar equivalents relative to the compound (I-4).

The reaction temperature ranges generally from 20 to 180° C., preferably from 80 to 140° C. The reaction time ranges from 0.5 to 20 hours.

The compounds (I-5) thus produced may be isolated and purified through any ordinary separating and isolating means such as concentration, concentration under reduced pressure, solvent extraction, precipitation, recrystallization, phasic transfer, chromatography or the like.

Method D:

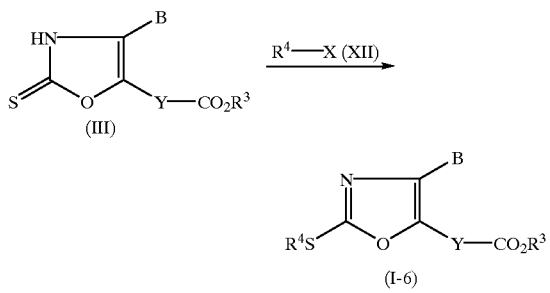

wherein $R^4$ represents an alkyl, aralkyl, heteroarylalkyl or acyl group; and the other symbols are of the same meanings as those mentioned above.

The alkyl, aralkyl, heteroarylalkyl or acyl group represented by $R^4$, include the alkyl, aralkyl, heteroarylalkyl or acyl group of the alkylthio, aralkylthio, heteroarylalkylthio or acyl group that has been mentioned hereinabove for the optionally substituted thiol group of $R^1$.

Compounds (I-6) which correspond to compounds (I) where $R^1$ is a substituted thiol group, and A is an optionally esterified carboxy group, can be produced, for example, by reacting a compound (III) with a compound (XII). This reaction may be conducted in the presence of a base in a solvent that does not have any influence on the reaction.

The base includes, for example, alkali metal salts such as potassium hydroxide, sodium hydroxide, lithium hydroxide, potassium carbonate, sodium carbonate and sodium hydrogencarbonate; metal hydrides such as sodium hydride; sodium methoxide, and sodium ethoxide.

The solvent that does not have any influence on the reaction includes, for example, ethers such as tetrahydrofuran and dioxane; aromatic hydrocarbons such as toluene and xylene; N,N-dimethylformamide, dimethylsulfoxide, acetone, water; and mixed solvents of these.

The amount of the compound (XII) to be used may be from about 1 to about 10 molar equivalents relative to the compound (III).

The reaction temperature ranges generally from -20° C. to 150° C., preferably from about 0 to about 100° C. The reaction time ranges from 0.1 to 20 hours.

The compounds (I-6) thus produced may be isolated and purified through any ordinary separating and isolating means such as concentration, concentration under reduced pressure,.solvent extraction, precipitation, recrystallization, phasic transfer, chromatography or the like.

Method E:

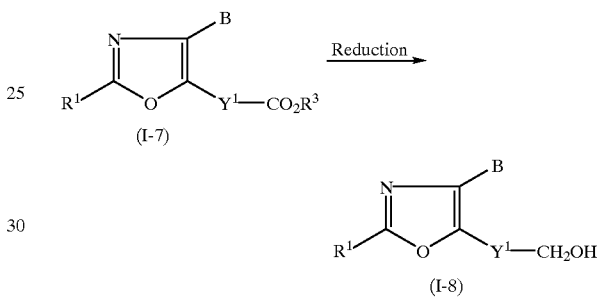

wherein $Y^1$ represents a divalent aliphatic hydrocarbon group; and the other symbols are of the same meanings as those mentioned above.

$Y^1$—$CH_2$ represents a divalent aliphatic hydrocarbon group represented by the above-mentioned Y.

Compounds (I-8) which correspond to compounds (I) where A is a hydroxyl group, can be produced, for example, by reduction of compounds (I-7). This reaction may be conducted in any per-se known manner. Generally using a reducing agent, the reduction may be conducted in a solvent that does not have any influence on the reaction.

The reducing agent to be used includes, for example, metal hydrides such as alkali metal borohydrides (e.g., sodium borohydride, lithium borohydride), metal-hydrogen complexes (e.g. lithium aluminium hydride), organic tin compounds (e.g. triphenyl tin hydride), diborane, and substituted boranes.

The solvent that does not have any influence on the reaction includes, for example, aromatic hydrocarbons such as benzene, toluene and xylene; halogenated hydrocarbons such as chloroform, dichloromethane and carbon tetrachloride; ethers such as tetrahydrofuran and dioxane; alcohols such as methanol and ethanol; N,N-dimethylformamide; and mixed solvents of these. These solvents may be suitably selected, depending on the type of the reducing agent used.

The reaction temperature ranges generally from -20° C. to 150° C., preferably from about 0 to about 100° C. The reaction time ranges from 0.1 to 10 hours. The compounds (I-8) thus produced may be isolated and purified through any ordinary separating and isolating means such as concentration, concentration under reduced pressure, solvent extraction, precipitation, recrystallization, phasic transfer, chromatography or the like.

Method F:

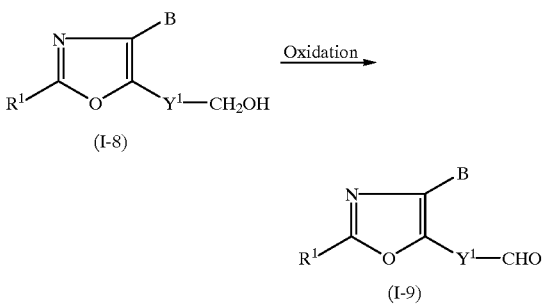

wherein all symbols are of the same meanings as those mentioned above.

Compounds (I-9) which correspond to compounds (I) where A is a formyl group, can be produced, for example, by oxidation of compounds (I-8). This reaction may be conducted in any per-se known manner. The oxidation may be effected, for example, with manganese dioxide, chromic acid, dimethylsulfoxide or the like.

Where the oxidation is conducted with dimethylsulfoxide, the reaction may be conducted in the presence of an electrophilic reagent in a solvent that does not have any influence on the reaction.

The electrophilic reagent includes, for example, acetic anhydride, phosphoric anhydride, oxalyl chloride, dicyclohexylcarbodiimide and chlorine. The amount of the electrophilic reagent to be used may be generally an equimolar amount relative to dimethylsulfoxide.

The solvent that does not have any influence on the reaction includes, for example, halogenated hydrocarbons such as chloroform and dichloromethane; and aromatic hydrocarbons such as benzene, and toluene.

The amount of dimethylsulfoxide to be used may be from 1 to 5 molar equivalents, preferably from 1 to 2 molar equivalents, relative to the compound (I-8).

The reaction temperature ranges generally from −20° C. to 100° C., preferably from about 0 to about 60° C. The reaction time ranges from 0.5 to 20 hours.

The compounds (I-9) thus produced may be isolated and purified through any ordinary separating and isolating means such as concentration, concentration under reduced pressure, solvent extraction, precipitation, recrystallization, phasic transfer chromatography or the like.

Method G:

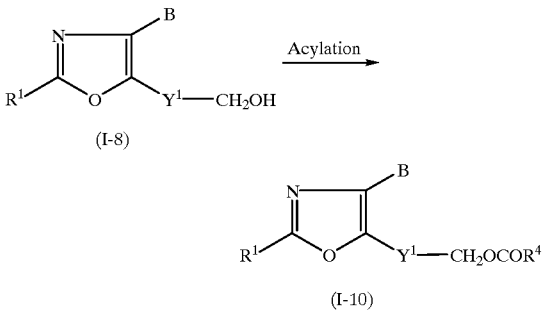

wherein all symbols are of the same meanings as those mentioned above.

Compounds (I-10) which correspond to compounds (I) where A is a substituted hydroxy group, can be produced, for example, by acylation of compounds (I-8). This reaction may be conducted in any per-se known manner. The acylation may be effected, for example, according to a method of directly condensing the compound (I-8) with a carboxylic acid derivative ($R^4CO_2H$), using a dehydrating agent (e.g., dicyclohexylcarbodiimide), or according to a method of suitably reacting the compound (I-8) with a reactive derivative of such a carboxylic acid derivative ($R^4CO_2H$). The reactive derivative of a carboxylic acid derivative ($R^4CO_2H$) includes, for example, acid anhydrides, acid halides (e.g., acid chlorides, acid bromides), imidazolides, and mixed acid anhydrides (e.g., anhydrides with methyl carbonate, ethyl carbonate or isobutyl carbonate).

Of these, the most simple method is to use such an acid chloride or acid anhydride, in which the intended reaction is conducted in the presence of a base in a solvent that does not have any influence on the reaction.

The base includes, for example, triethylamine, N-methylmorpholine, N,N-dimethylaniline, sodium hydrogencarbonate, potassium carbonate and sodium carbonate.

The solvent that does not have any influence on the reaction includes, for example, halogenated hydrocarbons such as chloroform and dichloromethane; aromatic hydrocarbons such as benzene and toluene; ethyl acetate; and tetrahydrofuran.

The amount of the acid chloride or acid anhydride to be used may be from about 1 to about 5 molar equivalents relative to the compound (I-8).

The reaction temperature ranges from about −30° C. to about 100° C. The reaction time ranges from 0.5 to 20 hours.

The compounds (I-10) thus produced may be isolated and purified through any ordinary separating and isolating means such as concentration, concentration under reduced pressure, solvent extraction, precipitation, recrystallization, phasic transfer, chromatography or the like.

Method H:

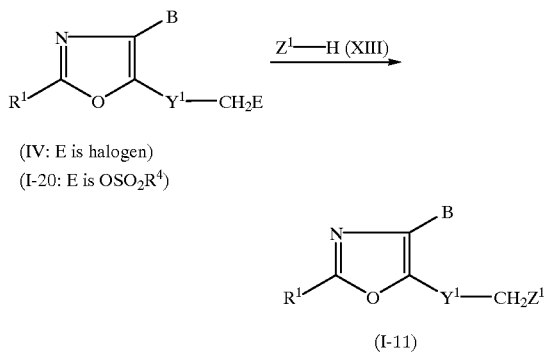

(IV: E is halogen)
(I-20: E is $OSO_2R^4$)

wherein E represents a halogen atom or $OSO_2R^4$; $Z^1$ represents an optionally substituted heterocyclic or hydroxy group; and the other symbols are of the same meanings as those mentioned above.

The halogen atom represented by E includes, for example, chlorine, fluorine and bromine atoms.

The optionally substituted heterocyclic or hydroxy group represented by $Z^1$ may include the examples of the optionally substituted heterocyclic or hydroxy group as referred to hereinabove for $R^1$.

Compounds (I-11) which correspond to the compounds (I) where A is an optionally substituted heterocyclic or hydroxy group, can be produced, for example, by condensation of a compound (IV or I-20) with a compound (XIII). This reaction may be conducted in any ordinary manner, in the presence of a base in a solvent that does not have any influence on the reaction.

The base includes, for example, alkali metal salts such as potassium hydroxide, sodium hydroxide, sodium hydrogencarbonate and potassium carbonate; amines such as pyridine, triethylamine and N,N-dimethylaniline; metal hydrides such as potassium hydride and sodium hydride; sodium methoxide, sodium ethoxide, and potassium t-butoxide. The amount of the base to be used may be preferably from 1 to 5 molar equivalents relative to the compound (IV or I-20).

The solvent that does not have any influence on the reaction includes, for example, aromatic hydrocarbons such as benzene, toluene and xylene; ethers such as tetrahydrofuran and dioxane; ketones such as acetone and 2-butanone; halogenated hydrocarbons such as chloroform and dichloromethane; N,N-dimethylformamide, dimethylsulfoxide; and mixed solvents of these.

The reaction temperature ranges generally from −50° C. to 150° C., preferably from about −10° C. to about 100° C. The reaction time ranges from 0.5 to 20 hours.

The compounds (I-11) thus produced may be isolated and purified through any ordinary separating and isolating means such as concentration, concentration under reduced pressure, solvent extraction, precipitation, recrystallization, phasic transfer, chromatography or the like.

Method I:

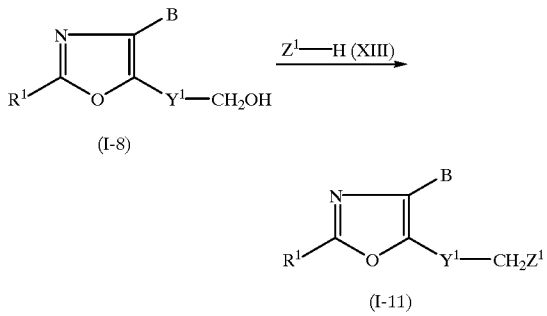

wherein all symbols are of the same meanings as those mentioned above.

Compounds (I-11) which correspond to the compounds (I) where A is an optionally substituted heterocyclic or hydroxy group, can be produced, for example, by condensation of a compound (I-8) with a compound (XIII). This reaction may be conducted in any ordinary manner, in the presence of an organic phosphorus compound and an electrophilic reagent in a solvent that does not have any influence on the reaction.

The organic phosphorus compound includes, for example, triphenylphosphine and tributylphosphine. The electrophilic reagent includes, for example, diethyl azodicarboxylate, diisopropyl azodicarboxylate and azodicarbonylpiperazine. The amount of the organic phosphorus compound and that of the electrophilic reagent may be preferably from 1 to 5 molar equivalents each, relative to the compound (I-8).

The solvent that does not have any influence on the reaction includes, for example, ethers such as diethyl ether, tetrahydrofuran and dioxane; halogenated hydrocarbons such as chloroform and dichloromethane; aromatic hydrocarbons such as benzene, toluene and xylene; N,N-dimethylformamide, dimethylsulfoxide; and mixed solvents of these.

The reaction temperature ranges generally from −50° C. to 150° C., preferably from about −10° C. to about 100° C. The reaction time ranges from 0.5 to 20 hours.

The compounds (I-11) thus produced may be isolated and purified through any ordinary separating and isolating means such as concentration, concentration under reduced pressure, solvent extraction, precipitation, recrystallization, phasic transfer, chromatography or the like.

Method J:

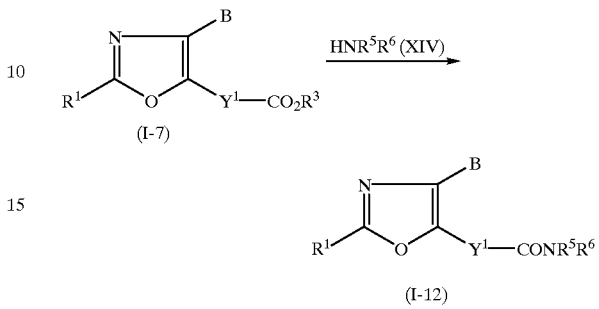

wherein all symbols are of the same meanings as those mentioned above.

Compounds (I-12) which correspond to the compounds (I) where A is an amidated carboxy group, can be produced, for example, by reacting a compound (I-7) with a compound (XIV).

Where $R^3$ is an alkyl group having 1 to 5 carbon atoms in the compound (I-7), the reaction may be conducted in the presence of a solvent that does not have any influence on the reaction or in the presence of no solvent.

The solvent that does not have any influence on the reaction includes, for example, alcohols such as methanol and ethanol; aromatic hydrocarbons such as toluene and xylene; pyridine, N,N-dimethylformamide, and dimethylsulfoxide.

The amount of the compound (XIV) to be used is preferably an excess one over the compound (I-7).

The reaction temperature ranges from 20 to 200° C., and the reaction time ranges from 0.1 to 20 hours.

Where $R^3$ is a hydrogen atom in the compound (I-7), the reaction may be conducted according to a method of directly condensing the compound (I-7) with the compound (XIV) in the presence of a dehydrating agent (e.g., dicyclohexylcarbodiimide), or a method of suitably reacting a reactive derivative of the compound (I-7) with the compound (XIV). In this reaction, the reactive derivative of the compound (I-7) includes, for example, acid anhydrides, acid halides (e.g., acid chlorides, acid bromides), imidazolides, and mixed acid anhydrides (e.g., anhydrides with methyl carbonate, ethyl carbonate or isobutyl carbonate).

Of these, the most simple method is to use such an acid halide or mixed acid anhydride.

For example, when an acid halide is used, the reaction may be conducted in the presence of a base in a solvent that does not have any influence on the reaction.

The base includes, for example, triethylamine, N-methylmorpholine, N,N-dimethylaniline, sodium hydrogencarbonate, potassium carbonate, and sodium carbonate.

The solvent that does not have any influence on the reaction includes, for example, halogenated hydrocarbons such as chloroform and dichloromethane; aromatic hydrocarbons such as benzene and toluene; ethyl acetate, tetrahydrofuran, water; and mixed solvents of these.

The amount of the compound (XIV) to be used may be from about 1 to about 1.5 molar equivalents relative to the compound (I-7).

The reaction temperature ranges from about −30° C. to about 100° C. The reaction time ranges from 0.5 to 20 hours.

On the other hand, where a mixed acid anhydride is used, the compound (I-7) is first reacted with a chlorocarbonate (e.g., methyl chlorocarbonate, ethyl chlorocarbonate, or isobutyl chlorocarbonate) in the presence of a base (e.g., triethylamine, N-methylmorpholine, N,N-dimethylaniline, sodium hydrogencarbonate, potassium carbonate, sodium carbonate), and then reacted with the compound (XIV). The amount of the compound (XIV) to be used may be from about 1 to about 1.5 molar equivalents relative to the compound (I-7).

This reaction may be conducted in a solvent that does not have any influence on the reaction. Such an inert solvent includes, for example, halogenated hydrocarbons such as chloroform and dichloromethane; aromatic hydrocarbons such as benzene and toluene; ethyl acetate, tetrahydrofuran, water; and mixed solvents of these.

The reaction temperature ranges from about −30° C. to about 50° C., and the reaction time ranges from 0.5 to 20 hours.

The compounds (I-12) thus produced may be isolated and purified through any ordinary separating and isolating means, for example, through concentration, concentration under reduced pressure, solvent extraction, precipitation, recrystallization, transsolvation, chromatography or the like.

Method K:

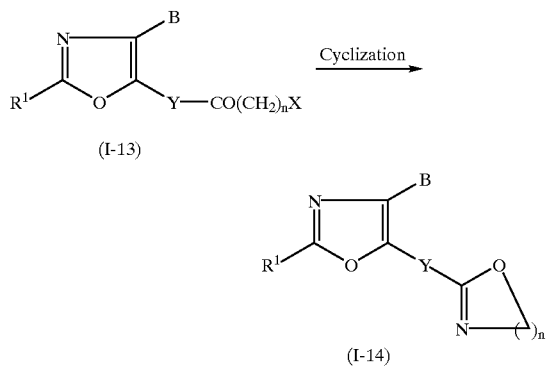

wherein n represents 2 or 3; and the other symbols are of the same meanings as those mentioned above.

Compounds (I-14) which correspond to the compounds (I) where A is a heterocyclic group, can be produced, for example, through cyclization of a compound (I-13).

This reaction may be conducted in the presence of a base in a solvent that does not have any influence on the reaction.

The base includes, for example, alkali metal salts such as potassium hydroxide, sodium hydroxide, sodium hydrogencarbonate and potassium carbonate; amines such as pyridine, triethylamine and N,N-dimethylaniline; metal hydrides such as potassium hydride and sodium hydride; sodium methoxide, sodium ethoxide, and potassium t-butoxide. The amount of the base to be used may be preferably from 1 to 5 molar equivalents relative to the compound (I-13).

The solvent that does not have any influence on the reaction includes, for examples aromatic hydrocarbons such as benzene, toluene and xylene; ethers such as tetrahydrofuran and dioxane; ketones such as acetone and 2-butanone; halogenated hydrocarbons such as chloroform and dichloromethane; N,N-dimethylformamide, dimethylsulfoxide; and mixed solvents of these.

The reaction temperature ranges generally from −50° C. to 150° C., preferably from about −10° C. to about 100° C. The reaction time ranges from 0.5 to 20 hours.

The compounds (I-14) thus produced may be isolated and purified through any ordinary separating and isolating means, for example, through concentration, concentration under reduced pressure, solvent extraction, precipitation, recrystallization, transsolvation, chromatography or the like.

Method L:

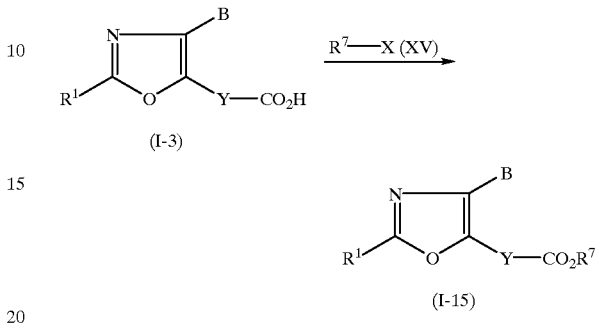

wherein $R^7$ represents an alkyl, aralkyl, aryl or heteroarylalkyl group; and the other symbols are of the same meanings as those mentioned above.

The alkyl, aralkyl, aryl or heteroarylalkyl group to represented by $R^7$, include the examples of the alkyl, aralkyl, aryl or heteroarylalkyl moiety of the esterified carboxy group, or that is, the alkoxycarbonyl, aralkyloxycarbonyl, aryloxycarbonyl or heteroarylalkyloxycarbonyl group, that have been mentioned hereinabove for the substituent for $R^1$ or A.

Compounds (I-15) which correspond to the compounds (I) where A is an esterified carboxy group, can be produced, for example, by reacting a compound (I-3) with a compound (XV). This reaction may be conducted in any ordinary manner, in the presence of a base in a solvent that does not have any influence on the reaction.

The base includes, for example, alkali metal salts such as potassium hydroxide, sodium hydroxide, lithium hydroxide, sodium hydrogencarbonate, potassium carbonate and sodium carbonate; metal hydrides such as sodium hydride; sodium methoxide, and sodium ethoxide.

The solvent that does not have any influence on the reaction includes, for example, ethers such as tetrahydrofuran and dioxane; ketones such as acetone and 2-butanone; N,N-dimethylformamide, dimethylsulfoxide; and mixed solvents of these.

The amount of the compound (XV) to be used may be preferably from about 1 to about 10 molar equivalents relative to the compound (I-3).

The reaction temperature ranges generally from −20° C. to 150° C., preferably from about 0° C. to about 100° C. The reaction time ranges from 0.5 to 20 hours.

The compounds (I-15) thus produced may be isolated and purified through any ordinary separating and isolating means such as concentration, concentration under reduced pressure, solvent extraction, precipitation, recrystallization, phasic transfer, chromatography or the like.

Method M:

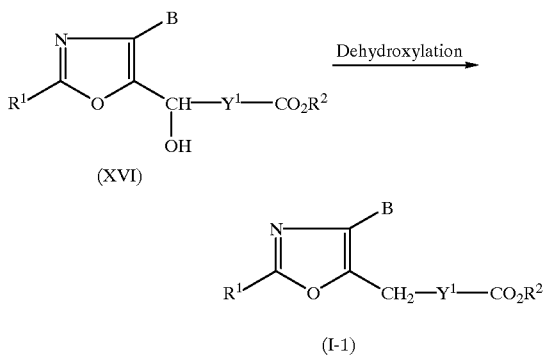

wherein all symbols are of the same meanings as those mentioned above.

The compound (I-16) can be produced by dehydroxylation of the compound (XVI). In this method, the compound (XVI) is directly reduced by silane, or the hydroxy group on the compound (XVI) is halogenated and further reduced. The reduction with silane is promoted by reaction with the compound (XVI) and triethylsilane or diethylsilane in trifluoro acetic acid. The halogenating agent includes, for example, thionyl chloride and phosphorus tribromide. For the reducing agent, metals such as iron, zinc are preferably used in hydrochloric acid or acetic acid.

The compounds (I-16) thus produced may be isolated and purified through any ordinary separating and isolating means such as concentration, concentration under reduced pressure, solvent extration, precipitation, recrystallization, phasic transfer, chromatography or the like.

The starting compounds(XVI) can be produced by the following Method N.

Method N:

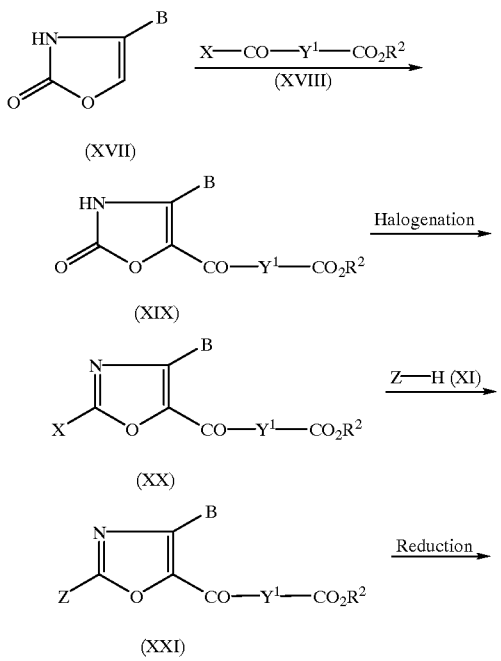

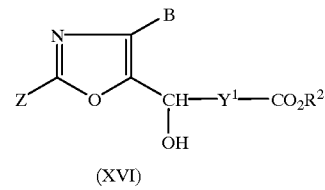

wherein all symbols are of the same meanings as those mentioned above.

In this method, the compound(XIX) can be produced by condensing the compound(XVII) and the compound (XVIII). This condensing reaction is the same manner as producing the compound(VII) by condensing the compound (V) and the compound(VI) as described in the Method R. Further, the compound(XX) can be produced by halogenating the compound(XIX). This halogenating reaction is the same manner as the halogenating reaction of the compound (II) as described in the Method A. The compound(XXI) can be produced by reacting with thus-obtained compound(XX) and the compound(XI). This reaction is conducted in the same manner as producing the compound(I-5) by reacting with the compound(I-4) and the compound(XI). Further, the compound(XVI) can be produced by reducing the compound(XXI). The reducting reaction is conducted in the same manner as the reacting reaction as described in the Method E.

Method O:

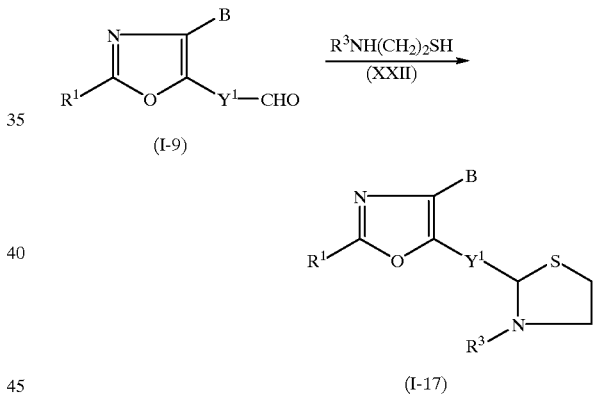

wherein all symbols are of the same meanings as those mentioned above.

The compound(I-17) wherein A is a heterocyclic group in the compound(I) can be produced by reacting with the compound(I-9).and the compound(XXII). This reaction may be effected in any ordinary manner, for example, in the presence of a base or an acid in a solvent that does not have any influence on the reaction. The acid used in this reaction includes, for example, hydrochloric acid, sulfuric acid, phosphoric acid, acetic acid and p-toluenesulfonic acid. The base used in this reaction includes, for example, sodium acetate and p-toluenesulfonyl pyridine.

The amount of the acid or the base to be used may be from about 0.1 to 2 molar equivalents relative to the compound (I-9).

The solvent that does not have any influence on the reaction includes, for example, aromatic hydrocarbons such as benzene, toluene; tetrahydrofuran; acetic acid.

The reaction temperature generally ranges from about −20 to 200° C., preferably from about 0 to 150° C. The reaction time ranges from about 0.5 to 20 hours.

The compounds (I-17) thus produced may be isolated and purified through any ordinary separating and isolating means such as concentration, concentration under reduced pressure, solvent extration, precipitation, recrystallization, phasic transfer, chromatography or the like.

Method P:

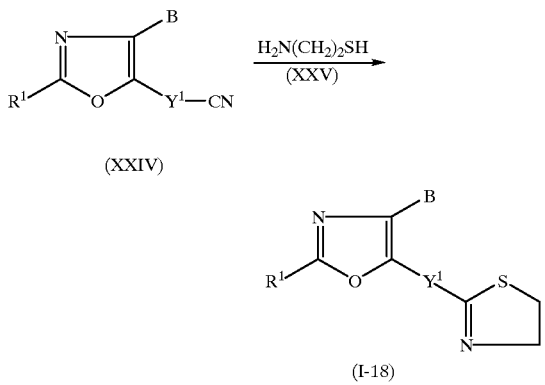

wherein all symbols are of the same meanings as those mentioned above.

The compound(I-18) wherein A is a heterocyclic group in the compound(I) can be produced by reacting with the compound(XXIV) and the compound(XXV). This reaction may be conducted in any ordinary manner in a solvent that does not have any influence on the reaction. The solvent that does not have any influence on the reaction includes, for example, alcohols such as methanol, ethanol, propanol, isopropanol; aromatic hydrocarbons such as benzene, toluene; tetrahydrofuran; N,N-dimethylformamide; pyridine; acetic acid.

The reaction temperature generally ranges from about –20 to 200° C., preferably about 0 to 150° C. The reaction time ranges from about 0.5 to 20 hours.

The compounds (I-18) thus produced may be isolated and purified through any ordinary separating and isolating means such as concentration, concentration under reduced pressure, solvent extration, precipitation, recrystallization, phasic transfer, chromatography or the like.

Method O:

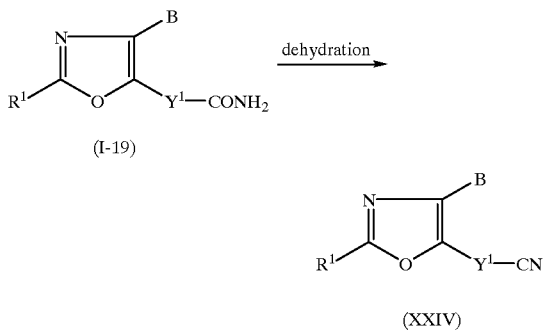

wherein all symbols are of the same meanings as those mentioned above.

The compound(XXIV) can be produced by dehydration of the compound(I-19). This reaction may be conducted in any ordinary manner in a solvent that does not have any influences on the reaction. The dehydrating agent includes, for example, sulfuric acid, acetic anhydride, phosphorus pentaoxide, phosphorus oxychloride. This solvent that does not have any influences on the reaction includes, for example, alcohols such as methanol, ethanol, propanol, isopropanol; aromatic hydrocarbons such as benzene, toluene; tetrahydrofuran; N,N-dimethylformamide.

The reaction temperature generally ranges from about –20 to 200° C., preferably 0 to 150° C. The reaction time ranges from about 0.5 to 20 hours.

The compounds (XXIV) thus produced may be isolated and purified through any ordinary separating and isolating means such as concentration, concentration under reduced pressure, solvent extration, precipitation, recrystallization, phasic transfer, chromatography or the like.

The starting compounds (II), (III) and (IV) to be used for the production of the compounds (I) of the invention can be produced by any per-se known methods. For example, these starting compounds can be produced by the methods mentioned hereinafter or according to these, or by the methods described in EP-92239 and JP59-190976 or according to those methods.

The starting compounds (II) for the Method A can be produced, for example, by the following method R.

Method R:

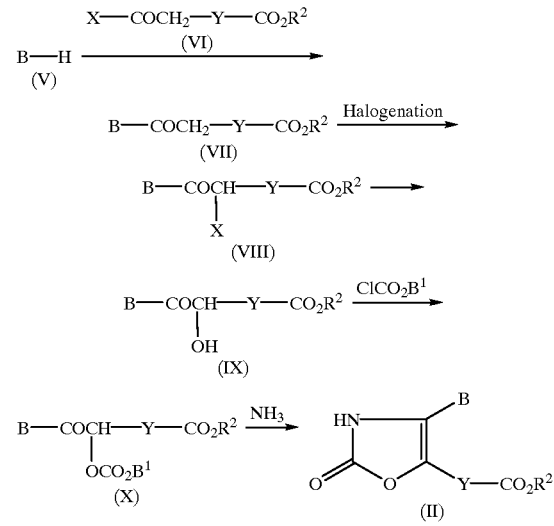

wherein $B^1$ represents an optionally substituted phenyl group; and the other symbols are of the same meanings as those mentioned above.

The substituent for the optionally substituted phenyl group represented by $B^1$ includes, for example, an alkyl group having 1 to 4 carbon atoms (e.g., methyl), a halogen atom (e.g., chlorine), and a nitro group.

In this process, a compound (V) is first condensed with a compound (VI) to obtain a compound (VII). This reaction may be conducted in any ordinary manner, in the presence of a Lewis acid and in the presence of a solvent that does not have any influence on the reaction or in the presence of no solvent.

The Lewis acid includes, for example, aluminium chloride, titanium tetrachloride, tin tetrachloride, and boron trifluoride. The amount of the Lewis acid to be used may be preferably from 1 to 5 molar equivalents relative to the compound (V).

The solvent that does not any influence on the reaction includes, for example, halogenated hydrocarbons such as chloroform, dichloromethane, 1,2-dichloroethane and carbon tetrachloride; carbon disulfide; and mixed solvents of these.

The amount of the compound (VI) to be used may be from 1 to 5 molar equivalents, preferably from 1 to 3 molar equivalents, relative to the compound (V).

The reaction temperature ranges generally from −20° C. to 150° C., preferably from about −10° C. to about 80° C. The reaction time ranges from 0.5 to 20 hours.

Next, the compound (VII) is halogenated to obtain a compound (VIII). This reaction may be conducted in any ordinary manner, generally in the presence of a halogenating agent in a solvent that does not have any influence on the reaction.

The halogenating agent includes, for example, chlorine and bromine. The amount of the halogenating agent to be used may be preferably from 1 to 1.5 molar equivalents relative to the compound (VII).

The solvent that does not have any influence on the reaction includes, for example, ethers such as diethyl ether, tetrahydrofuran and dioxane; halogenated hydrocarbons such as dichloromethane and chloroform; acetic acid; and mixed solvents of these.

The reaction temperature ranges generally from −20° C. to 150° C., preferably from about −10° C. to about 80° C. The reaction time ranges from 0.5 to 20 hours.

Next, the thus-obtained compound (VIII) is suitably reacted with a salt of an organic acid in the presence of a solvent that does not have any influence on the reaction, to obtain a compound (IX).

The salt of an organic acid includes, for example, sodium formate, potassium formate, and sodium acetate. The amount of the salt may be from 1 to 20 molar equivalents, preferably from about 2 to about 10 molar equivalents, relative to the compound (VIII).

The solvent that does not have any influence on the reaction includes, for example, alcohols such as methanol and ethanol.

The reaction temperature ranges generally from 0 to 150° C., preferably from about 30 to about 100° C. The reaction time ranges from 1 to 50 hours.

Next, the resulting compound (IX) is reacted with a chlorocarbonate to obtain a compound (X). This reaction may be conducted in any ordinary manner, in the presence of a base in a solvent that does not have any influence on the reaction.

The base includes, for example, alkali metal salts such as potassium hydroxide, sodium hydroxide, sodium hydrogencarbonate and potassium carbonate; and amines such as pyridine, triethylamine and N,N-dimethylaniline. The amount of the base to be used may be preferably from 2 to 5 molar equivalents relative to the compound (IX).

The solvent that does not have any influence on the reaction includes, for example, aromatic hydrocarbons such as benzene, toluene and xylene; ethers such as tetrahydrofuran and dioxane; halogenated hydrocarbons such as chloroform and dichloromethane; N,N-dimethylformamide, dimethylsulfoxide; and mixed solvents of these.

The reaction temperature ranges generally from −50° C. to 150° C., preferably from about −30° C. to about 50° C. The reaction time ranges from 0.5 to 20 hours.

Next, the compound (X) is reacted with ammonia or its salt to obtain the intended compound (II). This reaction may be conducted generally in the presence of a solvent that does not have any influence on the reaction.

The ammonia or its salt includes, for example, ammonia gas, and ammonium acetate. For example, when such an ammonium salt is used, its amount may be from 1 to 20 molar equivalents relative to the compound (X).

The solvent that does not have any influence on the reaction includes, for example, ethers such as tetrahydrofuran and dioxane; acetic acid; and mixed solvents of these.

The reaction temperature ranges generally from 0 to 150° C., preferably from about 50 to about 120° C. The reaction temperature ranges from 0.5 to 20 hours.

The compounds (II) thus produced may be isolated and purified through any ordinary separating and isolating means such as concentration, concentration under reduced pressure, solvent extraction, precipitation, recrystallization, phasic transfer, chromatography or the like.

The starting compounds (III) for the Method D can be produced, for example, by the following method S.

Method S:

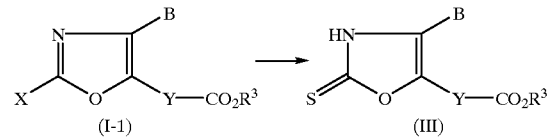

wherein all symbols are of the same meanings as those mentioned above.

The compounds (III) can be produced by reacting a compound (I-1) with thiourea, thioacetic acid or its salt, in the presence of a base in a suitable solvent that does not have any influence on the reaction.

The base includes, for example, alkali metal salts such as potassium hydroxide, sodium hydroxide, lithium hydroxide, sodium hydrogencarbonate, and potassium carbonate.

The solvent that does not have any influence on the reaction includes, for example, ethers such as tetrahydrofuran and dioxane; N,N-dimethylformamide, dimethylsulfoxide; and mixed solvents of these.

The amount of thiourea, thioacetic acid or its salt to be used may be from 1 to 20 molar equivalents, preferably from about 2 to about 10 molar equivalents, relative to the compound (I-1).

The reaction temperature ranges generally from 0 to 150° C., preferably from about 50 to about 120° C. The reaction time ranges from 0.1 to 20 hours.

The compounds (III) thus produced may be isolated and purified through any ordinary separating and isolating means such as concentration, concentration under reduced pressure, solvent extraction, precipitation, recrystallization, phasic transfer, chromatography or the like.

The starting compounds (IV) for the Method H can be produced, for example, by the following method T.

Method T:

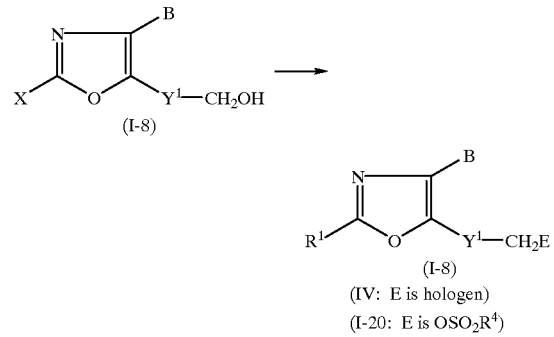

wherein all symbols are of the same meanings as those mentioned above.

The compound (IV), wherein E is halogen, can be produced by reacting a compound (I-8) with a halogenating agent, and the compound (IV), wherein E is $OSO_2R^4$, can be produced by reacting a compound (I-8) with a sulfonylating agent.

Where a halogenating agent is used, it is preferably thionyl chloride, phosphorus tribromide or the like. In this case, produced are the compounds (IV) where E is chlorine or bromine. The amount of the halogenating agent to be used may be from about 1 to about 20 molar equivalents relative to the compound (I-8).

The reaction may be effected generally in a solvent that does not have any influence on the reaction (e.g., benzene, toluene, chloroform, dichloromethane). If desired, an excess amount of the halogenating agent may be used for the solvent.

The reaction temperature ranges generally from −20° C. to 150° C., preferably from about 10 to about 100° C. The reaction time ranges 0.1 to 20 hours.

Where a sulfonylating agent is used, it is preferably mesyl chloride, tosyl chloride, benzenesulfonyl chloride or the like. In this case, produced are the compounds (I-20) where E is a mesyloxy, tosyloxy or benzenesulfonyloxy group, respectively.

The reaction may be conducted generally in the presence of a solvent that does not have any influence on the reaction, preferably in the presence of a suitable base.

The solvent that does not have any influence on the reaction includes, for example, aromatic hydrocarbons such as benzene and toluene; halogenated hydrocarbons such as chloroform and dichloromethane; ethyl acetate, and tetrahydrofuran.

The base includes, for example, triethylamine, N-methylmorpholine, N,N-dimethylaniline, sodium hydrogencarbonate, potassium carbonate, and sodium carbonate.

The amount of the sulfonylating agent and that of the base to be used may be from about 1 to about 1.5 molar equivalents each, relative to the compound (I-8).

The reaction temperature ranges generally from −20° C. to 150° C., preferably from about 10 to about 100° C. The reaction time ranges from 0.1 to 20 hours.

The compounds (IV) thus produced may be isolated and purified through any ordinary separating and isolating means such as concentration, concentration under reduced pressure, solvent extraction, precipitation, recrystallization, phasic transfer, chromatography or the like.

BEST MODE FOR CARRYING OUT THE INVENTION

Now, the present invention is described in more detail hereinunder, with reference to the following test example, reference examples, examples and formulation examples, which, however, are not intended to restrict the scope of the invention. In the following reference examples and examples, % is by weight unless otherwise specifically indicated.

Experimental Example 1

Test for Blood Sugar Depression in Mice

After being fasted for 20 hours, 9- to 12-week-old, male KKA$^y$ mice (five mice in each group) were orally given the test compound at a dose of 30 mg/kg/10 ml through a stomach tube. Control mice were orally given 5% gum arabic solution. Blood samples (70 μl) were obtained from orbital venous plexus through capillary tube before and 60 and 120 minutes after the administration of the test compound. Blood glucose was determined according to a glucose oxidase method using a commercial kit (Iatrochem, GIU(A), Iatron Labs. Inc.). Blood glucose level at 60 or 120 minutes of the test groups was compared with that of control group, and was shown as blood glucose depression (%) (Table 1).

TABLE 1

| Test Compound | Degree of Blood Glucose Depression (%) | |
|---|---|---|
| (Example Number) | After 60 minutes | After 120 minutes |
| 15 | 22 | 26 |
| 25 | 38 | 27 |
| 26 | 32 | 27 |
| 28 | 24 | 33 |
| 31 | 27 | 28 |
| 32 | 25 | 28 |
| 34 | 27 | 25 |
| 36 | 23 | 18 |

As demonstrated in the above table 1, the compounds (I) of the present invention have a blood sugar (blood glucose) depressing effect and are useful in agents or diabetes.

Experimental Example 2

Insulinotropic effect on MIN6 cells

MIN6 cells established from mouse beta cell tumor were cultured in DMEM supplemented with 15% fetal bovine serum on 12-well plate at 37° C. in 5% $CO_2$, and were used at the stage of subconfluency. Cells were washed twice with PBS and incubated in Krebs-Ringer HEPES(KRH) containing with 0.1 mM glucose for 30 minutes. Then they were incubated in KRH containing with 12.5 mM glucose and 0.1% DMSO (control) or compound (10 μM) for 2 hours. Medium was collected and insulin concentration was measured using a commercial radioimmunoassay kit (Amarsham Inc.). The plate was washed once with PBS and cellular protein content was determined by the method of Lowrey et al.(J. Biol. Chem. 193, 265–275, 1951). Insulinotropic activity of the compound was indicated as percentage of control (Table 2).

TABLE 2

| Test Compound (Example Number) | Insulin secretion-promoting effect (%) |
|---|---|
| 36 | 272 |
| 65 | 397 |
| 72 | 303 |
| 83 | 359 |
| 89 | 385 |

As demonstrated in the above Table 2, the compounds (I) of the present invention have insulin secretion-promoting effect and are useful in agents for diabetes.

Reference Example 1

Bromine (46.5 g) was added dropwise to a dichloromethane (400 ml) solution of methyl 4-(4-chlorobenzoyl)butyrate (70.0 g). After stirring for 15 minutes, the reaction mixture was washed with water, dried ($MgSO_4$), and concentrated to obtain methyl 4-bromo-4-(chlorobenzoyl)butyrate (89.5 g, 96%) as an oily substance. NMR (δ ppm in $CDCl_3$): 2.3–2.7(4 H,m), 3.71(3H,s), 5.33(1H,dd,J=8&5.5 Hz), 7.48(2H,d,J=8.5 Hz), 7.98(2H,d,J=8.5 Hz).

Reference Example 2

A mixture of methyl 4-bromo-4-(chlorobenzoyl)butyrate (89.5 g), sodium formate (76.2 g) and methanol (400 ml)

was stirred under reflux for 12 hours. The reaction mixture was concentrated, and water was added to the resulting residue and then extracted with ethyl acetate. The ethyl acetate layer was washed with water, and dried (MgSO$_4$). The solvent was evaporated to give methyl 4-(chlorobenzoyl)-4-hydroxybutyrate (72.0 g, 100%) as an oily substance. This oily substance (72.0 g) was dissolved in tetrahydrofuran (400 ml), pyridine (22.2 g) was added thereto, and thereafter phenyl chlorocarbonate (43.8 g) was dropwise added thereto with cooling with ice. After the reaction mixture was stirred at room temperature for 1 hour, water was added to the reaction mixture and then extracted with ethyl acetate. The ethyl acetate layer was washed with 2N hydrochloric acid and then with water, and dried (MgSO$_4$). The solvent was evaporated, and the crystals thus precipitated were collected by filtration to obtain methyl 4-(4-chlorobenzoyl)-4-phenoxycarbonyloxybutyrate (61.2 g, 58%). This was recrystallized from methanol to give colorless prisms. mp 97–98° C.

Reference Example 3

A mixture of methyl 4-(4-chlorobenzoyl)-4-phenoxycarbonyloxybutyrate (61.2 g), ammonium acetate (62.2 g) and acetic acid (300 ml) was stirred under reflux for 1.5 hours. The reaction mixture was concentrated, water was added to the resulting residue, and the crystals thus precipitated were collected by filtration. These were recrystallized from methanol to give colorless needles of methyl 3-[4-(4-chlorophenyl)-2-oxo-4-oxazolin-5-yl]propionate (36.6 g, 79%). m.p. 147–148° C.

Reference Example 4

A mixture of methyl 2-chloro-4-(4-chlorophenyl)-5-oxazolepropionate (5.72 g), thiourea (4.57 g) and ethanol (70 ml) was stirred under reflux for 30 minutes. An aqueous solution of 2N sodium hydroxide (40 ml) was added to the reaction mixture, and stirred under reflux for an additional 30 minutes. Water was added to the reaction mixture, which was then neutralized with 6N hydrochloric acid. The crystals thus precipitated were collected by filtration to obtain 3-[4-(4-chlorophenyl)-2-thioxo-4-oxazolin-5-yl]propionic acid (5.41 g, yield: 96%). This was recrystallized from ethanol to give colorless needles. mp 196–197° C.

Reference Example 5

Phosphorus oxychloride(585 mg) was added dropwise into a N,N-dimethylformamide solution (20 ml) of 4-(4-chlorophenyl)-2-(2-methyl-1-imidazolyl)-5-oxazolepropionamide(840 mg) at room temperature. After stirring for 1 hour, the reaction mixture was poured into ice water, and neutralized with saturated sodium bicarbonate. The precipitating crystals are collected by filtration to give 4-(4-chlorophenyl)-5-(2-cyanoethyl)-2-(2-methyl-1-imidazolyl)oxazole(650 mg, 82%). This was recrystallized with acetone-isopropyl ether to give colorless prisms. mp 163–164° C.

Reference Example 6

Adipic acid monomethyl ester chloride (17.9 g) was added dropwise into a mixture of chlorobenzene(33.8 g) and aluminum chloride anhydrous(26.7 g) with cooling with ice. After stirring for 2 hours, the reaction mixture was poured into ice water, and extracted with ethyl acetate. The ethyl acetate layer was washed with water, and dried (MgSO$_4$). The solvent was evaporated to give methyl 5-(4-chlorobenzoyl)pentanoate. This was dissolved into dichloromethane(100 ml), thereto bromine(16.0 g) was added dropwise. The reaction mixture was washed with water and then with sodium hydrogensulfite. The dichloromethane layer was washed with water, and dried (MgSO$_4$). The solvent was evaporated to give methyl 5-bromo-5-(4-chlorobenzoyl)pentanoate(31.7 g, 95%) as an oily substance.

NMR(δ ppm in CDCl$_3$): 1.6–2.3(4H, m), 2.42(2H, t, J=7 Hz), 3.68(3H, s), 5.08(1H, dd, J=8&6.5 Hz), 7.47(2H, d, J=9 Hz), 7.96(2H, d, J=9 Hz).

Reference Example 7

In the same manner as Reference Example 2, methyl 5-(4-chlorobenzoyl)-5-phenoxycarbonyloxypentanoate as an oily substance (yield: 67%) was obtained by reacting a reactant which was obtained by reacting methyl 5-bromo-5-(4-chlorobenzoyl)pentanoate with sodium formate, with phenyl chlorocarbonate.

NMR(δ ppm in CDCl$_3$): 1.8–2.1(4H, m), 2.40(2H, t, J=7 Hz), 3.67(3H, s), 5.82(1H, dd, J=7.5&4.5 Hz), 7.15–7.45 (5H, m), 7.48(2H, d, J=9 Hz), 7.91(2H, d, J=9 Hz).

Reference Example 8

In the same manner as Reference Example 3, obtained was methyl 4-[4-(4-chlorophenyl)-2-oxo-4-oxazolin-5-yl] butanoate by reaction of methyl 5-(4-chlorobenzoyl)-5-phenoxycarbonyloxypentanoate with ammonium acetate. This was recrystallized with acetone-isopropyl ether to give colorless prisms. mp 121–122° C.

Reference Example 9

Titanium tetrachloride(15.5 g) was added dropwise into a mixture of 4-(4-chlorophenyl)-4-oxazolin-2-one(4.00 g), ethyl chloroglyoxylate(5.58 g) and dichloromethane(30 ml) at room temperature. After stirring for 2 hours, the reaction mixture was poured into ice water, and extracted with ethyl acetate. The ethyl acetate layer was washed with water, and dried(MgSO$_4$). The solvent was evaporated to give ethyl 2-[4-(4-chlorophenyl)-2-oxo-4-oxazolin-5-yl]-2-oxoacetate as crystals(5.38 g, 89%). This was recrystallized from ethyl acetate-hexane to give pale yellow prisms. mp 152–153° C.

Reference Example 10

A mixture of ethyl 2-(4-(4-chlorophenyl)-2-oxo-4-oxazolin-5-yl]-2-oxoacetate(2.50 g), phosphorus oxychloride(6.48 g) and pyridine(740 mg) was stirred for 1 hour at 120–125° C. The reaction mixture was poured into ice water, and extracted with ethyl acetate. The ethyl acetate layer was washed with water, and dried(MgSO$_4$). The residue obtained by evaporating the solvent was subjected to silica gel column chromatography. From the fraction eluted with ethyl acetate-hexane(1:9, v/v), obtained was ethyl 2-[2-chloro-4-(4-chlorophenyl)-5-oxazolyl)-2-oxoacetate (450 mg, 17%). This was recrystallized from ethyl acetate-hexane to give colorless prisms. mp 98–99° C.

Reference Example 11

Sodium hydride(oil, 60%, 710 mg) was gradually added to a mixture of ethyl 2-[2-chloro-4-(4-chlorophenyl)-5-oxazolyl]-2-oxoacetate(4.63 g), 2-methylimidazole(1.45 g) and N,N-dimethylformamide(50 ml) at 0° C. After stirring for 1 hour at room temperature, the reaction mixture was poured into ice water to give ethyl 2-[4-(4-chlorophenyl)-2-(2-methyl-1-imidazolyl)-5-oxazolyl]-2-oxoacetate(3.12 g, 59%). This was recrystallized from ethyl acetate-hexane to give colorless prisms. mp 126–127° C.

Reference Example 12

Sodium borohydride(95 mg) was added to a tetrahydrofuran(60 ml)-2-propanol(30 ml) solution of ethyl 2-(4-(4-chlorophenyl)-2-(2-methyl-1-imidazolyl)-5-oxazolyl]-2-oxoacetate(2.93 g) at 0° C. After stirring for 30 minutes, the reaction mixture was poured into ice water, and extracted with ethyl acetate. The ethyl acetate layer was washed with water, and dried($MgSO_4$). The solvent was evaporated to give ethyl 2-[4-(4-chlorophenyl)-2-(2-methyl-1-imidazolyl)-5-oxazolyl]-2-hydroxyacetate(2.20 g, 75%). This was recrystallized from acetone-ethyl acetate to give colorless prisms. mp 197–198° C. (degradation)

Reference Example 13

N,N-dimethylformamide(1 drop) was added to a tetrahydrofuran solution(40 ml) of pimelic acid monoethyl ester (25.5 g), and thereto oxalyl chloride(18.8 g) was added dropwise. After stirring for 2 hours at room temperature, the reaction mixture was concentrated. The residue was added dropwise to a mixture of chlorobenzene(61.0 g) and aluminum chloride anhydrous (36.1 g) under ice water. After stirring for 3 hours, the reaction mixture was poured into 1N-hydrochloric acid, and extracted with ethyl acetate. The ethyl acetate layer was washed with water, and dried ($MgSO_4$). The solvent was evaporated to give ethyl 6-(4-chlorobenzoyl)hexanate (37.7 g, 97%) as an oily substance.

NMR($\delta$ ppm in $CDCl_3$): 1.25(3H, t, J=7 Hz), 1.3–1.9(6H, m), 2.32(2H, t, J=7.5 Hz), 2.95(2H, t, J=7.5 Hz), 4.13(2H, q, J=7 Hz), 7.44(2H, d, J=8.5 Hz), 7.90(2H, d, J=8.5 Hz).

Reference Example 14

In the same manner as Reference Example 13, obtained was ethyl 7-(4-chlorobenzoyl)heptanoate as an oily substance(yield: 90%) by reaction of a reactant of suberic acid monoethyl ester and oxalyl chloride, with chlorobenzene.

NMR($\delta$ ppm in $CDCl_3$): 1.25(3H, t, J=7 Hz), 1.2–1.9(8H, m), 2.2–2.4(2H, m), 2.93(2H, t, J=7.5 Hz), 4.13(2H, q, J=7 Hz), 7.43(2H, d, J=8.5 Hz), 7.90(2H, d, J=8.5 Hz).

Reference Example 15

Bromine(21.1 g) was added dropwise to a dichloromethane solution (200 ml) of ethyl 6-(4-chlorobenzoyl)hexanoate (37.3 g) at room temperature. After stirring for 30 minutes, the reaction mixture was washed with sodium hydrogensulfite, saturated sodium bicarbonate and water in turn. The dichloromethane layer was dried($MgSO_4$). The solvent was evaporated to give ethyl 6-bromo-6-(4-chlorobenzoyl)hexanoate(47.6 g, quant.) as an oily substance.

NMR($\delta$ ppm in $CDCl_3$): 1.25(3H, t, J=7 Hz), 1.3–2.3(6H, m), 2.34(2H, t, J=7 Hz), 4.13(2H, q, J=7 Hz), 5.06(1H, t, J=7 Hz), 7.47(2H, d, J=8.5 Hz), 7.96(2H, d, J=8.5 Hz).

Reference Example 16

In the same manner as Reference Example 15, obtained was ethyl 7-bromo-7-(4-chlorobenzoyl)heptanoate(yield: 79%) as an oily substance through reaction of ethyl 7-(4-chlorobenzoyl)heptanoate with bromine.

NMR($\delta$ ppm in $CDCl_3$): 1.25(3H, t, J=7 Hz), 1.2–1.9(8H, m), 2.2–2.4(2H, m), 4.12(2H, q, J=7 Hz), 5.06(1H, t, J=7 Hz), 7.47(2H, d, J=8.5 Hz), 7.96(2H, d, J=8.5 Hz).

Reference Example 17

A mixture of ethyl 6-bromo-6-(4-chlorobenzoyl) hexanoate (47.6 g), sodium formate(44.8 g) and methanol (250 ml) was stirred for 24 hours under reflux. The reaction mixture was concentrated. Water was added to the reaction mixture. This was extracted with ethyl acetate. The ethyl acetate layer was washed with water, and dried($MgSO_4$). The residue obtained by evaporating the solvent was subjected to silica gel column chromatography. From the fraction eluted with ethyl acetate-hexane(1:4, v/v), obtained was ethyl 6-(4-chlorobenzoyl)-6-hydroxyhexanoate(24.5 g, 62%) as an oily substance.

NMR($\delta$ ppm in $CDCl_3$): 1.23(3H, t, J=7 Hz), 1.3–2.0(6H, m), 2.28(2H, t, J=7 Hz), 3.63(1H, d, J=6.5 Hz), 4.10(2H, q, J=7 Hz), 4.95–5.1(1H, m), 7.49(2H, d, J=8.5 Hz), 7.86(2H, d, J=8.5 Hz).

Reference Example 18

In the same manner as Reference Example 17, obtained was ethyl 7-(4-chlorobenzoyl)-7-hydroxyheptanoate (yield: 31%) as an oily substance by reaction of ethyl 7-bromo-7-(4-chlorobenzoyl)heptanoate with sodium formate in methanol.

NMR($\delta$ ppm in $CDCl_3$): 1.24(3H, t, J=7 Hz), 1.3–2.0(8H, m), 2.27(2H, t, J=7.5 Hz), 3.63(1H, d, J=6.5 Hz), 4.11(2H, q, J=7 Hz), 4.95–5.1(1H, m), 7.49(2H, d, J=8.5 Hz), 7.87 (2H, d, J=8.5 Hz).

Reference Example 19

Phenyl chloroformate (14.1 g) was added dropwise to a mixture of ethyl 6-(4-chlorobenzoyl)-6-hydroxyhexanoate (24.5 g), pyridine(7.14 g) and tetrahydrofuran(200 ml) with cooling with ice. After stirring for 3 hours at room temperature, the reaction mixture was poured into ice water, and neutrized by 2N-hydrochloric acid. This was extracted with ethyl acetate. The ethyl acetate layer was washed with water, and dried($MgSO_4$). The solvent was evaporated to give ethyl 6-(4-chlorobenzoyl)-6-phenoxycarbonyloxyhexanate(32.3 g, 94%) as an oily substance.

NMR($\delta$ ppm in $CDCl_3$): 1.25(3H, t, J=7 Hz), 1.45–2.05 (6H, m), 2.32(2H, t, J=7 Hz), 4.12(2H, q, J=7 Hz), 5.79(1H, t, J=6 Hz), 7.1–7.5(7H, m), 7.89(2H, d, J=8.5 Hz).

Reference Example 20

In the same manner as Reference Example 19, obtained was ethyl 7-(4-chlorobenzoyl)-7-phenoxycarbonyloxyheptanoate (quant.) as an oily substance by reaction of ethyl 7-(4-chlorobenzoyl)-7-hydroxyheptanoate with phenyl chloroformate.

NMR($\delta$ ppm in $CDCl_3$): 1.25(3H, t, J=7 Hz), 1.25–2.0 (8H, m), 2.29(2H, t, J=7.5 Hz), 4.12(2H, q, J=7 Hz), 5.79(1H, t, J=7 Hz), 7.15–7.45(5H, m), 7.48(2H, d, J=8.5 Hz), 7.90(2H, d, J=8.5 Hz).

Reference Example 21

Ethyl 6-(4-chlorobenzoyl)-6-phenoxycarbonyloxyhexanoate (32.3 g), ammonium acetate (29.7 g) and acetic acid(150 ml) was stirred for 1 hour under reflux. Water was added to the reaction mixture to give ethyl 5-[4-(4-chlorophenyl)-2-oxo-4-oxazolin-5-yl]pentanoate (17.7 g, 71%). This was recrystallized from acetone-isopropyl ether to give colorless needls. mp 143–144° C.

Reference Example 22

In the same manner as Reference Example 21, obtained was ethyl 6-[4-(4-chlorophenyl)-2-oxo-4-oxazolin-5-yl]

hexanoate (yield: 87%) by reaction of ethyl 7-(4-chlorobenzoyl)-7-phenoxycarbonyloxyheptanoate with ammonium acetate.

This was recrystallized with acetone-isopropyl ether to give colorless prisms mp 113–114° C.

Example 1

A mixture of methyl 3-[4-(4-chlorophenyl)-2-oxo-4-oxazoline-5-yl]propionate (11.3 g), phosphorus oxychloride (18.6 g) and pyridine (3.2 ml) was stirred at 120 to 180° C. for 80 minutes. The reaction mixture was concentrated, and ice water was added thereto and then stirred at room temperature for 30 minutes. Then, this was extracted with ethyl acetate. The ethyl acetate layer was washed with water, and dried (MgSO$_4$). The solvent was evaporated, and the crystals thus precipitated were collected by filtration. These were recrystallized from isopropyl ether to give colorless needles of methyl 2-chloro-4-(4-chlorophenyl)-5-oxazolepropionate (8.56 g, 71%). m.p. 71–72° C.

Example 2

An aqueous solution of 1N sodium hydroxide (34 ml) was dropwise added to an ethanol (50 ml) solution of methyl 2-chloro-4-(4-chlorophenyl)-5-oxazolepropionate (8.50 g), with cooling with ice. After stirring for 20 minutes with cooling and then for 30 minutes at room temperature, 2N hydrochloric acid was added thereto, and the crystals thus precipitated were collected by filtration to obtain 2-chloro-4-(4-chlorophenyl)-5-oxazolepropionic acid (8.00 g, 99%). This was recrystallized from ethyl acetate to give colorless prisms. mp 169–170° C.

Example 3

2-Chloro-4-(4-chlorophenyl)-5-oxazolepropionic acid (1.43 g) was added to an ethanol solution of sodium ethoxide prepared from sodium (0.35 g) and ethanol (15 ml), and stirred under reflux for 30 minutes. The solvent was evaporated, and water was added to the residue, which was then acidified with 2N hydrochloric acid. The crystals thus precipitated were collected by filtration to obtain 4-(4-chlorophenyl)-2-ethoxy-5-oxazolepropionic acid (1.40 g, 95%). This was recrystallized from ethanol to give colorless prisms. mp 148–149° C.

Example 4

Sodium hydride (60% dispersion in oil, 0.60 g) was added to 2-propanol (20 ml), and stirred at room temperature for 10 minutes. To the reaction mixture was added 2-chloro-4-(4-chlorophenyl)-5-oxazolepropionic acid (1.43 g), and stirred under reflux for 30 minutes. Next, water was added to the resulting reaction mixture, which was then acidified with 2N hydrochloric acid, and the crystals thus precipitated were collected by filtration to obtain 4-(4-chlorophenyl)-2-isopropoxy-5-oxazolepropionic acid (1.35 g, 87%). This was recrystallized from isopropyl ether to give colorless prisms. mp 116–117° C.

Example 5

A mixture of 2-chloro-4-(4-chlorophenyl)-5-oxazolepropionic acid (1.43 g), phenol (0.94 g), potassium carbonate (2.10 g) and N,N-dimethylformamide (10 ml) was stirred at 140° C. for 3 hours. Water was added to the reaction mixture, which was then acidified with 6N hydrochloric acid. The crystals thus precipitated were collected by filtration to obtain 4-(4-chlorophenyl)-2-phenoxy-5-oxazolepropionic acid (1.60 g, 93%). This was recrystallized from ethyl acetate to give colorless needles. mp 136–137° C.

Example 6

Methyl iodide (0.34 ml) was dropwise added to a mixture of 3-[4-(4-chlorophenyl)-2-thioxo-4-oxazolin-5-yl] propionic acid (1.42 g), an aqueous solution of 2N sodium hydroxide (5.5 ml) and N,N-dimethylformamide (15 ml), with cooling with ice. After the reaction mixture was stirred for 30 minutes, water was added to the resulting reaction mixture, which was then acidified with 2 N hydrochloric acid. The crystals thus precipitated were collected by filtration to obtain 4-(4-chlorophenyl)-2-methylthio-5-oxazolepropionic acid (1.45 g, 97%). This was recrystallized from ethanol to give colorless needles. mp 183–184° C.

Example 7

In the same manner as in Example 6, obtained was 4-(4-chlorophenyl)-2-isopropylthio-5-oxazolepropionic acid (yield: 80%) by reaction of 3-[4-(4-chlorophenyl)-2-thioxo-4-oxazolin-5-yl]propionic acid with isopropyl iodide. This was recrystallized from ethanol to give colorless prisms. mp 132–133° C.

Example 8

In the same manner as in Example 6, obtained was 4-(4-chlorophenyl)-2-(2-pyridylmethylthio)-5-oxazolepropionic acid (yield: 98%) by reaction of 3-[4-(4-chlorophenyl)-2-thioxo-4-oxazolin-5-yl]propionic acid with 2-(chloromethyl)pyridine. This was recrystallized from ethanol to give colorless prisms. mp 125–126° C.

Example 9

In the same manner as in Example 6, obtained was 4-(4-chlorophenyl)-2-(3-pyridylmethylthio)-5-oxazolepropionic acid (yield: 96%) by reaction of 3-[4-(4-chlorophenyl)-2-thioxo-4-oxazolin-5-yl]propionic acid with 3-(chloromethyl)pyridine. This was recrystallized from ethanol to give colorless needles. mp 129–130° C.

Example 10

A mixture of 2-chloro-4-(4-chlorophenyl)-5-oxazolepropionic acid (1.43 g), thiophenol (0.54 ml), sodium methoxide-methanol solution (28%, 2.00 g) and methanol (15 ml) was stirred under reflux for 16 hours. Water was added to the reaction mixture, which was then acidified with 2 N hydrochloric acid. The crystals thus precipitated were collected by filtration to obtain 4-(4-chlorophenyl)-2-phenylthio-5-oxazolepropionic acid (1.60 g, 89%). This was recrystallized from methanol to give colorless needles. mp 156–157° C.

Example 11

A mixture of 2-chloro-4-(4-chlorophenyl)-5-oxazolepropionic acid (1.43 g), 4-methylthiophenol (0.68 g), potassium carbonate (2.07 g) and N,N-dimethylformamide (20 ml) was stirred under a nitrogen atmosphere at 100° C. for 40 minutes. Water was added to the reaction mixture, which was then acidified with 2 N hydrochloric acid. The crystals thus precipitated were collected by filtration to obtain 4-(4-chlorophenyl)-2-(4-methylphenylthio)-5-oxazolepropionic acid (1.73 g, 93%). This was recrystallized from ethanol to give colorless needles. mp 160–161° C.

Example 12

In the same manner as in Example 11, obtained was 4-(4-chlorophenyl)-2-(4-methyl-4H-1,2,4-triazol-3-ylthio)-5-oxazolepropionic acid (yield: 77%) by reaction of 2-chloro-4-(4-chlorophenyl)-5-oxazolepropionic acid with 4-methyl-4H-1,2,4-triazole-3-thiol. This was recrystallized from ethanol to give pale brown needles. mp 186–188° C.

Example 13

In the same manner as in Example 11, obtained was 4-(4-chlorophenyl)-2-(4-phenyl-4H-1,2,4-triazol-3-ylthio)-5-oxazolepropionic acid (yield: 61%) by reaction of 2-chloro-4-(4-chlorophenyl)-5-oxazolepropionic acid with 4-phenyl-4H-1,2,4-triazole-3-thiol. This was recrystallized from ethanol to give colorless needles. mp 122–123° C.

Example 14

In the same manner as in Example 11, obtained was 4-(4-chlorophenyl)-2-(1-phenyl-2-imidazolylthio)-5-oxazolepropionic acid (yield: 39%) by reaction of 2-chloro-4-(4-chlorophenyl)-5-oxazolepropionic acid with 1-phenylimidazole-2-thiol. This was recrystallized from ethanol to give pale brown needles. mp 185–187° C.

Example 15

In the same manner as in Example 11, obtained was 4-(4-chlorophenyl)-2-(2-pyridylthio)-5-oxazolepropionic acid (yield: 95%) by reaction of 2-chloro-4-(4-chlorophenyl)-5-oxazolepropionic acid with 2-mercaptopyridine. This was recrystallized from ethanol an to give pale yellow needles. mp 172–173° C.

Example 16

A mixture of 2-chloro-4-(4-chlorophenyl)-5-oxazolepropionic acid (1.43 g), an aqueous solution of 30% methylamine (4.0 ml) and 2-propanol (20 ml) was stirred in a sealed tube at 100° C. for 4 hours. The reaction mixture was concentrated, and water was added to the resulting residue. The pH was then adjusted 3 with 2 N hydrochloric acid. The crystals thus precipitated were collected by filtration to obtain 4-(4-chlorophenyl)-2-methylamino-5-oxazolepropionic acid (1.21 g, 86%). This was recrystallized from ethanol to give colorless prisms. mp 217–218° C.

Example 17

In the same manner as in Example 16, obtained was 4-(4-chlorophenyl)-2-dimethylamino-5-oxazolepropionic acid (yield: 92%) by reaction of 2-chloro-4-(4-chlorophenyl)-5-oxazolepropionic acid with dimethylamine. This was recrystallized from ethanol to give colorless needles. mp 189–190° C.

Example 18

A mixture of 2-chloro-4-(4-chlorophenyl)-5-oxazolepropionic acid (1.43 g), morpholine (2.2 ml) and 2-propanol (20 ml) was stirred under reflux for 4 hours. The reaction mixture was concentrated, and water was added to the residue. The pH was then adjusted 3 with 2 N hydrochloric acid. The crystals thus precipitated were collected by filtration to obtain 4-(4-chlorophenyl)-2-morpholino-5-oxazolepropionic acid (1.64 g, 98%). This was recrystallized from ethanol to give colorless needles. mp 180–181° C.

Example 19

In the same manner as in Example 18, obtained was 4-(4-chlorophenyl)-2-cyclohexylamino-5-oxazolepropionic acid (yield: 53%) by reaction of 2-chloro-4-(4-chlorophenyl)-5-oxazolepropionic acid with cyclohexylamine. This was recrystallized from ethanol to give colorless needles. mp 237–238° C.

Example 20

In the same manner as in Example 18, obtained was 4-(4-chlorophenyl)-2-(1-pyrrolidinyl)-5-oxazolepropionic acid (yield: 99%) by reaction of 2-chloro-4-(4-chlorophenyl)-5-oxazolepropionic acid with pyrrolidine. This was recrystallized from ethanol to give colorless needles. mp 199–200° C.

Example 21

In the same manner as in Example 18, obtained was 4-(4-chlorophenyl)-2-piperidino-5-oxazolepropionic acid (yield: 97%) by reaction of 2-chloro-4-(4-chlorophenyl)-5-oxazolepropionic acid with piperidine. This was recrystallized from ethanol to give colorless prisms. mp 185–186° C.

Example 22

In the same manner as in Example 18, obtained was 4-(4-chlorophenyl)-2-(2-methylpiperidino)-5-oxazolepropionic acid (yield: 44%) by reaction of 2-chloro-4-(4-chlorophenyl)-5-oxazolepropionic acid with 2-methylpiperidine. This was recrystallized from isopropyl ether to give colorless prisms. mp 126–128° C.

Example 23

In the same manner as in Example 18, obtained was 4-(4-chlorophenyl)-2-hexamethyleneimino-5-oxazolepropionic acid (yield: 90%) by reaction of 2-chloro-4-(4-chlorophenyl)-5-oxazolepropionic acid with hexamethyleneimine. This was recrystallized from ethanol to give colorless prisms. mp 137–138° C.

Example 24

A mixture of 2-chloro-4-(4-chlorophenyl)-5-oxazolepropionic acid (1.43 g), imidazole (1.70 g), potassium carbonate (2.80 g) and N,N-dimethylformamide (15 ml) was stirred at 130° C. for 2.5 hours. Water was added to the reaction mixture. The pH was then adjusted 6 with 2 N hydrochloric acid. The crystals thus precipitated were collected by filtration to obtain 4-(4-chlorophenyl)-2-(1-imidazolyl)-5-oxazolepropionic acid (1.35 g, 85%). This was recrystallized from methanol to give colorless needles. mp 194–195° C.

Example 25

In the same manner as in Example 24, obtained was 4-(4-chlorophenyl)-2-(2-methyl-1-imidazolyl)-5-oxazolepropionic acid (yield: 54%) by reaction of 2-chloro-4-(4-chlorophenyl)-5-oxazolepropionic acid with 2-methylimidazole. This was recrystallized from methanol to give colorless needles. mp 195–197° C.

Example 26

In the same manner as in Example 24, obtained was 4-(4-chlorophenyl)-2-(2-ethyl-1-imidazolyl)-5-oxazolepropionic acid (yield: 88%) by reaction of 2-chloro-4-(4-chlorophenyl)-5-oxazolepropionic acid with 2-ethylimidazole. This was recrystallized from methanol to give colorless needles. mp 197–199° C.

Example 27

In the same manner as in Example 24, obtained was 4-(4-chlorophenyl)-2-(2-phenyl-1-imidazolyl)-5- oxazolepropionic acid (yield: 29%) by reaction of 2-chloro-4-(4-chlorophenyl)-5-oxazolepropionic acid with 2-phenylimidazole. This was recrystallized from ethanol to give colorless needles. mp 179–180° C.

Example 28

In the same manner as in Example 24, obtained was 4-(4-chlorophenyl)-2-(1-pyrazolyl)-5-oxazolepropionic acid (yield: 91%) by reaction of 2-chloro-4-(4-chlorophenyl)-5-oxazolepropionic acid with pyrazole. This was recrystallized from methanol to give colorless needles. mp 171–172° C.

Example 29

In the same manner as in Example 24, obtained was 4-(4-chlorophenyl)-2-(1,2,4-triazol-1-yl)-5-oxazolepropionic acid (yield: 91%) by reaction of 2-chloro-4-(4-chlorophenyl)-5-oxazolepropionic acid with 1,2,4-triazole. This was recrystallized from ethanol to give colorless prisms. m.p. 168–169° C.

Example 30

Methyl 2-chloro-4-(4-chlorophenyl)-5-oxazolepropionate (1.50 g) and 2-propylimidazole (0.66 g) were dissolved in N,N-dimethylformamide (10 ml), and sodium hydride (60% dispersion in oil, 0.30 g) was gradually added to the resulting solution at room temperature. After this was stirred at room temperature for 3.5 hours, an aqueous solution of 2 N sodium hydroxide (50 ml) was added thereto and stirred for an additional 30 minutes. Water was added to the reaction mixture, and the pH was then adjusted to 6 with 2 N hydrochloric acid. The crystals thus precipitated were collected by filtration, and recrystallized from ethanol to obtain 4-(4-chlorophenyl)-2-(2-propyl-1-imidazolyl)-5-oxazolepropionic acid (1.25 g, 69%) as pale brown needles. mp 174–175° C.

Example 31

In the same manner as in Example 30, obtained was 4-(4-chlorophenyl)-2-(2-isopropyl-1-imidazolyl)-5-oxazolepropionic acid (yield: 59%) by reaction of methyl 2-chloro-4-(4-chlorophenyl)-5-oxazolepropionate with 2-isopropylimidazole followed by hydrolysis of the resulting product. This was recrystallized from ethyl acetate to give colorless prisms. mp 173–174° C.

Example 32

In the same manner as in Example 30, obtained was 4-(4-chlorophenyl)-2-(2-methylthio-1-imidazolyl)-5-oxazolep ropionic acid (yield: 87%) by reaction of methyl 2-chloro-4-(4-chlorophenyl)-5-oxazolepropionate with 2-methylthioimidazole followed by hydrolysis of the resulting product. This was recrystallized from chloroform-ethanol to give colorless needles. mp 225–226° C.

Example 33

In the same manner as in Example 30, obtained was 4-(4-chlorophenyl)-2-(4,5-dimethyl-1-imidazolyl)-5-oxazolepropionic acid (yield: 77%) by reaction of methyl 2-chloro-4-(4-chlorophenyl)-5-oxazolepropionate with 4,5-dimethylimidazole followed by hydrolysis of the resulting product. This was recrystallized from chloroform-methanol to give pale brown needles. mp 225–226° C.

Example 34

In the same manner as in Example 30, obtained was 4-(4-chlorophenyl)-2-(1-benzimidazolyl)-5-oxazolepropionic acid (yield: 82%) by reaction of methyl 2-chloro-4-(4-chlorophenyl)-5-oxazolepropionate with benzimidazole followed by hydrolysis of the resulting product. This was recrystallized from chloroform-methanol to give pale brown prisms. mp 217–218° C.

Example 35

In the same manner as in Example 30, obtained was 4-(4-chlorophenyl)-2-(3,5-dimethyl-1-pyrazolyl)-5-oxazolepropionic acid (yield: 90%) by reaction of methyl 2-chloro-4-(4-chlorophenyl)-5-oxazolepropionate with 3,5-dimethylpyrazole followed by hydrolysis of the resulting product. This was recrystallized from ethanol to give colorless needles. mp 201–202° C.

Example 36

Lithium aluminium hydride (185 mg) was gradually added to a tetrahydrofuran (20 ml) solution of 4-(4-chlorophenyl)-2-(2-methyl-1-imidazolyl)-5-oxazolepropionic acid (1.47 g) at room temperature. After the mixture was stirred for 1 hour, water (2 ml) was added to the reaction mixture with cooling with ice, and stirred for further 30 minutes. Diethyl ether (50 ml) was added to the reaction mixture, which was then dried ($MgSO_4$), and the insoluble substances were removed by filtration. The resulting filtrate was concentrated, and the crystals thus precipitated were collected by filtration to obtain 4-(4-chlorophenyl)-2-(2-methyl-1-imidazolyl)-5-oxazolepropanol (435 mg, 31%). This was recrystallized from dichloromethane-isopropyl ether to give colorless prisms. mp 128–129° C.

Example 37

In the same manner as in Example 36, obtained was 4-(4-chlorophenyl)-2-(1-pyrazolyl)-5-oxazolepropanol (yield: 33%) by reduction of 4-(4-chlorophenyl)-2-(1-pyrazolyl)-5-oxazolepropionic acid with lithium aluminium hydride. This was recrystallized from diethyl ether-hexane to give colorless prisms. mp 75–76° C.

Example 38

A toluene solution of diethyl azodicarboxylate (40%, 880 mg) was dropwise added to a tetrahydrofuran (10 ml) solution of 4-(4-chlorophenyl)-2-(2-methyl-1-imidazolyl)-5-oxazolepropanol (320 mg), 1,2,4-triazole (140 mg) and tributylphosphine (410 mg) at room temperature. After stirring for 1 hour, the reaction mixture was concentrated, and the residue was subjected to silica gel column chromatography. From the fraction eluted with acetone-hexane (2:1, v/v), obtained was 1-[3-[4-(4-chlorophenyl)-2-(2-methyl-1-imidazolyl)-5-oxazolyl]propyl]-1,2,4-triazole (305 mg, 82%). This was recrystallized from acetone-isopropyl ether to give colorless prisms. mp 142–143° C.

Example 39

In the same manner as in Example 38, obtained was 4-(4-chlorophenyl)-5-[3-(2-methoxyphenoxy)propyl]-2-(2-methyl-1-imidazolyl)oxazole (yield: 54%) by reaction of 4-(4-chlorophenyl)-2-(2-methyl-1-imidazolyl)-5-oxazolepropanol with 2-methoxyphenol. This was recrystallized from diethyl ether-hexane to give colorless needles. mp 84–85° C.

Example 40

In the same manner as in Example 38, obtained was 3-[3-[4-(4-chlorophenyl)-2-(2-methyl-1-imidazolyl)-5- oxazolyl]propyl]-1-methylhydantoin (yield: 77%) by reaction of 4-(4-chlorophenyl)-2-(2-methyl-1-imidazolyl)-5-oxazolepropanol with 1-methylhydantoin. This was recrystallized from acetone-isopropyl ether to give colorless prisms. mp 105–106° C.

Example 41

Ethyl chloroformate (395 mg) was dropwise added to a tetrahydrofuran (40 ml) solution of 4-(4-chlorophenyl)-2-(2-methyl-1-imidazolyl)-5-oxazolepropionic acid (1.00 g) and triethylamine (365 mg), at −30° C. After stirring for 40 minutes, the reaction mixture was added to a mixture of aqueous ammonia (28%, 30 ml) and tetrahydrofuran (10 ml) at 0° C., and then stirred at room temperature for 1 hour. Water was added to the reaction mixture, and the crystals thus precipitated were collected by filtration to obtain 4-(4-chlorophenyl)-2-(2-methyl-1-imidazolyl)-5-oxazolepropionamide (900 mg, 90%). This was recrystallized from methanol-ethyl acetate to give colorless needles. mp 215–216° C.

Example 42

Ethyl chloroformate (590 mg) was dropwise added to a tetrahydrofuran (40 ml) solution of 4-(4-chlorophenyl)-2-(2-methyl-1-imidazolyl)-5-oxazolepropionic acid (1.50 g) and triethylamine (550 mg), at −30° C. After stirring for 30 minutes, the reaction mixture was poured into a solution as prepared from 2-chloroethylamine hydrochloride (2.62 g), triethylamine (2.29 g) and N,N-dimethylformamide (20 ml), at 0° C., and then stirred at room temperature for 1 hour. The reaction mixture was poured into water, and the crystals thus precipitated were collected by filtration to obtain N-(2-chloroethyl)-4-(4-chlorophenyl)-2-(2-methyl-1-imidazolyl)-5-oxazolepropionamide (1.53 g, 86%). This was recrystallized from ethyl acetate-hexane to give colorless needles. mp 155–156° C.

Example 43

In the same manner as in Example 42, obtained was -N-(2-chloroethyl)-4-(4-chlorophenyl)-2-(l-imidazolyl)-5-oxazolepropionamide (yield: 77%) from 4-(4-chlorophenyl)-2-(l-imidazolyl)-5-oxazolepropionic acid. This was recrystallized from acetone-isopropyl ether to give colorless needles. mp 130–131° C.

Example 44

In the same manner as in Example 42, obtained was N-(2-chloroethyl)-4-(4-chlorophenyl)-2-(1,2,4-triazol-1-yl)-5-oxazolepropionamide (yield: 87%) from 4-(4-chlorophenyl)-2-(1,2,4-triazol-1-yl)-5-oxazolepropionic acid. This was recrystallized from ethyl acetate-isopropyl ether to give colorless needles. mp 157–158° C.

Example 45

Ethyl chloroformate (435 mg) was dropwise added to a tetrahydrofuran (30 ml) solution of 4-(4-chlorophenyl)-2-(2-pyridylthio)-5-oxazolepropionic acid (1.20 g) and triethylamine (405 mg), at −30° C. After stirring for 30 minutes, the reaction mixture was poured into a solution as prepared from 2-chloroethylamine hydrochloride (1.93 g), triethylamine (1.68 g) and N,N-dimethylformamide (20 ml), at 0° C., and stirred at room temperature for 1 hour. The reaction mixture was poured into water, and then extracted with ethyl acetate. The ethyl acetate layer was washed with water, and dried (MgSO4), and the solvent was evaporated. The resulting residue was subjected to silica gel column chromatography. From the fraction eluted with acetone-hexane (1:2, v/v), obtained was N-(2-chloroethyl)-4-(4-chlorophenyl)-2-(2-pyridylthio)-5-oxazolepropionamide (1.29 g, 91%) as an oily substance.

NMR (δ ppm in CDCl$_3$): 2.65(2H,t,J=7.5 Hz), 3.29(2H, t,J=7.5 Hz), 3.4–3.6(4 H,m), 6.24(1 H,brs), 7.21(1H,ddd,J= 7.5&5&1 Hz), 7.35–7.5(3 H,m), 7.6–7.75(3 H,m), 8.49(1H, dd,J=5&1 Hz).

Example 46

Sodium hydride (60% dispersion in oil, 265 mg) was gradually added to a solution of N-(2-chloroethyl)-4L(4-chlorophenyl)-2-(2-methyl-1-imidazolyl)-5-oxazolepropionamide (1.30 g) in N,N-dimethylformamide (30 ml), at room temperature. After stirring at room temperature for 3 hours, the reaction mixture was poured into ice water, and then extracted with ethyl acetate. The ethyl acetate layer was washed with water, and dried (MgSO4), and the solvent was evaporated. The crystals thus precipitated were collected by filtration to obtain 4-(4-chlorophenyl)-2-(2-methyl-1-imidazolyl)-5-[2-(2-oxazolin-2-yl)ethyl]oxazole (1.07 g, 91%). This was recrystallized from acetone-isopropyl ether to give colorless prisms. mp 119–120° C.

Example 47

In the same manner as in Example 46, obtained was 4-(4-chlorophenyl)-2-(1-imidazolyl)-5-[2-(2-oxazolin-2-yl) ethyl]oxazole (yield: 69%) by cyclization of N-(2-chloroethyl)-4-(4-chlorophenyl)-2-(1-imidazolyl)-5-oxazolepropionamide. This was recrystallized from acetone-isopropyl ether to give colorless prisms. mp 120–121° C.

Example 48

In the same manner as in Example 46, obtained was 1-[4-(4-chlorophenyl)-5-[2-(2-oxazolin-2-yl)ethyl]-2-oxazolyl]-1,2,4-triazole (yield: 85%) by cyclization of N-(2-chloroethyl)-4-(4-chlorophenyl)-2-(1,2,4-triazol-1-yl)-5-oxazolepropionamide. This was recrystallized from acetone-isopropyl ether to give colorless prisms. mp 132–133° C.

Example 49

In the same manner as in Example 46, N-(2-chloroethyl)-4-(4-chlorophenyl)-2-(2-pyridylthio)-5-oxazolepropionamide was cyclized, the reaction mixture was poured into water, and extracted, the resulting extract was washed with water and dried (MgSO$_4$), the solvent was evaporated, and the resulting residue was subjected to silica gel column chromatography. From the fraction eluted with acetone-hexane (1:2, v/v), obtained was 4-(4-chlorophenyl)-2-(2-pyridylthio)-5-(2-(2-oxazolin-2-yl)ethyl]oxazole as an oily substance (yield: 67%). NMR (δ ppm in CDCl$_3$): 2.65–2.8(2 H,m), 3.2–3.35(2 H,m), 3.80(2H,t,J=9.5 Hz), 4.21(2H,t,J=9.5 Hz), 7.16(1H,ddd,J=7.5&5&1 Hz), 7.35–7.45(3 H,m), 7.55–7.7 (3 H,m), 8.4(1H,ddd,J= 5&2&0.5 Hz).

Example 50

Ethyl chloroformate (450 mg) was dropwise added to a tetrahydrofuran (40 ml) solution of 4-(4-chlorophenyl)-2-(2-ethyl-1-imidazolyl)-5-oxazolepropionic acid (1.20 g) and triethylamine (420 mg), at −30° C. After stirring for 1 hour, the reaction mixture was poured into a solution as prepared from 2-chloroethylamine hydrochloride (2.01 g), triethylamine (1.76 g) and tetrahydrofuran (40 ml), at 0° C., and stirred at room temperature for 1.5 hours. The reaction mixture was poured into water and then extracted with ethyl acetate. The ethyl acetate layer was washed with water, and dried (with MgSO4), and the solvent was evaporated. The crystals (910 mg) thus precipitated were collected by filtration. The crystals were stirred along with potassium carbonate (370 mg) in N,N-dimethylformamide (20 ml) at 90 to 100° C. for 1.5 hours. The reaction mixture was poured into water, and extracted with ethyl acetate. The ethyl acetate layer was washed with water, and dried (MgSO$_4$), and the solvent was evaporated. The resulting residue was subjected to silica gel column chromatography. From the fraction eluted with acetone-hexane (2:3, v/v), obtained was 4-(4-chlorophenyl)-2-(2-ethyl-1-imidazolyl)-5-[2-(2-oxazolin-2-yl)ethyl]oxazole (320 mg, 25%). This was recrystallized from isopropyl ether to give colorless prisms. mp 53–54° C.

Example 51

In the same manner as in Example 50, obtained was 4-(4-chlorophenyl)-5-[2-(2-oxazolin-2-yl)ethyl]-2-(1-pyrazolyl)oxazole (yield: 42%) by reaction of 4-(4-chlorophenyl)-2-(1-pyrazolyl)-5-oxazolepropionic acid with 2-chloroethylamine followed by cyclization of the resulting product. This was recrystallized from acetone-isopropyl ether to give colorless needles. mp 79–80° C.

Example 52

A mixture of 4-(4-chlorophenyl)-2-(2-methyl-1-imidazolyl)-5-oxazolepropionic acid(500mg), potassium carbonate(310 mg), iodoethane(350mg) and N,N-dimethylformamide(10 ml) was stirred at room temperature for 16 hours. Water was added to the mixture, and the resulting mixture was extracted with ethyl acetate. The ethyl acetate layer was washed with water, and dried(MgSO$_4$). The solvent was evaporated and the 15 crystals thus precipitated were collected by filtration. These were recrystallized from acetone-hexane to give colorless of ethyl 4-(4-chlorophenyl)-2-(2-methyl-1-imidazolyl)-5-oxazolepropionate(495mg, 91%). mp 70–71° C.

Example 53

In the same manner as Example 52, obtained was benzyl 4-(4-chlorophenyl)-2-(2-methyl-1-imidazolyl) -5-oxazole propionate (yield: 88%) by reaction of 4-(4-chlorophenyl)-2-(2-methyl-1-imidazolyl)-5-oxazolepropionic acid with benzyl bromide. This was recrystallized from acetone-isopropyl ether to give colorless prisms. mp 71–72° C.

Example 54

In the same manner as Example 52, obtained was ethyl 4-(4-chlorophenyl)-2-(l-imidazolyl)-5-oxazolepropionate (yield: 92%) by reaction of 4-(4-chlorophenyl)-2-(1-imidazolyl)-5-oxazolepropionic acid 35 with iodoethane. This was recrystallized from acetone-isopropyl ether to give colorless prisms. mp 67–68° C.

Example 55

In the same manner as Example 52, obtained was ethyl 4-(4-chlorophenyl)-2-(1,2,4-triazol-1-yl)-5-oxazolepropionate (yield: 93%) by reaction of 4-(4-chlorophenyl)-2-(1,2,4-triazol-1-yl)-5-oxazolepropionic acid with iodoethane. This was recrystallized from acetone-isopropyl ether to give colorless prisms. mp 99–100° C.

Example 56

Water was added to a mixture which was obtained by ) reacting 4-(4-chlorophenyl)-2-(2-pyridylthio)-5-oxazolepropionic acid with iodoethane in the same manner as Example 52. This was extracted with ethyl acetate. The ethyl acetate layer was washed with water, and dried (MgSO4). The residue obtained by evaporated the solvent was subjected to silica gel column chromatography. From the fraction eluted with ethyl acetate-hexane (1:4, v/v), obtained was ethyl 4-(4-chlorophenyl)-2-(2-pyridylthio)-5-oxazolepropionate(yield: 96%) as an oily substance.

NMR(δ ppm in CDCl$_3$): 1.22(3H, t, J=7Hz), 2.74(2H, t, J=7.5Hz), 3.25(2H, t, J=7.5Hz), 4.12(2H, q, J=7Hz), 7.16 (1H, ddd, J=7.5&5&1Hz), 7.35–7.45(3H, m), 7.55–7.7(3H, m), 8.48(1H, ddd, J=5&2&1Hz).

Example 57

Lithium aluminum hydride (135mg) was gradually added to tetrahydrofuran solution (20ml) of ethyl 4-(4-chlorophenyl)-2-(l-imidazolyl)-5-oxazolepropionate (1.15g) at 0C. After the reaction mixture was stirred for 2 hours, water was added to the reaction mixture with cooling with ice. The insoluble material was removed by filtration, and then the filtrate was concentrated. The residue was subjected to silica gel column chromatography. From the fraction eluted with acetone-isopropyl ether (1:2, v/v), obtained was 4-(4-chlorophenyl)-2-(1-imidazolyl)-5-oxazolepropanol (690mg, 68%). This was recrystallized from acetone-isopropyl ether to give colorless prisms. mp 114–115° C.

Example 58

In the same manner as Example 57, obtained was 4-(4-chlorophenyl)-2-(1,2,4-triazol-1-yl)-5-oxazolepropanol (yield: 42%) by reduction of ethyl 4-(4-chlorophenyl)-2-(1,2,4-triazol-1-yl)-5-oxazolepropionate with lithium aluminum hydride. This was recrystallized from methanol-isopropyl ether to give colorless prisms. mp 139–140° C.

Example 59

In the same manner as Example 57, obtained was 4-(4-chlorophenyl)-2-(2-pyridylthio)-5-oxazolepropanol(yield: 81%) by reduction of ethyl 4-(4-chlorophenyl)-2-(2-pyridylthio)-5-oxazolepropionate with lithium aluminum hydride. This was recrystallized from diethyl ether-isopropyl ether to give colorless prisms. mp 70–71° C.

Example 60

A mixture of 4-(4-chlorophenyl)-5-(2-cyanoethyl)-2-(2-methyl-1-imidazolyl)oxazole (350mg), cysteamine (175mg) and 2-propanol was stirred under reflux for 24 hours. Water was added to the reaction mixture, and the resulting mixture was extracted with ethyl acetate. The ethyl acetate layer was washed with water, and dried (MgSO$_4$). The residue obtained by evaporating the solvent was subjected to silica gel column chromatography. From the fraction eluted with acetone-hexane (1:1, v/v), obtained was 4-(4-chlorophenyl)-2-(2-methyl-1-imidazolyl)-5-[2-(2-thiazolin-2-yl)ethyl] oxazole (320mg, 77%). This was recrystallized from acetone-isopropyl ether to give colorless prisms. mp 73–74° C.

Example 61

In the same manner as Example 1, obtained was methyl 2-chloro-4-(4-chlorophenyl)-5-oxazolebutyrate(yield: 69%) by reaction of methyl 4-[4-(4-chlorophenyl)-2-oxo-4-oxazolin-5-yl]butyrate with phosphorus oxychloride. This was recrystallized from acetone-isopropyl ether to give colorless prisms. mp 73–74° C.

Example 62

In the same manner as Example 2, obtained was 2-chloro-4-(4-chlorophenyl)-5-oxazolebutyric acid(yield: 76%) by hydrolysis of methyl 2-chloro-4-(4-chlorophenyl)--5-oxazolebutyrate. This was recrystallized from acetone-ethyl acetate to give colorless prisms. mp 150–151° C.

Example 63

In the same manner as Example 24, obtained was 4-(4-chlorophenyl)-2-(2-methyl-1-imidazolyl)-5-oxazole butanoic acid(yield: 76%) by reaction of 2-chloro-4-(4-chlorophenyl)-5-oxazolebutyric acid with 2-methylimidazole. This was recrystallized from tetrahydrofuran-methanol to give colorless prisms. mp 211–212° C.

Example 64

In the same manner as Example 52, obtained was ethyl 4-(4-chlorophenyl)-2-(2-methyl-1-imidazolyl)-5-oxazolebutyrate(yield: 88%) by reaction of 4-(4-chlorophenyl)-2-(2-methyl-1-imidazolyl)-5-oxazole butyric acid with iodoethane. This was recrystallized from acetone-isopropyl ether to give colorless prisms. mp 72–73° C.

Example 65

Lithium aluminum hydride (110 mg) was gradually added to a tetrahydrofuran solution (20ml) of ethyl 4-(4-chloroethyl)-2-(2-methyl-1-imidazolyl)-5-oxazolebutyrate (960mg) at 0° C. After the mixture was stirred for 2 hours, water was added to the reaction mixture with cooling with ice. The insoluble material was removed by filtration, and then the filtrate was concentrated to obtain 4-(4-chlorophenyl)-2-(2-methyl-1-imidazolyl)-5-oxazolebutanol (750mg, 88%). This was recrystallized from acetone-isopropyl ether to give colorless prisms. mp 110–111° C.

Example 66

Ethyl chloroformate (375mg) was added dropwise to a tetrahydrofuran (20ml)-N,N-dimethylformamide (10 ml) solution of 4-(4-chlorophenyl)-2-(2-methyl-1-imidazolyl)-5-oxazolebutanoic acid (1.00 g) and triethylamine at −30° C. After stirring for 30 minutes, the reaction mixture was added to the solution of 2-chloroethylamine (1.45g) and N,N-dimethylformamide (20ml) at QOC. The resulting mixture was stirred for 1 hour at room temperature. Water was poured into the reaction mixture to give N-(2-chloroethyl)-4-(4-chlorophenyl)-2-(2-methyl-1-imidazolyl)-5-oxazolebutyramide (1.00 g, 85%). This was recrystallized from ethyl acetate-hexane to give colorless needles. mp 131–132° C.

Example 67

Sodium hydride (60%, oil, 130mg) was gradually added to a N,N-dimethylformamide solution (30ml) of N-(2-chloroethyl)-4-(4-chlorophenyl)-2-(2-methyl-1-imidazolyl)-5-oxazolebutyramide (870mg) at room temperature. After stirring for 4 hours at room temperature, the reaction mixture was poured into ice water. And this was extracted with ethyl acetate. The ethyl acetate layer was washed with water and dried (MgSO,). 4-(4-chlorophenyl)-2-(2-methyl-1-imidazolyl)-5-[3-(2-oxazolin-2-yl)propyl] oxazole (615mg, 78%) was obtained by evaporating the solvent. This was recrystallized from acetone-isopropyl ether to give colorless prisms. mp 88–89° C.

Example 68

Triethylamine(505 mg) was added dropwise to a N,N-dimethylformamide solution of 4-(4-chlorophenyl)-2-(2-methyl-1-imidazolyl)-5-oxazolepropionic acid(1.50 g) and N,O-dimethylhydroxyamine hydrochloride(490 mg) at 0° C. 1-Hydroxybenzotriazole hydrate(HOBt, 760 mg) and 1-ethyl-3-(3-dimethylaminopropyl)carbodiimide hydrochloride(WSC, 950 mg) were added thereto. The reaction mixture was stirred for 20 hours at room temperature. Water was poured into the reaction mixture. Saturated sodium bicarbonate solution was added to make the mixture alkaline. The resulting mixture was extracted with ethyl acetate. The ethyl acetate layer was washed with water, and dried(MgSO$_4$). The solvent was evaporated, and the precipitated crystals were collected by filtration to give N-methoxy-N-methyl-4-(4-chlorophenyl)-2-(2-methyl-1-imidazolyl)-5-oxazolepropionamide(1.54 g, 91%). This was recrystallized from acetone-isopropyl ether to give colorless prisms. mp 116–117° C.

Example 69

A toluene solution of diisobutylaluminum hydride (DIBAL-H, 1.0 M, 8.5 ml) was added dropwise into a tetrahydrofuran solution (40 ml) of N-methoxy-N-methyl-4-(4-chlorophenyl)-2-(2-methyl-1-imidazolyl)-5-oxazolepropionamide(800 mg) at −70° C. After the reaction mixture was stirred for 3 hours, water was added to the reaction mixture. Acetic acid was added to make the mixture neutral. The resulting mixture was extracted with ethyl acetate. The ethyl acetate layer was washed with water, and dried(MgSO$_4$). The residue obtained by evaporating the solvent was subjected to silica gel column chlomatography. From the fraction eluted with ethyl acetate-hexane(1:3, v/v), obtained was 4-(4-chlorophenyl)-2-(2-methyl-1-imidazolyl)-5-oxazolepropionaldehyde(475 mg, 70%). This was recrystallized from acetone-isopropyl ether ro give colorless prisms. mp 109–110° C.

Example 70

A mixture of 4-(4-chlorophenyl)-2-(2-methyl-1-imidazolyl)-5-oxazolepropionaldehyde(220 mg), cysteamine(65 mg), p-toluensulfonic acid monohydrate(15 mg) and toluene(20 ml) was stirred for 1 hour under reflux. Ethyl acetate was added to the reaction mixture. The ethyl acetate layer was separated, washed with water and then with a saturated sodium bicarbonate solution, and dried (MgSO$_4$). The residue obtained by evaporating the solvent was subjected to silica gel column chlomatography. From the fraction eluted with acetone-hexane(2:1, v/v), obtained was 2-[2-[4-(4-chlorophenyl)-2-(2-methyl-1-imidazolyl)-5-oxazolyl]ethyl]thiazolidine (230 mg, 88%). This was recrystallized from acetone-isopropyl ether to give colorless prisms. mp 110–111° C.

Example 71

Methanesulfonyl chloride(215 mg) was added dropwise into a tetrahydrofuran solution(20 ml) of 4-(4-chlorophenyl)-2-(2-methyl-1-imidazolyl)-5-oxazolepropanol(200 mg) and triethylamine(190 mg) at room temperature. After the reaction mixture was stirred for 12 hours, water was added to the reaction mixture. The resulting mixture was extracted with ethyl acetate. The ethyl acetate layer was washed with water, and dried(MgSO$_4$). The residue obtained by evaporating the solvent was subjected to silica gel column chromatography. From the frac-

Example 72

A mixture of 3-[4-(4-chlorophenyl)-2-(2-methyl-1-imidazolyl)-5-oxazolyl]propyl methanesulfonate(400 mg), imidazole(140 mg), potassium carbonate(280 mg) and N,N-dimethylformamide(20 ml) was stirred for 2 hours at 100–110° C. Water was added to the reaction mixture. The resulting mixture was extracted with ethyl acetate. The ethyl acetate layer was washed with water, and dried($MgSO_4$). The residue obtained by evaporating the solvent was subjected to silica gel column chromatography. From the fraction eluted with methanol-chloroform(5:95, v/v), obtained was 4-(4-chlorophenyl)-5-[3-(1-imidazolyl)propyl]-2-(2-methyl-1-imidazolyl)oxazole(230 mg, 62%). This was recrystallized from acetone-isopropyl ether to give colorless prisms. mp 133–134° C.

Example 73

In the same manner as Example 72, obtained was 4-(4-chlorophenyl)-2-(2-methyl-1-imidazolyl)-5-[3-(1-pyrazolyl)propyl)oxazole (yield: 54%) by reaction of 3-[4-(4-chlorophenyl)-2-(2-methyl-1-imidazolyl)-5-oxazolyl] propyl methanesulfonate with pyrazole. This was recrystallized from acetone-isopropyl ether to give colorless prisms. mp 129–130° C.

Example 74

In the same manner as Example 38, obtained was 3-[3-[4-(4-chlorophenyl)-2-(2-methyl-1-imidazolyl)-5-oxazolyl] propyl]-2,4-oxazolidinedione(yield: 89%) by reaction of 4-(4-chlorophenyl)-2-(2-methyl-1-imidazolyl)-5-oxazolepropanol with 2,4-oxazolidinedione. This was recrystallized from acetone-isopropyl ether to give colorless prisms. mp 152–153° C.

Example 75

In the same manner as Example 38, obtained was 3-[3-[4-(4-chlorophenyl)-2-(2-methyl-1-imidazolyl)-5-oxazolyl] propyl]-2,4-thiazolydinedione(yield: 91%) by reaction of 4-(4-chlorophenyl)-2-(2-methyl-1-imidazolyl)-5-oxazolepropanol with 2,4-thiazolidinedione. This was recrystallized from ethyl acetate-hexane to give colorless needles. mp 119–120° C.

Example 76

In the same manner as Example 38, obtained was 3-[3-[4-(4-chlorophenyl)-2-(2-methyl-1-imidazolyl)-5-oxazolyl] propyl]hydantoin(yield: 65%) by reaction of 4-(4-chlorophenyl)-2-(2-methyl-1-imidazolyl)-5-oxazolepropanol with hydantoin. This was recrystallized from methanol-ethyl acetate to give colorless prisms. mp 197–198° C.

Example 77

A mixture of ethyl 2-[4-(4-chlorophenyl)-2-(2-methyl-1-imidazolyl)-5-oxazolyl]-2-hydroxyacetate(1.30 g) and thionyl chloride(3 ml) was stirred for 30 minutes at room temperature. The reaction mixture was concentrated. Saturated sodium bicarbonate was added to the residue, and the resulting mixture was extracted with ethyl acetate. The ethyl acetate layer was washed with water, and dried($MgSO_4$). The crystals(1.25 g) obtained by evaporating the solvent was collected by filtration. Zinc powder(5.0 g) was added to an acetic acid solution(10 ml) of the crystals(1.25 g). The resulting mixture was stirred for 1 hour at 100–110° C. The zinc powder was removed by filtration. The filtrate was concentrated. Saturated sodium bicarbonate was added to the residue, and the resulting mixture was extracted with ethyl acetate. The ethyl acetate layer was washed with water, and dried($MgSO_4$). The residue obtained by evaporating the solvent was subjected to silica gel column chromatography. From the fraction eluted with ethyl acetate-hexane(2:3, v/v), obtained was ethyl 4-(4-chlorophenyl)-2-(2-methyl-1-imidazolyl)-5-oxazole acetate(960 mg, 77%). This was recrystallized from acetone-isopropyl ether to give colorless prisms. mp 133–134° C.

Example 78

In the same manner as Example 57, obtained was 4-(4-chlorophenyl)-2-(2-methyl-1-imidazolyl)-5-oxazolethanol (yield: 48%) by reduction of ethyl 4-(4-chlorophenyl)-2-(2-methyl-1-imidazolyl)-5-oxazole acetate with lithium aluminum hydride. This was recrystallized from acetone-isopropyl ether to give colorless prisms. mp 159–160° C.

Example 79

A mixture of ethyl 5-[4-(4-chlorophenyl)-2-oxo-4-oxazolin-5-yl]pentanoate(17.2 g), phosphorus oxychloride (32.6 g) and pyridine(4.20 g) was stirred for 80 minutes at 120–130° C. The reaction mixture was poured into ice water, and extracted with ethyl acetate. The ethyl acetate layer was washed with water, and dried($MgSO_4$). The residue obtained by evaporating the solvent was subjected to silica gel column chlomatography. From the fraction eluted with ethyl acetate-hexane(1:3, v/v), obtained was ethyl 2-chloro-4-(4-chlorophenyl)-5-oxazolepentanoate as an oily substance (14.1 g, 78%).

NMR(δ ppm in $CDCl_3$): 1.25(3H, t, J=7Hz), 1.6–1.85(4H, m), 2.34(2H, t, J=6.5Hz), 2.86(2H, t, J=7Hz), 4.13(2H, q, J=7Hz), 7.39(2H, d, J=8.5Hz), 7.53(2H, d, J=8.5Hz).

Example 80

In the same manner as Example 79, obtained was ethyl 2-chloro-4-(4-chlorophenyl)-5-oxazolehexanoate as an oily substance (yield: 70%) by reaction of ethyl 6-[4-(4-chlorophenyl)-2-oxo-4-oxazolin-5-yl]hexanoate with phosphorus oxychloride.

NMR(δ ppm in $CDCl_3$): 1.25(3H, t, J=7Hz), 1.3–1.85(6H, m), 2.31(2H, t, J=7.5Hz), 2.85(2H, t, J=7.5Hz), 4.13(2H, q, J=7Hz), 7.39(2H, d, J=8.5Hz), 7.53(2H, d, J=8.5Hz).

Example 81

A mixture of ethyl 2-chloro-4-(4-chlorophenyl)-5-oxazolepentanoate(10.0 g), 2-methylimidazole(7.20 g), potassium carbonate(12.1 g) and N,N-dimethylformamide (80 ml) was stirred for 2 hours at 120–130° C. Water was added to the reaction mixture to give 30 ethyl 4-(4-chlorophenyl)-2-(2-methyl-1-imidazolyl)-5-oxazolepentanoate(9.97 g, 88%). This was recrystallized from ethyl acetate-isopropyl ether to give colorless prisms. mp 93–94° C.

Example 82

A mixture of ethyl 2-chloro-4-(4-chlorophenyl)-5-oxazolehexanoate(3.53 g), 2-methylimidazole(2.44 g), potassium carbonate(4.10 g) and N,N-dimethylformamide (50 ml) was stirred for 3 hours at 120–125° C. Water was added to the reaction mixture. The resulting mixture was extracted with ethyl acetate. The ethyl acetate layer was washed with water, and dried(MgSO$_4$). The residue obtained by evaporating the solvent was subjected to silica gel column chlomatography. From the fraction eluted with ethyl acetate-hexane(1:1, v/v), obtained was ethyl 4-(4-chlorophenyl)-2-(2-methyl-1-imidazolyl)-5-oxazolehexanoate as an oily substance(3.48 g, 87%).

NMR(δ ppm in CDCl$_3$): 1.25(3H, t, J=7Hz), 1.35–1.9(6H, m), 2.31(2H, t, J=7.5Hz), 2.77(3H, s), 2.91(2H, t, J=7.5Hz), 4.12(2H, q, J=7Hz), 7.01(1H, d, J=1.5Hz), 7.42(2H, d, J=8.5Hz), 7.48(1H, d, J=1.5Hz), 7.60(2H, d, J=8.5Hz).

Example 83

Lithium aluminum hydride(615 mg) was gradually added to a tetrahydrofuran solution(80 ml) of ethyl 4-(4-chlorophenyl)-2-(2-methyl-1-imidazolyl)-5-oxazolepentanoate(6.00 g) at 0° C. After the reaction mixture was stirred for 2 hours, water(1 ml) was added to the reaction mixture with cooling with ice, and the insoluble substance was removed by filtration. The filtrate was concentrated to give 4-(4-chlorophenyl)-2-(2-methyl-imidazolyl)-5-oxazolepentanol(4.20 g, 79%). This was recrystallized from ethyl acetate to give colorless prisms. mp 94–95° C.

Example 84

Lithium aluminum hydride(340 mg) was gradually added to a tetrahydrofuran solution(40 ml) of ethyl 4-(4-chlorophenyl)-2-(2-methyl-1-imidazolyl)-5-oxazolehexanoate(3.40 g) at 0° C. After the reaction mixture was stirred for 1 hour, water(1 ml) was added to the reaction mixture with cooling with ice, and the insoluble substance was removed by filtration. The filtrate was concentrated. The residue was subjected to silica gel chlomatography. From the fraction eluted with acetone-hexane(1:1, v/v), obtained was 4-(4-chlorophenyl)-2-(2-methyl-1-imidazolyl)-5-oxazolehexanol(2.74 g, 90%). This was recrystallized from acetone-isopropyl ether to give colorless prisms. mp 70–71° C.

Example 85

In the same manner as Example 71, obtained was 4-4-(4-chlorophenyl)-2-(2-methyl-1-imidazolyl)-5-oxazolyl] butyl methanesulfonate(yield: 85%) by reaction of 4-(4-chlorophenyl)-2-(2-methyl-1-imidazolyl)-5-oxazolebutanol with methanesulfonyl chloride. This was recrystallized from acetone-diethylether to give colorless prisms. mp 100–101° C.

Example 86

Methanesulfonyl chloride(1.43 g) was added dropwise to a tetrahydrofuran solution(40 ml) of 4-(4-chlorophenyl)-2-(2-methyl-1-imidazolyl)-5-oxazolepentanol(2.16 g) and triethylamine(1.26 g) at room temperature. After the reaction mixture was stirred for 2 hours, water was added to the reaction mixture. The resulting mixture was extracted with ethyl acetate. The ethyl acetate layer was washed with water, and dried(MgSO$_4$). The residue obtained by evaporating the solvent was subjected to silica gel column chlomatography. From the fraction eluted with acetone-hexane(1:1, v/v), obtained was 5-[4-(4-chlorophenyl)-2-(2-methyl-1-imidazolyl)-5-oxazolyl]pentyl methanesulfonate as an oily substance(2.47 g, 93%).

NMR(δ ppm in CDCl$_3$): 1.45–1.9(6H, m), 2.78(3H, s), 2.94(2H, t, J=7.5Hz), 3.00(3H, s), 4.24(2H, t, J=6Hz), 7.01(1H, d, J=1.5Hz), 7.43(2H, d, J=8.5Hz), 7.48(1H, d, J=1.5Hz), 7.60(2H, d, J=8.5Hz).

Example 87

In the same manner as Example 86, obtained was 6-[4-(4-chlorophenyl)-2-(2-methyl-1-imidazolyl)-5-oxazolyl] hexyl methanesulfonate as an oily substance(yield: 93%) by reaction of 4-(4-chlorophenyl)-2-(2-methyl-1-imidazolyl)-5-oxazolehexanol with methanesulfonyl chloride.

NMR(δ ppm in CDCl$_3$): 1.4–1.9(8H, m), 2.78(3H, s), 2.92(2H, t, J=7.5Hz), 3.00(3H, s), 4.23(2H, t, J=6.5Hz), 7.01(1H, d, J=1.5Hz), 7.43(2H, d, J=8.5Hz), 7.48(1H, d, J=1.5Hz), 7.61(2H, d, J=8.5Hz).

Example 88

Diethyl azodicarboxylate(260 mg) was added dropwise to a tetrahydrofuran solution(10 ml) of 4-(4-chlorophenyl)-2-(2-methyl-1-imidazolyl)-5-oxazolebutanol(330 mg), 1,2,4-triazole(105 mg) and tributylphosphine(300 mg) with cooling with ice. After stirring for 1 hour, the reaction mixture was concentrated. The residue was subjected to silica gel column chlomatography. From the fraction eluted with methanol-chloroform(5:95, v/v), obtained was 1-(4-[4-(4-chlorophenyl)-2-(2-methyl-1-imidazolyl)-5-oxazolyl]butyl] 1,2,4-triazole(205 mg, 54%). This was recrystallized from ethyl acetate-diethyl ether to give colorless prisms. mp 74–75° C.

Example 89

A mixture of 4-[4-(4-chlorophenyl)-2-(2-methyl-imidazolyl)-5-oxazolyl]butyl methanesulfonate(600 mg), imidazole(200 mg), potassium carbonate(405 mg) and N,N-dimethylformamide(10 ml) was stirred for 90 minutes at 100–110° C. Water was added to the reaction mixture. The resulting mixture was extracted with ethyl acetate. The ethyl acetate layer was washed with water, and dried(MgSO$_4$). The residue obtained by evaporating the solvent was subjected to silica gel column chromatography. From the fraction eluted with methanol-chloroform(3:97, v/v), obtained was 4-(4-chlorophenyl)-5-[4-(1-imidazolyl)butyl]-2-(2-methyl-1-imidazolyl)oxazole(310 mg, 55%). This was recrystallized from ethyl acetate-diethyl ether to give colorless prisms. mp 84–85° C.

Example 90

A mixture of 5-[4-(4-chlorophenyl)-2-(2-methyl-1-imidazolyl)-5-oxazolyl]pentyl methanesulfonate(2.20 g), imidazole(710 mg), potassium carbonate(1.43 g) and N,N-dimethylformamide(40 ml) was stirred for 3 hours at 80–90° C. Water was added to the reaction mixture. The resulting mixture was extracted with ethyl acetate. The ethyl acetate layer was washed with water, and dried(MgSO$_4$). The residue obtained by evaporated the solvent was subjected to silica gel column chromatography. From the fraction eluted with methanol-chloroform(3:97, v/v), obtained was 4-(4-chlorophenyl)-5-[5-(1-imidazolyl)pentyl]-2-(2-methyl-1-imidazolyl)oxazole(1.45 g, 71%). The oily substance(1.45 g) was dissolved in methanol(6 ml), and thereto a 4N-hydrochloric acid-ethyl acetate solution (2 ml) was added. Ethyl acetate was then added to the reaction mixture. The precipitated white powder was collected by filtration, and washed with ethyl acetate-acetone to give 4-(4-chlorophenyl)-5-[5-(1-imidazolyl)pentyl]-2-(2-methyl-1- imidazolyl)oxazole dihydrochloride monohydrate(1.47 g, 58%). mp 197–199° C.

Example 91

A mixture of 6-[4-(4-chlorophenyl)-2-(2-methyl-1-imidazolyl)-5-oxazolyl]hexyl methansulfonate(2.11 g), imidazole(660 mg), potassium carbonate(1.33 g) and N,N-dimethylformamide(40 ml) was stirred for 2 hours at 90–95° C. Water was added to the reaction mixture. The resulting mixture was extracted with ethyl acetate. The ethyl acetate layer was washed with water, and dried($MgSO_4$). The residue obtained by evaporating the solvent was subjected to silica gel column chromatography. From the fraction eluted with methanol-chloroform(3:97, v/v), obtained was 4-(4-chlorophenyl)-5-[6-(i-imidazolyl)hexyl]-2-(2-methyl-1-imidazolyl)oxazole(1.26 g, 64%). The oily substance (1.26 g) was dissolved in methanol(5 ml), and thereto a 4N-hydrochloric acid-ethyl acetate solution (1.7 ml) was added. The reaction mixture was concentrated. Ethyl acetate was added to the residue. The precipitated white powder was collected by filtration. This was recrystallized from methanol-acetone to give 4-(4-chlorophenyl)-5-[6-(1-imidazolyl)hexyl]-2-(2-methyl-1-imidazolyl)oxazole dihydrochloride hemihydrate(1.16 g, 49%). mp 171–173° C.

Example 92

A mixture of 4-[4-(4-chlorophenyl)-2-(2-methyl-1-imidazolyl)-5-oxazolyl]butyl methanesulfonate( 600 mg), ethyl 2-imidazolecarboxylate(410 mg), potassium carbonate (405 mg) and N,N-dimethylformamide (30 ml) was stirred for 2 hours at 80–90° C. Water was added to the reaction mixture. This was extracted with ethyl acetate. The ethyl acetate layer was washed with water and dried (Mg $SO_4$). The residue obtained by evaporating the solvent was subjected to silica gel column chromatography. From the fraction eluted with acetone-hexane (1:1, v/v), obtained was ethyl 1-[4-[4-(4-chlorophenyl)-2-(2-methyl-1-imidazolyl)-5-oxazolyl]butyl)-2-imidazolecarboxylate as crystals (460 mg, 69%). This was recrystallized from acetone-isopropyl ether to give colorless prisms. mp 134–135° C.

Formulation Example 1 (production of tablets):

| | |
|---|---|
| (1) 4-(4-Chlorophenyl)-2-(2-methyl-1-imidazolyl)-5-oxazolepropanol (compound produced in Example 36) | 30 g |
| (2) Lactose | 50 g |
| (3) Corn Starch | 15 g |
| (4) Carboxymethyl Cellulose | 44 g |
| (5) Magnesium Stearate | 1 g |
| 1000 tablets | 140 g |

All of (1), (2) and (3), and 30 g of (4) were kneaded with water, then dried in vacuum and granulated. To the resulting granules, added were 14 g of (4) and 1 g of (5), mixed and tabletted, using a tabletting machine, into tablets. Thus were produced 1000 tablets each containing 30 mg/tablet of (1).

Formulation Example 2 (production of tablets):

| | |
|---|---|
| (1) 4-(4-Chlorophenyl)-5-[2-(2-oxazolin-2-yl)ethyl]-2-(1-pyrazolyl)oxazole (compound produced in Example 51) | 100 g |
| (2) Lactose | 200 g |
| (3) Corn Starch | 55 g |
| (4) Carboxymethyl Cellulose | 44 g |
| (5) Magnesium Stearate | 1 g |
| 1000 tablets | 400 g |

All of (1), (2) and (3), and 30 g of (4) were kneaded with water, then dried in vacuum and granulated. To the resulting granules, added were 14 g of (4) and 1 g of (5), mixed and tabletted, using a tabletting machine, into tablets. Thus were produced 1000 tablets each containing 100 mg/tablet of (1).

INDUSTRIAL APPLICABILITY

The compounds (I) or their salts of the present invention have an excellent blood sugar-depressing effect and an insulin secretion-promoting effect, and are poorly toxic. The compounds (I) or their salts of the present invention are useful in insulin secretion promoting agents for diabetes, agents for arteriosclerosis, agents for hyperlipemia, depressors, and agents for diabetic complications (e.g., nephropathy, retinopathy, neuropathy).

What is claimed is:

1. A compound represented by the formula:

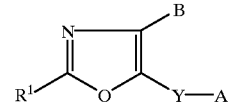

wherein $R^1$ is an optionally substituted heterocyclic group; A is an optionally substituted heterocyclic group; B is an optionally substituted aromatic group; Y is a divalent aliphatic hydrocarbon group; or a salt thereof.

2. A compound as claimed in claim 1, wherein the heterocyclic group for $R^1$ is:
   a 5- or 6-membered ring having as ring constituting atoms carbon atom(s) and 1 to 4 atoms selected from the group consisting of N, O and S as the, or
   a condensed ring comprising the 5- or 6-membered ring condensed with any of a 6-membered ring having 1 or 2 nitrogen ring-constituting atoms, a benzene ring or a 5-membered ring having one sulfur ring-constituting atom.

3. A compound as claimed in claim 1, wherein the heterocyclic group for $R^1$ is an azolyl group.

4. A compound as claimed in claim 1, wherein A is an optionally substituted heterocyclic group.

5. A compound as claimed in claim 4, where in the heterocyclic group is a 5- or 6-membered ring having 1 to 4 atoms selected from N, O and S as the ring-constituting atoms other than carbon atom(s), or a condensed ring comprising the 5- or 6-membered ring as condensed with any of a 6-membered ring having 1 or 2 nitrogen, a benzene ring or a 5-membered ring having one sulfur.

6. A compound as claimed in claim 4, wherein the heterocyclic group is an azolyl, azolinyl or azolidinyl group.

7. A compound as claimed in claim 1 or 4, wherein $R^1$ and A are independently selected from the group consisting of 2-pyridyl, 3-pyridyl, 4-pyridyl, 2-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-5-yl, 1,2,4-triazol-1-yl, 1,2,4-triazol-3-yl, 1,2,3-triazol-2-yl, 1,2,3-triazol-4-yl, tetrazol-1-yl, tetrazol-5-yl, benzimidazol-1-yl, benzimidazol-2-yl, indol-1-yl, indol-3-yl, 1H-indazol-1-yl, 1H-pyrrolopyrazin-1-yl, 1H-pyrrolopyridin-1-yl, 1H-imidazopyridin-1-yl, 1H-imidazopyridin-1-yl, 1H-imidazopyrazin-1-yl, 1-pyrrolidinyl, piperidino, morpholino, 1-piperazinyl, hexamethyleneimin-1-yl, oxazolidin-3-yl, thiazolidin-3-yl, imidazolidin-3-yl, imidazolin-1-yl, imidazolin-2-yl, oxazolin-2-yl, thiazolin-2-yl, oxazin-2-yl, 2-oxoimidazolidin-1-yl, 2,4-dioxoimidazolidin-3-yl, 2,4-dioxooxazolidin-3-yl and 2,4-dioxothiazolidin-3-yl group which may be substituted by 1 to 3 substitutents selected from the group consisting of an aliphatic hydrocarbon group, an alicyclic hydrocarbon group, an aryl group, an aromatic heterocyclic group, a non-aromatic heterocyclic group, halogen atom, nitro group, an optionally substituted amino group, an optionally substituted acyl group, an optionally substituted hydroxy group, an optionally substituted thiol group and an optionally esterified or amidated carboxy group.

8. A compound as claimed in claim 1, wherein $R^1$ is a pyridyl, pyrimidinyl, pyridazinyl, pyrazinyl, pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl, benzimidazolyl, indolyl, 1H-indazolyl, 1H-pyrrolopyrazinyl, 1H-pyrrolopyridyl, 1H-imidazopyridyl, 1H-imidazopyridyl, 1H-imidazopyrazinyl, pyrrolidinyl, piperidinyl, morpholinyl, piperazinyl, hexamethyleneiminyl, oxazolidinyl, thiazolidinyl, imidazolidinyl, imidazolinyl, oxazolinyl, thiazolinyl or oxazinyl group which may be substituted by 1 to 3 substituents selected from the group consisting of (i) a $C_{1-10}$ alkyl, $C_{2-10}$ alkenyl, or $C_{2-10}$ alkynyl group, (ii) a $C_{3-10}$ cycloalkyl, $C_{3-10}$ cycloalkenyl, or $C_{4-10}$ cycloalkadienyl group, (iii) a $C_{6-14}$ aryl group, (iv) a furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl, or 1,2,4-triazolopyridazinyl group, (v) an oxiranyl, azetidinyl, oxetanyl, thietanyl, tetrahydrofuryl, thioranyl, piperidyl, tetrahydropyranyl, morpholinyl, thiomorpholinyl, piperazinyl or pyrrolidinyl group, wherein each of said groups (ii), (iii), (iv) and (v) may be substituted by 1 to 3 substituents selected from the group consisting of $C_{1-6}$ alkyl, $C_{2-6}$ alkenyl, $C_{2-6}$ alkynyl, $C_{3-7}$ cycloalkyl, $C_{6-14}$ aryl, thienyl, furyl, pyridyl, oxazolyl, thiazolyl, tetrahydrofuryl, morpholino, piperidino, pyrrolidino, piperazino, $C_{7-9}$ aralkyl, amino, N-mono-$C_{1-4}$ alkylamino, N,N-di-$C_{1-4}$ alkylamino, $C_{2-8}$, acylamino, amidino, $C_{2-8}$ acyl, carbamoyl, N-mono-$C_{1-4}$ alkyl-carbamoyl, N,N-di-$C_{1-4}$ alkyl-carbamoyl, sulfamoyl, N-mono-$C_{1-4}$ alkylsulfamoyl, N,N-di-$C_{1-4}$ alkylsulfamoyl, carboxy, $C_{1-7}$ alkoxy-carbonyl, hydroxy, $C_{1-4}$ alkoxy, $C_{2-5}$ alkenyloxy, $C_{3-7}$ cyloalkyloxy, $C_{7-9}$ aralkyloxy, $C_{6-14}$ aryloxy, mercapto, $C_{1-4}$ alkylthio, $C_{7-9}$ aralkylthio, $C_{6-14}$ arylthio, sulfo, cyano, azido, nitro, nitroso and halogen, (vi) halogen atom, (vii) nitro group, (viii) an amino group which may be substituted by 1 or 2 substituents selected from the group consisting of $C_{1-10}$ alkyl, $C_{2-10}$ alkenyl, $C_{3-10}$ cycloalkyl, $C_{1-10}$ acyl and $C_{6-12}$ aryl, (ix) a $C_{1-13}$ acyl group which may be substituted by a $C_{1-3}$ alkyl, $C_{1-3}$ alkoxy, halogen, nitro, hydroxy or amino, (x) a hydroxy group, a $C_{1-10}$ alkoxy group, a $C_{2-10}$ alkenyloxy group, a C7–10 aralkyloxy group, a $C_{2-13}$ acyloxy group, a $C_{6-14}$ aryloxy group which may be substituted by 1 or 2 halogen or $C_{1-4}$ alkoxy, a $C_{1-10}$ alkylsulfonyloxy group or a $C_{6-12}$ arylsulfonyloxy group which may be substituted by a $C_{1-6}$ alkyl, (xi) a mercapto or $C_{1-10}$ alkylthio group which may be substituted by a furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl or 1,2,4-triazolopyridazinyl, a $C_{6-14}$ arylthio group which may be substituted by $C_{1-6}$ alkyl, a $C_{7-10}$ aralkylthio group, or a $C_{2-13}$ acylthio group, (xii) a carboxy group, a $C_{1-4}$ alkoxy-carbonyl group, a $C_{7-9}$ aralkyloxy-carbonyl group, a $C_{6-14}$ aryloxy-carbonyl group, or a $C_{1-4}$ alkoxy-carbonyl group substituted by a furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl; phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl or 1,2,4-triazolopyridazinyl, (xiii) a group of the formula: —CON($R^5$)($R^6$) wherein $R^5$ and $R^6$ independently are a hydrogen; a $C_{1-10}$ alkyl, $C_{2-10}$ alkenyl or $C_{2-10}$ alkynyl; a $C_{3-10}$ cycloalkyl, $C_{3-10}$ cycloalkenyl, $C_{4-10}$ cycloalkadienyl, $C_{6-14}$ aryl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl, or 1,2,4-triazolopyridazinyl group which may be substituted by 1 to 3 substituents selected from the group consisting of $C_{1-6}$ alkyl, $C_{2-6}$ alkenyl, $C_{2-6}$ alkynyl, $C_{3-7}$ cycloalkyl, $C_{6-14}$ aryl, thienyl, furyl, pyridyl, oxazolyl, thiazolyl, tetrahydrofuryl, morpholino, piperidino, pyrrolidino, piperazino, $C_{7-9}$ aralkyl, amino, N-mono-$C_{1-4}$ alkylamino, N,N-di-$C_{1-4}$ acylamino, $C_{2-8}$ acylamino, amidino, $C_{2-8}$ acyl, carbamoyl, N-mono-$C_{1-4}$ alkylcarbamoyl, N,N-di-$C_{1-4}$ alkylcarbamoyl, sulfamoyl, N-mono-$C_{1-4}$ alkylsulfamoyl, N,N-di-$C_{1-4}$ alkylsulfamoyl, carboxy, $C_{2-8}$ alkoxycarbonyl, hydroxy, $C_{1-4}$ alkoxy, $C_{2-5}$ alkenyloxy, $C_{3-7}$ cyloalkyloxy, $C_{7-9}$ aralkyloxy, $C_{6-14}$ aryloxy, mercapto, $C_{1-4}$ alkylthio, $C_{7-9}$ aralkylthio, $C_{6-14}$ arylthio, sulfo, cyano, azido, nitro, nitroso and halogen; or a hydroxy, $C_{1-10}$ alkoxy, $C_{2-10}$ alkenyloxy, $C_{7-10}$ aralkyloxy, $C_{2-13}$ acyloxy, $C_{6-14}$ aryloxy which may be substituted by 1 or 2 halogen or $C_{1-4}$ alkoxy or $C_{1-10}$ alkylsulfonyloxy group, and (xiv) an oxo group.

9. A compound as claimed in, claim 1, wherein A is a pyridyl, pyrimidinyl, pyridazinyl, pyrazinyl, pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl, benzimidazolyl, indolyl, 1H-indazolyl, 1H-pyrrolopyrazinyl, 1H-pyrrolopyridyl, 1H-imidazopyridyl, 1H-imidazopyridyl, 1H-imidazopyrazinyl, pyrrolidinyl, piperidinyl, morpholinyl, piperazinyl, hexamethyleneiminyl, oxazolidinyl, thiazolidinyl, imidazolidinyl, imidazolinyl, oxazolinyl, thiazolinyl or oxazinyl group which may be substituted by 1 to 3 substituents selected from the group consisting of (i) a $C_{1-10}$ alkyl, $C_{2-10}$ alkenyl, or $C_{2-10}$ alkynyl group, (ii) a $C_{3-10}$ cycloalkyl, $C_{3-10}$ cycloalkenyl, or $C_{4-10}$ cycloalkadienyl group, (iii) a $C_{6-14}$ aryl group, (iv) a furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl, or 1,2,4-triazolopyridazinyl group, (v) an oxiranyl, azetidinyl, oxetanyl, thietanyl, tetrahydrofuryl, thioranyl, piperidyl, tetrahydropyranyl, morpholinyl, thiomorpholinyl, piperazinyl or pyrrolidinyl group, and each of said groups (ii), (iii), (iv) and (v) may be substituted by 1 to 3 substituents selected from the group consisting of $C_{1-6}$ alkyl, $C_{2-6}$ alkenyl, $C_{2-6}$ alkynyl, $C_{3-7}$ cycloalkyl, $C_{6-14}$ aryl, thienyl, furyl, pyridyl, oxazolyl, thiazolyl, tetrahydrofuryl, morpholino, piperidino, pyrrolidino, piperazino, $C_{7-9}$ aralkyl, amino, N-mono-$C_{1-4}$ alkylamino, N,N-di-$C_{1-4}$ alkylamino, $C_{2-8}$ acylamino, amidino, $C_{2-8}$ acyl, carbamoyl, N-mono-C1-4 alkyl-carbamoyl, N,N-di-$C_{1-4}$ alkyl-carbamoyl, sulfamoyl, N-mono-$C_{1-4}$ alkylsulfamoyl, N,N-di-$C_{-4}$ alkylsulfamoyl, carboxy, $C_{1-7}$ alkoxycarbonyl, hydroxy, $C_{1-4}$ alkoxy, $C_{2-5}$ alkenyloxy, $C_{3-7}$ cyloalkyloxy, $C_{7-9}$ aralkyloxy, $C_{6-14}$ aryloxy, mercapto, $C_{1-4}$ alkylthio, $C_{7-9}$ aralkylthio, $C_{6-14}$ arylthio, sulfo, cyano, azido, nitro, nitroso and halogen, (vi) halogen atom, (vii) nitro group, (viii) an amino group which may be substituted by 1 or 2 substituents selected from the group consisting of $C_{1-10}$ alkyl, $C_{2-10}$ alkenyl, $C_{3-10}$ cycloalkyl, $C_{1-10}$ acyl and $C_{6-12}$ aryl, (ix) a $C_{1-13}$ acyl group which may be substituted by a $C_{1-3}$ alkyl, $C_{1-3}$ alkoxy, halogen, nitro, hydroxy or amino, (x) a hydroxy group, a $C_{1-10}$ alkoxy group, a $C_{2-10}$ alkenyloxy group, a $C_{7-10}$ aralkyloxy group, a $C_{2-13}$ acyloxy group, a $C_{6-14}$ aryloxy group which may be substituted by 1 or 2 halogen or $C_{1-4}$ alkoxy, a $C_{1-10}$ alkylsulfonyloxy group or a $C_{6-12}$ arylsulfonyloxy group which may be substituted by a $C_{1-6}$ alkyl, (xi) a mercapto or $C_{1-10}$ alkylthio group which may be substituted by a furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-cabolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl or 1,2,4-triazolopyridazinyl, a $C_{6-14}$ arylthio group which may be substituted by $C_{1-6}$ alkyl, a $C_{7-10}$ aralkylthio group, or $C_{2-13}$ acylthio group, (xii) a carboxy, a $C_{1-14}$ alkoxy-carbonyl group, a $C_{7-9}$ aralkyloxy-carbonyl group, a $C_{6-14}$ aryloxy-carbonyl group, or a $C_{1-4}$ alkoxy-carbonyl group substituted by a furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl or 1,2,4-triazolopyridazinyl, (xiii) a group of the formula: —CON($R^5$)($R^6$) wherein $R^5$ and $R^6$ independently are a hydrogen, a $C_{1-10}$ alkyl, $C_{2-10}$ alkenyl or $C_{2-10}$ alkynyl or a $C_{3-10}$ cycloalkyl, $C_{3-10}$ cycloalkenyl, $C_{4-10}$ cycloalkadienyl, $C_{6-14}$ aryl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyrdyl, imidazopyridazinyl, imidazopyrimidinyl, 1,2,4-triazolopyridyl, or 1,2,4-triazolopyridazinyl group which may be substituted by 1 to 3 substituents selected from the group consisting of $C_{1-6}$ alkyl, $C_{2-6}$ alkenyl, $C_{2-6}$ alkynyl, $C_{3-7}$ cycloalkyl, $C_{6-14}$ aryl, thienyl, furyl, pyridyl, oxazolyl, thiazolyl, tetrahydrofuryl, morpholino, piperidino, pyrrolidino, piperazino, $C_{7-9}$ aralkyl, amino, N-mono-$C_{1-4}$ alkylamino, N,N-di-$C_{1-4}$ alkylamino, $C_{2-8}$ acylamino, amidino, $C_{2-8}$ acyl, carbamoyl, N-mono-$C_{1-4}$ alkylcarbamoyl, N,N-di-$C_{1-4}$ alkylcarbamoyl, sulfamoyl, N-mono-$C_{1-4}$ alkylsulfamoyl, N,N-di-$C_{1-4}$ alkylsulfamoyl, carboxy, $C_{2-8}$ alkoxycarbonyl, hydroxy, $C_{1-4}$ alkoxy, $C_{2-5}$ alkenyloxy, $C_{3-7}$ cyloalkyloxy, $C_{7-9}$ aralkyloxy, $C_{6-14}$ aryloxy, mercapto, $C_{1-4}$ alkylthio, $C_{7-9}$ aralkylthio, $C_{6-14}$ arylthio, sulfo, cyano, azido, nitro, nitroso and halogen; or a hydroxy, $C_{1-10}$ alkoxy, $C_{2-10}$ alkenyloxy, $C_{7-10}$ aralkyloxy, $C_{2-13}$ acyloxy, $C_{6-14}$ aryloxy which may be substituted by 1 or 2 halogen or $C_{1-4}$ alkoxy, or $C_{1-10}$ alkylsulfonyloxy group.

10. A compound as claimed in claim 1, wherein B is a $C_{6-14}$ aryl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolidinyl, pyrrolopyridazinyl, pyrazolopyridyl, imidazopyridyl, imidazopyridyl, imidazopyridazinyl, imidazopyrimidinyl, 1,2,4-triazolopyridyl, or 1,2,4-triazolopyridazinyl group which may be substituted by 1 to 3 substituents selected from the group consisting of halogen, nitro, cyano, $C_{1-6}$ alkoxy which may be substituted by 1 to 3 halogen, hydroxy or $C_{1-6}$ alkoxy, $C_{1-6}$ alkyl which may be substituted by 1 to 3 halogen, hydroxy or $C_{1-6}$ alkoxy, $C_{3-7}$ cycloalkyl which may be substituted by 1 to 3 halogen, hydroxy or $C_{1-6}$ alkoxy.

11. A compound as claimed in claim 1, wherein Y is a divalent aliphatic hydrocarbon group having 1 to 7 carbon atoms.

12. A compound as claimed in claim 1, wherein Y is a divalent aliphatic hydrocarbon group having 2 to 4 carbon atoms.

13. A compound as claimed in claim 1, wherein $R^1$ is an imidazolyl, pyrazolyl, 1,2,4-triazolyl, 1,2,3-triazolyl, benzimidazolyl, pyrrolidinyl, piperidinyl, morpholinyl, or hexamethyleneiminyl group which may be substituted by 1 to 3 substituents selected from the group consisting of $C_{1-10}$ alkyl, $C_{6-14}$ aryl and $C_{1-10}$ alkylthio, A is an imidazolyl, pyrazolyl, 1,2,4-triazolyl, 1,2,3-triazolyl, thiazolidinyl, oxazolinyl, thiazolinyl, 2,4-dioxoimidazolidinyl, 2,4-dioxooxazolidinyl or 2,4-dioxothiazolidinyl group which may be substituted by a $C_{1-10}$ alkyl;

B is a phenyl group which may be substituted by a halogen; Y is -($CH_2$)$_2$-, -($CH_2$)$_3$-, -($CH_2$)$_4$-, -($CH_2$)$_5$- or -($CH_2$)$_6$-.

14. A compound as claimed in claim 1, wherein A is an optionally substituted heterocyclic group; and Y is a divalent aliphatic hydrocarbon group having 1 to 7 carbon atoms.

15. A compound as claimed in claim 14, wherein each of the heterocyclic group represented by $R^1$ and A is an azolyl group, an azolinyl group or an azolidinyl group.

16. A compound as claimed in claim 6, wherein the heterocyclic group represented by $R^1$ is an azolyl group, and the heterocyclic group represented by A is an azolyl group, an azolinyl group or an azolidinyl group.

17. A compound as claimed in claim 14, wherein $R^1$ and A are independently a pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl, pyrrolidinyl, oxazolidinyl, thiazolidinyl, imidazolidinyl, imidazolinyl, oxazolinyl or thiazolinyl group which may be substituted by 1 to 3 substituents selected from the group consisting of $C_{1-10}$ alkyl, $C_{6-14}$ aryl, $C_{1-10}$ alkylthio and oxo.

18. A compound as claimed in claim 14, wherein $R^1$ is an azolyl group which may be substituted by 1 to 3 substituents selected from the group consisting of $C_{1-10}$ alkyl, $C_{6-14}$ aryl and $C_{1-10}$ alkylthio.

19. A compound as claimed in claim 18, wherein the azolyl group is an imidazolyl, pyrazolyl, 1,2,4-triazolyl, or 1,2,3-triazolyl group.

20. A compound as claimed in claim 14, wherein A is an azolyl, azolinyl or azolidinyl group which may be substituted by 1 or 2 $C_{1-10}$ alkyl or oxo.

21. A compound as claimed in claim 14, wherein A is an imidazolyl, pyrazolyl, 1,2,4-triazolyl, 1,2,3-triazolyl, thiazolidinyl, oxazolinyl, thiazolinyl, 2,4-dioxoimidazolidinyl, 2,4-dioxooxazolidinyl or 2,4-dioxothiazolidinyl group which may be substituted by a $C_{1-10}$ alkyl.

22. A compound as claimed in claim 14, wherein B is an optionally substituted phenyl group.

23. A compound as claimed in claim 14, wherein B is a phenyl group which may be substituted by a halogen.

24. A compound as claimed in claim 14, wherein Y is a divalent aliphatic hydrocarbon group having 3 to 5 carbon atoms.

25. A compound as claimed in claim 14, wherein Y is -(CH$_2$)$_3$-, -(CH$_2$)$_4$- or -(CH$_2$)$_5$-.

26. A compound as claimed in claim 1, which 4-(4-chlorophenyl)-5-[3-(1-imidazolyl)propyl]-2-(2-methyl-1-imidazolyl)oxazole or its salt.

27. A compound as claimed in claim 1, which 4-(4-chlorophenyl)-5-(4-(1-imidazolyl)butyl]-2-(2-methyl-1-imidazolyl)oxazole or its salt.

28. A process for producing a compound represented by the formula:

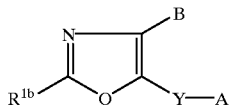

wherein $R^{1b}$ is an optionally substituted heterocyclic group and the other symbols are of the same meanings as defined in claim 1, or a salt thereof, which comprises reacting a compound represented by the formula:

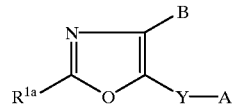

wherein $R^{1a}$ is a halogen atom, or a salt thereof with a compound represented by the formula:

$R^{1b}$-H or a salt thereof.

29. A pharmaceutical composition comprising a compound as claimed in claim 1.

30. A composition as claimed in claim 29, which is an insulin secretion-promoting agent.

31. A composition as claimed in claim 29, which is an agent preventing and treating for diabetes.

32. A compound as claimed in claim 1, wherein $R^1$ is 2-methyl-1-imidazolyl.

33. A compound as claimed in claim 1, wherein B is 4-chlorophenyl.

34. A compound as claimed in claim 32, wherein B is 4-chlorophenyl.

35. A compound as claimed in claim 1, wherein Y is propylene.

36. A compound as claimed in claim 33, wherein Y is propylene.

37. A method for manufacturing a medicament for the prophylaxis or treatment of diabetes, comprising selecting a compound according to claim 1 and admixing said compound with a pharmaceutically acceptable excipient.

38. A method for preventing or treating diabetic complications in a mammal in need thereof, which comprises administering to said mammal an effective amount of a compound as claimed in claim 1.

39. A compound as claimed in claim 34, wherein Y is propylene.

* * * * *

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

Column 3,
Lines 31 and 37, "an" should be deleted;
Line 57, "perferably" should read -- preferable --.

Column 4,
Line 56, "arylsulfonyloxy" should read -- arylsulfonyloxy group --.

Column 5,
Line 19, "group." should read -- groups. --;
Line 32, "heteroarylalkyloxycarbonyl." should read
-- heteroarylalkyloxycarbonyl group. --;
Line 42, "as" should read -- as, --;
Line 61, "includes," should read -- include, --.

Column 6,
Line 4, "$R_6$ the" should read -- $R^6$, the --;
Line 66, "as for" should read -- as, for --.

Column 8,
Line 43, "preferable" should read -- preferably --;
Line 46, "a" should read -- an --;
Line 48, "morphorinyl" should read -- morpholinyl --.

Column 10,
Line 12, "-(CH$_2$)4-" should read -- -(CH$_2$)$_4$- --;
Line 51, "sugar" should read -- sugar- --.

Column 13,
Line 33, "herein above" should read -- hereinabove --.

Column 16,
Line 48, "aluminium" should read -- aluminum --;
Line 62, "The" should read -- ¶ The --.

Column 17,
Line 46, "transfer" should read -- transfer, --.

Column 22,
Line 27, "to" should be deleted.

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

Column 23,
Line 29, "iron," should read -- iron or --;
Line 35, "extration," should read -- extraction, --.

Column 24,
Line 26, "reducting" should read -- reducing --.

Column 25,
Lines 4 and 41, "extration," should read -- extraction, --;

Column 26,
Line 10, "extration," should read -- extraction, --;
Line 58, "aluminium" should read -- aluminum --.

Column 28,
Line 3, "temperature" should read -- time --;
Line 57, "hologen)" should read -- halogen) --.

Column 29,
Line 14, "ranges" should read -- ranges from --.

Column 30,
Line 17, "table 1," should read -- Table 1, --;
Lines 29 and 30, "with" should be deleted.

Column 34,
Line 63, "needls." should read -- needles. --.

Column 35,
Line 3, close up right margin;
Line 4, close up left margin;
Line 5, "prisms" should read -- prisms. --.

Column 37,
Line 30, "an" should be deleted.

Column 39,
Line 50, "oxazolep ropionic" should read -- oxazolepropionic --.

Column 40,
Lines 17 and 37, "aluminium" should read -- aluminum --.

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

Column 41,
Line 41, "-N-" should read -- N- --.

Column 42,
Line 13, "-4L" should read -- -4- --.

Column 43,
Line 5, "MgSO4)," should read -- MgSO$_4$), --;
Line 35, "15" should be deleted;
Line 37, "colorless" should read -- colorless prisms --;
Line 53, "35" should be deleted;
Line 66, ")" should be deleted.

Column 44,
Line 4, "(MgSO4)." should read -- MgSO$_4$). -- and "evaporated" should read -- evaporating --;
Line 18, "OC." should read -- 0ºC --.

Column 45,
Line 3, close up right margin;
Line 4, close up left margin;
Line 5, "--5-" should read -- -5- --;
Line 46, "QOC." should read -- 0ºC. --;
Line 63, "MgSO,)." should read -- MgSO$_4$). --.

Column 46,
Line 37, "ro" should read -- to --.

Column 48,
Line 35, "chlomatography." should read -- chromatography. --;
Line 59, "30" should be deleted.

Column 49,
Lines 7 and 37, "chlomatography." should read -- chromatography. --;
Line 45, "4-4-" should read -- 4-[4- --;
Line 50, "acetone-diethylether" should read -- acetone-diethyl ether --;
Line 63, "chlomatography." should read -- chromatography. --.

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

Column 50,
Line 25, "chlomatography." should read -- chromatography. --;
Line 26, "1-(4-" should read -- 1-[4- --;
Line 57, "evaporated" should read -- evaporating --.

Column 51,
Line 34, "(Mg SO$_4$)." should read -- (MgSO$_4$). --.

Column 52,
Line 18, "are poorly toxic" should read -- exhibit low toxicity --;
Line 20, "secretion promoting" should read -- secretion-promoting --;
Line 42, "S as the," should read -- S, --;
Line 52, "where in" should read -- wherein --.

Column 53,
Line 5, "1H-pyrrolopyrazin-" should read -- 1H-pyrrolo[2,3-b]pyrazin- --;
Line 6, "1H-pyrrolopyridin-1-yl, 1H-imidazopyridin-1-yl," should read
-- 1H-pyrrolo[2,3-b]pyridin-1-yl, 1H-imidazo[4,5-b]pyridin-1-yl, --;
Line 7 should read -- 1H-imidazo[4,5-c]pyridin-1-yl, 1H-imidazo[4,5-b]pyrazin-1-yl, --;
Line 28 should read -- 1H-pyrrolo[2,3-b]pyrazinyl, 1H-pyrrolo[2,3-b]pyridyl, --;
Line 29 should read -- 1H-imidazo[4,5-b] pyridyl, 1Himidazo[4,5-c]pyridyl, --;
Line 30, "1H-imidazopyrazinyl," should read -- 1H-imidazo[4,5-b]pyrazinyl, --;
Line 46, "benzothienyl," should read -- benzo[b]thienyl, --;
Line 55, "pyrrolopyridazinyl," should read -- pyrrolo[1,2-b]pyridazinyl, --;
Line 56 should read -- pyrazolo[1,5-a]pyridyl, imidazo[1,2-a]pyridyl, imidazo[1,5-a] pyridyl, --;
Line 57 should read -- imidazo[1,2-b] pyridazinyl, imidazo[1,2-a]pyrimidinyl, 1,2,4 --;
Line 58, "triazolopyridyl, or 1,2,4-triazolopyridazinyl"
should read -- triazolo[4,3-a]pyridyl, or 1,2,4-triazolo[4,3-b]pyridazinyl --.

Column 54,
Line 4, "C$_{2-8}$, acylamino," should read -- C$_{2-8}$ acylamino, --;
Line 23, "C7-10" should read -- C$_{7-10}$ --;
Line 37, "benzothienyl," should read -- benzo[b]thienyl, --;
Line 46, "pyrrolopyridazinyl," should read -- pyrrolo[1,2-b] pyidazinyl, --;
Line 47 should read -- pyrazolo[1,5-a]pyridyl, imidazo[1,2-a]pyridyl, imidazo[1,5-a] pyridyl, --;
Line 48, should read -- imidazo[1,2-b]pyridazinyl, imidazo[1,2-a]pyrimidinyl, 1,2,4- --;
Line 49, "triazololpyridyl or 1,2,4-triazolopyridazinyl," should read -- triazolo[4,3-a] pyridyl or 1,2,4-triazole[4,3-b]pyridazinyl, --;
Line 62, "benzothienyl," should read -- benzo[b]thienyl, --.

UNITED STATES PATENT AND TRADEMARK OFFICE
CERTIFICATE OF CORRECTION

PATENT NO.    : 6,177,452 B1
DATED         : January 23, 2001
INVENTOR(S)   : Yu Momose et al.

It is certified that error appears in the above-identified patent and that said Letters Patent is hereby corrected as shown below:

Column 55,
Lines 4 and 27, "pyrrolopyridazinyl," should read -- pyrrolo[1,2-b]pyridazinyl, --;
Lines 5 and 28, should read -- pyrazolo[1,5-a]pyridyl, imidazo[1,2-a]pyridyl, imidazo [1,5-a]pyridyl, --;
Lines 6 and 29, should read -- imidazo[1,2-b]pyridazinyl, imidazo [1,2-a]pyrimidinyl, 1,2,4- --;
Lines 7 and 30, "triazolopyidyl or 1,2,4-triazolopyridazinyl," should read -- triazolo[4,3-a]pyridyl or 1,2,4-triazole[4,3-b]pyridazinyl, --.
Line 18, "benzothienyl," should read -- benzo[b]thienyl, --;
Line 23, "phthalazinyl" should read -- phthalazinyl, --;
Line 42, "cyloalkyloxy," should read -- cycloalkyloxy, --;
Line 50, "in," should read -- in --;
Line 55, should read -- 1H-pyrrolo[2,3-b]pyrazinyl, 1H-pyrrolo[2,3-b]pyridyl, --;
Line 56, should read -- 1H-imidazo[4,5-b]pyridyl, 1H-imidazo[4,5-c]pyridyl, --;
Line 57, 1H-imidazopyrazinyl," should read -- 1H-imidazo[4,5-b]pyrazinyl, --.

Column 56,
Lines 7 and 64, "benzothienyl," should read -- benzo[b]thienyl, --;
Line 16, "pyrrolopyridazinyl," should read -- pyrrolo[1,2-b]pyridazinyl, --;
Line 17, should read -- pyrazolo[1,5-a]pyridyl, imidazo[1,2-a]pyridyl, imidazo[1,5-a] pyridyl, --;
Line 18, should read -- imidazo[1,2-b]pyridazinyl, imidazo[1,2-a]pyrimidinyl, 1,2,4- --;
Line 19, "triazolopyridyl or 1,2,4-triazolopyridazinyl," should read -- triazolo[4,3-a] pyridyl, or 1,2,4-triazole[4,3-b]pyridazinyl --;
Line 32, "N-mono-C1-4" should read -- N-mono-$C_{1-4}$ --;
Line 36, "cyloalkyloxy," should read -- cycloalkyloxy, --;

Column 57,
Lines 5, 29 and 53, "pyrrolopyridazinyl," should read -- pyrrolo[1,2-b]pyridazinyl, --;
Lines 6, 30 and 54, -- pyrazolo[1,5-a]pyridyl, imidazo[1,2-a]pyridyl, imidazo[1,5-a] pyridyl, --;
Lines 7, 31 and 55, should read -- imidazo[1,2-b]pyridazinyl, imidazo[1,2-a] pyrimidinyl, 1,2,4- --;
Lines 8, 32 and 56, "triazolopyridyl or 1,2,4-triazolopyridazinyl," should read -- triazolo [4,3-a]pyridyl, or 1,2,4-triazole[4,3-b]pyridazinyl --.
Lines 20 and 44, "benzothienyl," should read -- benzo[b]thienyl, --;

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

<u>Column 58,</u>
Line 1, "cyloalkyoxy" should read -- cycloalkyloxy, --;
Line 14, "benzothienyl," should read -- benzo[b]thienyl, --;
Line 22, "pyrrolopyridazinyl," should read -- pyrrolo[1,2-b]pyridazinyl, --;
Line 23, should read -- pyrazolo[1,5-a]pyridyl, imidazo[1,2-a]pyridyl, imidazo[1,5-a]pyridyl, --;
Line 24, should read -- imidazo[1,2-b]pyridazinyl, imidazo[1,2-a]pyrimidinyl, 1,2,4- --;
Line 25, "triazolopyridyl, or 1,2,4-triazolopyridazinyl" should read -- triazolo[4,3-a]pyridyl, or 1,2,4-triazole[4,3-b]pyridazinyl --;
Line 58, "group" should read -- groups --;
Line 60, "claim 6," should read -- claim 14, --.

<u>Column 59,</u>
Lines 31 and 34, "which" should read -- which is --.

<u>Column 60,</u>
Line 21, "preventing and treating for" should read -- for preventing or treating --.

Signed and Sealed this

Twenty-eighth Day of May, 2002

Attest:

JAMES E. ROGAN
Attesting Officer       Director of the United States Patent and Trademark Office

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

Column 3,
Lines 31 and 37, "an" should be deleted;
Line 57, "perferably" should read -- preferable --.

Column 4,
Line 56, "arylsulfonyloxy" should read -- arylsulfonyloxy group --.

Column 5,
Line 19, "group." should read -- groups. --;
Line 32, "heteroarylalkyloxycarbonyl." should read
-- heteroarylalkyloxycarbonyl group. --;
Line 42, "as" should read -- as, --;
Line 61, "includes," should read -- include, --.

Column 6,
Line 4, "$R_6$ the" should read -- $R^6$, the --;
Line 66, "as for" should read -- as, for --.

Column 8,
Line 43, "preferable" should read -- preferably --;
Line 46, "a" should read -- an --;
Line 48, "morphorinyl" should read -- morpholinyl --.

Column 10,
Line 12, "-(CH$_2$)4-" should read -- -(CH$_2$)$_4$- --;
Line 51, "sugar" should read -- sugar- --.

Column 13,
Line 33, "herein above" should read -- hereinabove --.

Column 16,
Line 48, "aluminium" should read -- aluminum --;
Line 62, "The" should read -- ¶ The --.

Column 17,
Line 46, "transfer" should read -- transfer, --.

Column 22,
Line 27, "to" should be deleted.

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

Column 23,
Line 29, "iron," should read -- iron or --;
Line 35, "extration," should read -- extraction, --.

Column 24,
Line 26, "reducting" should read -- reducing --.

Column 25,
Lines 4 and 41, "extration," should read -- extraction, --;

Column 26,
Line 10, "extration," should read -- extraction, --;
Line 58, "aluminium" should read -- aluminum --.

Column 28,
Line 3, "temperature" should read -- time --;
Line 57, "hologen)" should read -- halogen) --.

Column 29,
Line 14, "ranges" should read -- ranges from --.

Column 30,
Line 17, "table 1," should read -- Table 1, --;
Lines 29 and 30, "with" should be deleted.

Column 34,
Line 63, "needls." should read -- needles. --.

Column 35,
Line 3, close up right margin;
Line 4, close up left margin;
Line 5, "prisms" should read -- prisms. --.

Column 37,
Line 30, "an" should be deleted.

Column 39,
Line 50, "oxazolep ropionic" should read -- oxazolepropionic --.

Column 40,
Lines 17 and 37, "aluminium" should read -- aluminum --.

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

<u>Column 41,</u>
Line 41, "-N-" should read -- N- --.

<u>Column 42,</u>
Line 13, "-4L" should read -- -4- --.

<u>Column 43,</u>
Line 5, "MgSO4)," should read -- $MgSO_4$), --;
Line 35, "15" should be deleted;
Line 37, "colorless" should read -- colorless prisms --;
Line 53, "35" should be deleted;
Line 66, ")" should be deleted.

<u>Column 44,</u>
Line 4, "(MgSO4)." should read -- $MgSO_4$). -- and "evaporated" should read -- evaporating --;
Line 18, "OC." should read -- 0ºC --.

<u>Column 45,</u>
Line 3, close up right margin;
Line 4, close up left margin;
Line 5, "--5-" should read -- -5- --;
Line 46, "QOC." should read -- 0ºC. --;
Line 63, "MgSO,)." should read -- $MgSO_4$). --.

<u>Column 46,</u>
Line 37, "ro" should read -- to --.

<u>Column 48,</u>
Line 35, "chlomatography." should read -- chromatography. --;
Line 59, "30" should be deleted.

<u>Column 49,</u>
Lines 7 and 37, "chlomatography." should read -- chromatography. --;
Line 45, "4-4-" should read -- 4-[4- --;
Line 50, "acetone-diethylether" should read -- acetone-diethyl ether --;
Line 63, "chlomatography." should read -- chromatography. --.

UNITED STATES PATENT AND TRADEMARK OFFICE
CERTIFICATE OF CORRECTION

PATENT NO. : 6,177,452 B1
DATED : January 23, 2001
INVENTOR(S) : Yu Momose et al.

It is certified that error appears in the above-identified patent and that said Letters Patent is hereby corrected as shown below:

Column 50,
Line 25, "chlomatography." should read -- chromatography. --;
Line 26, "1-(4-" should read -- 1-[4- --;
Line 57, "evaporated" should read -- evaporating --.

Column 51,
Line 34, "(Mg SO$_4$)." should read -- (MgSO$_4$). --.

Column 52,
Line 18, "are poorly toxic" should read -- exhibit low toxicity --;
Line 20, "secretion promoting" should read -- secretion-promoting --;
Line 42, "S as the," should read -- S, --;
Line 52, "where in" should read -- wherein --.

Column 53,
Line 5, "1H-pyrrolopyrazin-" should read -- 1H-pyrrolo[2,3-b]pyrazin- --;
Line 6, "1H-pyrrolopyridin-1-yl, 1H-imidazopyridin-1-yl," should read
-- 1H-pyrrolo[2,3-b]pyridin-1-yl, 1H-imidazo[4,5-b]pyridin-1-yl, --;
Line 7 should read -- 1H-imidazo[4,5-c]pyridin-1-yl, 1H-imidazo[4,5-b]pyrazin-1-yl, --;
Line 28 should read -- 1H-pyrrolo[2,3-b]pyrazinyl, 1H-pyrrolo[2,3-b]pyridyl, --;
Line 29 should read -- 1H-imidazo[4,5-b] pyridyl, 1Himidazo[4,5-c]pyridyl, --;
Line 30, "1H-imidazopyrazinyl," should read -- 1H-imidazo[4,5-b]pyrazinyl, --;
Line 46, "benzothienyl," should read -- benzo[b]thienyl, --;
Line 55, "pyrrolopyridazinyl," should read -- pyrrolo[1,2-b]pyridazinyl, --;
Line 56 should read -- pyrazolo[1,5-a]pyridyl, imidazo[1,2-a]pyridyl, imidazo[1,5-a] pyridyl, --;
Line 57 should read -- imidazo[1,2-b] pyridazinyl, imidazo[1,2-a]pyrimidinyl, 1,2,4 --;
Line 58, "triazolopyridyl, or 1,2,4-triazolopyridazinyl"
should read -- triazolo[4,3-a]pyridyl, or 1,2,4-triazolo[4,3-b]pyridazinyl --.

Column 54,
Line 4, "C$_{2-8}$, acylamino," should read -- C$_{2-8}$ acylamino, --;
Line 23, "C7-10" should read -- C$_{7-10}$ --;
Line 37, "benzothienyl," should read -- benzo[b]thienyl, --;
Line 46, "pyrrolopyridazinyl," should read -- pyrrolo[1,2-b] pyidazinyl, --;
Line 47 should read -- pyrazolo[1,5-a]pyridyl, imidazo[1,2-a]pyridyl, imidazo[1,5-a] pyridyl, --;
Line 48, should read -- imidazo[1,2-b]pyridazinyl, imidazo[1,2-a]pyrimidinyl, 1,2,4- --;
Line 49, "triazololpyridyl or 1,2,4-triazolopyridazinyl," should read -- triazolo[4,3-a] pyridyl or 1,2,4-triazole[4,3-b]pyridazinyl, --;
Line 62, "benzothienyl," should read -- benzo[b]thienyl, --.

UNITED STATES PATENT AND TRADEMARK OFFICE
CERTIFICATE OF CORRECTION

PATENT NO.    : 6,177,452 B1
DATED         : January 23, 2001
INVENTOR(S)   : Yu Momose et al.

It is certified that error appears in the above-identified patent and that said Letters Patent is hereby corrected as shown below:

Column 55,
Lines 4 and 27, "pyrrolopyridazinyl," should read -- pyrrolo[1,2-b]pyridazinyl, --;
Lines 5 and 28, should read -- pyrazolo[1,5-a]pyridyl, imidazo[1,2-a]pyridyl, imidazo [1,5-a]pyridyl, --;
Lines 6 and 29, should read -- imidazo[1,2-b]pyridazinyl, imidazo [1,2-a]pyrimidinyl, 1,2,4- --;
Lines 7 and 30, "triazolopyidyl or 1,2,4-triazolopyridazinyl," should read -- triazolo[4,3-a]pyridyl or 1,2,4-triazole[4,3-b]pyridazinyl, --.
Line 18, "benzothienyl," should read -- benzo[b]thienyl, --;
Line 23, "phthalazinyl" should read -- phthalazinyl, --;
Line 42, "cyloalkyloxy," should read -- cycloalkyloxy, --;
Line 50, "in," should read -- in --;
Line 55, should read -- 1H-pyrrolo[2,3-b]pyrazinyl, 1H-pyrrolo[2,3-b]pyridyl, --;
Line 56, should read -- 1H-imidazo[4,5-b]pyridyl, 1H-imidazo[4,5-c]pyridyl, --;
Line 57, 1H-imidazopyrazinyl," should read -- 1H-imidazo[4,5-b]pyrazinyl, --.

Column 56,
Lines 7 and 64, "benzothienyl," should read -- benzo[b]thienyl, --;
Line 16, "pyrrolopyridazinyl," should read -- pyrrolo[1,2-b]pyridazinyl, --;
Line 17, should read -- pyrazolo[1,5-a]pyridyl, imidazo[1,2-a]pyridyl, imidazo[1,5-a] pyridyl, --;
Line 18, should read -- imidazo[1,2-b]pyridazinyl, imidazo[1,2-a]pyrimidinyl, 1,2,4- --;
Line 19, "triazolopyridyl or 1,2,4-triazolopyridazinyl," should read -- triazolo[4,3-a] pyridyl, or 1,2,4-triazole[4,3-b]pyridazinyl --;
Line 32, "N-mono-C1-4" should read -- N-mono-$C_{1-4}$ --;
Line 36, "cyloalkyloxy," should read -- cycloalkyloxy, --;

Column 57,
Lines 5, 29 and 53, "pyrrolopyridazinyl," should read -- pyrrolo[1,2-b]pyridazinyl, --;
Lines 6, 30 and 54, -- pyrazolo[1,5-a]pyridyl, imidazo[1,2-a]pyridyl, imidazo[1,5-a] pyridyl, --;
Lines 7, 31 and 55, should read -- imidazo[1,2-b]pyridazinyl, imidazo[1,2-a] pyrimidinyl, 1,2,4- --;
Lines 8, 32 and 56, "triazolopyridyl or 1,2,4-triazolopyridazinyl," should read -- triazolo[4,3-a]pyridyl, or 1,2,4-triazole[4,3-b]pyridazinyl --.
Lines 20 and 44, "benzothienyl," should read -- benzo[b]thienyl, --;

UNITED STATES PATENT AND TRADEMARK OFFICE
CERTIFICATE OF CORRECTION

PATENT NO.   : 6,177,452 B1
DATED        : January 23, 2001
INVENTOR(S)  : Yu Momose et al.

It is certified that error appears in the above-identified patent and that said Letters Patent is hereby corrected as shown below:

<u>Column 58,</u>
Line 1, "cyloalkyoxy" should read -- cycloalkyloxy, --;
Line 14, "benzothienyl," should read -- benzo[b]thienyl, --;
Line 22, "pyrrolopyridazinyl," should read -- pyrrolo[1,2-b]pyridazinyl, --;
Line 23, should read -- pyrazolo[1,5-a]pyridyl, imidazo[1,2-a]pyridyl, imidazo[1,5-a]pyridyl, --;
Line 24, should read -- imidazo[1,2-b]pyridazinyl, imidazo[1,2-a]pyrimidinyl, 1,2,4- --;
Line 25, "triazolopyridyl, or 1,2,4-triazolopyridazinyl" should read -- triazolo[4,3-a]pyridyl, or 1,2,4-triazole[4,3-b]pyridazinyl --;
Line 58, "group" should read -- groups --;
Line 60, "claim 6," should read -- claim 14, --.

<u>Column 59,</u>
Lines 31 and 34, "which" should read -- which is --.

<u>Column 60,</u>
Line 21, "preventing and treating for" should read -- for preventing or treating --.

This certificate supersedes Certificate of Correction issued May 28, 2002 since this patent number did not appear on the Certificate of Correction listing for May 28, 2002

Signed and Sealed this

Sixteenth Day of July, 2002

*Attest:*

*Attesting Officer*

JAMES E. ROGAN
*Director of the United States Patent and Trademark Office*